US011021525B2

(12) United States Patent
Chou et al.

(10) Patent No.: US 11,021,525 B2
(45) Date of Patent: Jun. 1, 2021

(54) SYNTHETIC TRANSCRIPTION FACTOR AND USES THEREOF

(71) Applicant: The Regents of the University of California, Oakland, CA (US)

(72) Inventors: Howard H. Chou, Berkeley, CA (US); Jay D. Keasling, Berkeley, CA (US); Sergey Zotchev, Trondheim (NO)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/735,985

(22) Filed: Jun. 10, 2015

(65) Prior Publication Data

US 2015/0353614 A1 Dec. 10, 2015

Related U.S. Application Data

(63) Continuation of application No. PCT/US2013/074214, filed on Dec. 10, 2013.

(60) Provisional application No. 61/735,507, filed on Dec. 10, 2012.

(51) Int. Cl.
C07K 14/47 (2006.01)

(52) U.S. Cl.
CPC ...... *C07K 14/4702* (2013.01); *C07K 2319/00* (2013.01); *C07K 2319/70* (2013.01); *C07K 2319/80* (2013.01)

(58) Field of Classification Search
CPC ........ C07K 14/4702–14/4705; C07K 2319/00; C07K 2319/71; C07K 2319/80; C07K 2319/81; C07K 2319/715; C12N 9/1088; C12N 9/90; C12Y 205/0101; C12Y 503/03002
See application file for complete search history.

(56) References Cited

U.S. PATENT DOCUMENTS

| | | | | |
|---|---|---|---|---|
| 5,464,758 A * | 11/1995 | Gossen | ................ | C07K 14/005 435/320.1 |
| 6,365,410 B1 * | 4/2002 | Schellenberger | .... | C07K 14/245 435/243 |
| 2003/0049799 A1 * | 3/2003 | Schwartz | ............... | C07K 19/00 435/69.7 |
| 2004/0086972 A1 * | 5/2004 | Schellenberger | .... | C07K 14/245 435/69.1 |
| 2008/0220502 A1 | 9/2008 | Schellenberger et al. | | |
| 2009/0311790 A1 * | 12/2009 | Ogawa | ................. | C12N 9/1252 435/455 |
| 2012/0129254 A1 | 5/2012 | Bisgrove et al. | | |

OTHER PUBLICATIONS

Cronan, Jr. et al. FadR, transcriptional co-ordination of metabolic expediency. Molecular Microbiology, vol. 29, No. 4, pp. 937-943, 1998; Moras et al. Current Opinion in Cell Biology, vol. 10, pp. 384-391, 1998.*
Plano, GV. Modulation of AraC family member activity by protein ligands. Molecular Microbiology, vol. 54, No. 2, pp. 287-290, 2004.*
Pittard et al. The TyrR regulon. Molecular Microbiology, vol. 55, No. 1, pp. 16-26, 2005.*
Ramos et al. The TetR Family of Transcriptional Repressors. Microbiology and Molecular Biology Reviews, vol. 69, No. 2, pp. 326-356, Jun. 2005.*
Reichheld et al. The induction of folding cooperativity by ligand binding drives the allosteric response of the tetracycline receptor. Proceedings of the National Academy of Sciences, USA, vol. 106, No. 52, p. 22263-22268, Dec. 2009.*
Conte et al. pGOODs: new plasmids for the co-expression of proteins in *Escherichia coli*. Biotechnology Letters, vol. 33, pp. 1815-1821, Apr. 2011.*
Toellner et al. Low-level hypermutation in T cell-independent germinal centers as compared with hogh mutation rates associated with T cell-dependent germinal centers. The Journal of Experimental Medicine, vol. 195, No. 3, pp. 383-389, Feb. 2002.*
Chou, H. "Engineering the Synthesis of Five-Carbon Alcohols from Isopentenyl Diphosphate and Increasing its Production Using an Adaptive Control System." UC Berkeley: Bioengineering, Fall 2012.*
Raman et al. Engineering allostery. Trends in Genetics, vol. 30, No. 12, pp. 521-528, Dec. 2014.*
Taylor et al. Engineering an allosteric transcription factor to respond to new ligands. Nature Methods, vol. 13, No. 2, pp. 177-184, Feb. 2016, published online Dec. 21, 2015, including pp. 1/3-3/3 of Online Methods.*
International Search Report and Written Opinion for PCT/US2013/074214, dated Mar. 18, 2014.
Chou et al., "Programming adaptive control to evolve increased metabolite production", Nature Communications. 4:2595 (2013), 8 pages.
Dorf et al., "Introduction to Control System," Modern Control Systems, Prentice Hall, Mar. 12, 2004 (Mar. 12, 2004) pp. 1-36.
Nakamura et al., "Human mismatch repair gene, MLH1, is transcriptionally repressed by the hypoxia-inducible transcription factors, DEC1 and DEC2", Oncogene. 27:4200-4209 (2008).
Sasaki et al., "Genetic analysis of Bacillus subtilis mutator genes," J. Gen. Appl. Microbiol. 46: 183-187 (2000).
Wiegand et al., "Mutator genes giving rise to decreased antibiotic susceptibility in Pseudomonas aeruginosa," Antimicrobial Agents and Chemotherapy 52: 3810-3813 (2008).
D. Emlyn-Jones et al., "Nitrogen-regulated hypermutator strain of *Synechococcus* sp. for use in in vivo artificial evolution," Appl Environ Microbiol 69: 6427-6433 (2003).

(Continued)

*Primary Examiner* — Jennifer Dunston
(74) *Attorney, Agent, or Firm* — Robin C. Chiang; Lawrence Berkeley National Laboratory

(57) ABSTRACT

The present invention provides for a synthetic transcription factor (TF) comprising a first peptide capable of binding a target ligand, a second peptide capable of binding a target DNA, and a peptide linker linking the first and second peptides. The present invention also provide for a system for modulating the mutagenesis frequency of a host cell. The host cell has a mutator rate (R) which is inversely proportional to a phenotypic trait (P).

15 Claims, 22 Drawing Sheets

Specification includes a Sequence Listing.

(56) References Cited

OTHER PUBLICATIONS

Drotschmann et al., "Mutator phenotypes of yeast strains heterozygous for mutations in the MSH2 gene," PNASs 96: 2970-2975 (1999).
Kelberg et al., "HIM1, a new yeast *Saccharomyces cerevisiae* gene playing a role in control of spontaneous and induced mutagenesis," Mutat. Res. 578: 64-78 (2005).
Schaaper, "Mechanisms of mutagenesis in the *Escherichia coli* mutator mutD5: role of DNA mismatch repair." Proc. Natl. Acad. Sci. USA 85, 8126-8130 (1988).
Soisson et al., "Structural basis for ligand-regulated oligomerization of AraC." Science 276, 421-425 (1997).
Hahn et al., "*Escherichia coli* open reading frame 696 is idi, a nonessential gene encoding isopentenyl diphosphate isomerase." Journal of Bacteriology 181, 4499-4504 (1999).
Traven et al., "Yeast Gal4: a transcriptional paradigm revisited." EMBO 7, 496-499 (2006).
Fields et al., "A novel genetic system to detect protein-protein interactions." Nature 340, 245-246 (1989).
Robinson et al., "Optimizing the stability of single-chain proteins by linker length and composition mutagenesis. Proc. Natl." Acad. Sci. USA 95, 5929-5934 (1998).
Mayer et al., "Disruption and mapping of IDI, the gene for isopentenyl diphosphate isomerase in *Saccharomyces cerevisiae*." Yeast 8, 743-748 (1992).

Fischer et al., "Metabolic engineering of monoterpene synthesis in yeast." Biotechnology and Bioengineering 108, 1883-1892 (2011).
Rosche et al., "Determining Mutation Rates in Bacterial Populations". Methods 20, 4-17 (2000).
Alper et al., "Construction of lycopene-overproducing *E. coli* strains by combining systematic and combinatorial gene knockout targets." Nature Biotechnology 23, 612-616 (2005).
Lee et al., "Directed evolution of AraC for improved compatibility of arabinose- and lactose-inducible promoters." Applied and Environmental Microbiology 73, 5711-5715 (2007).
Jensen et al., "The sequence of spacers between the consensus sequences modulates the strength of prokaryotic promoters." Applied and Environmental Microbiology 64, 82-87 (1998).
Koyanagi et al, "Altered oligomerization properties of N316 mutants of *Escherichia coli* TyrR." Journal of Bacteriology 190, 8238-8243 (2008).
Yang et al., "Mechanism of repression of the aroP P2 promoter by the TyrR protein of *Escherichia coli*." Journal of Bacteriology 181, 6411-6418 (1999).
Lee et al., "Heterologous protein production in *Escherichia coli* using the propionate-inducible pPro system by conventional and auto-induction methods." Protein Expression and Purification 61, 197-203 (2008).
Price et al., "Orthologous Transcription Factors in Bacteria Have Different Functions and Regulate Different Genes", PLoS Computation Biology 3, 1739-1750 (2007).
Farnham, "Insights from genomic profiling of transcription factors," Nature Reviews Genetics 10, 605-616 (2009).

\* cited by examiner

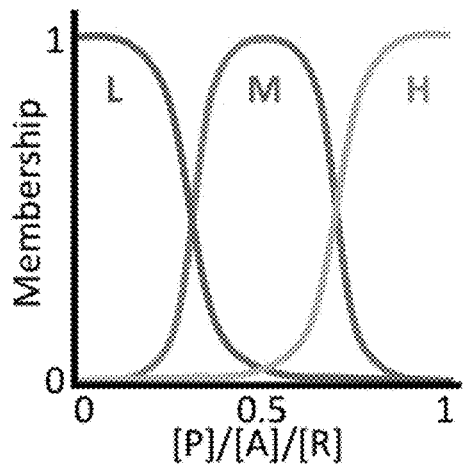
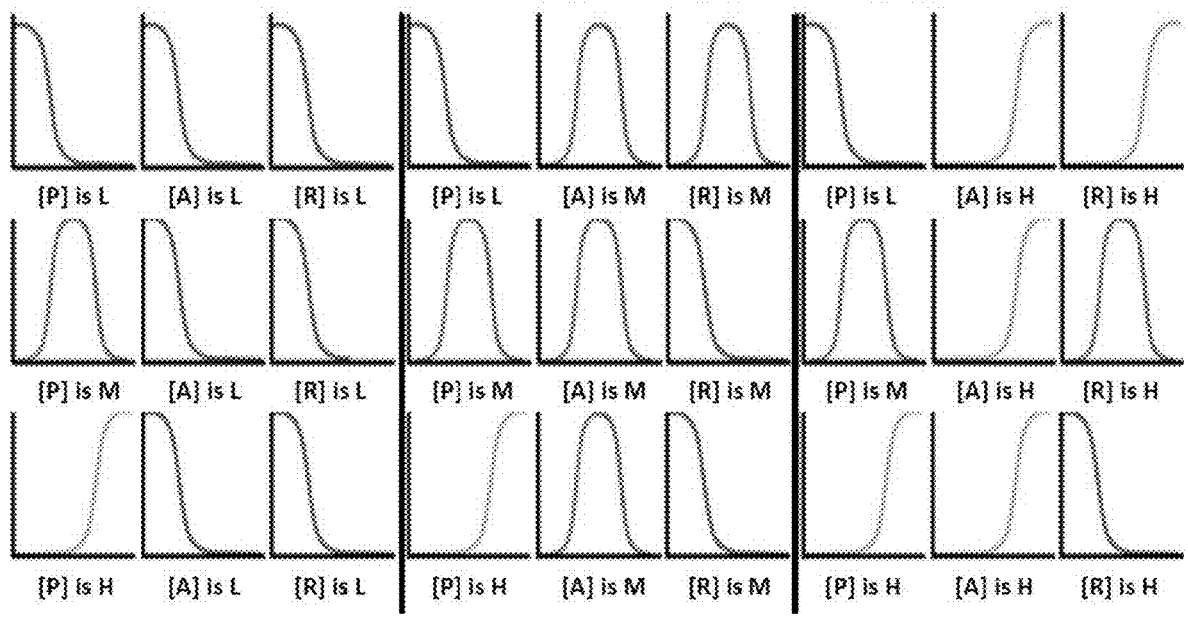
Figure 7
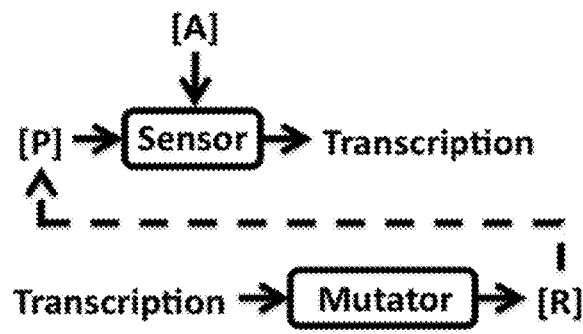
Figure 8

| Name | TyrR Modification | $P_{aroL}$ Modification |
|---|---|---|
| $S_{aroL0}$ | None | None |
| $S_{aroL1}$ | E274Q | None |
| $S_{aroL2}$ | N316K | None |
| $S_{aroL3}$ | E274Q, N316K | None |
| $S_{aroL4}$ | None | Box 1 and Box 2 |
| $S_{aroL5}$ | None | Box 3 |

| Name | TyrR Modification | $P_{aroP}$ Modification |
|---|---|---|
| $S_{aroP0}$ | None | None |
| $S_{aroP1}$ | E274Q | None |
| $S_{aroP2}$ | N316K | None |
| $S_{aroP3}$ | E274Q, N316K | None |
| $S_{aroP4}$ | None | $P_{2UP}$ |
| $S_{aroP5}$ | Δ43 | $P_{2UP}$ |
| $S_{aroP6}$ | Δ93 | $P_{2UP}$ |

\>Kan-F (SEQ ID NO:13)
GGCCCCGGGGTGTAGGCTGGAGCTGCTTC
\>Kan-R (SEQ ID NO:14)
GGCGAGCTCATGGGAATTAGCCATGGTCC
\>IdiKO-F (SEQ ID NO:15)
*ATCTATAATGATGAGTGATCAGAATTACATGTGAGAAATT*CCAGGCTTTACACTTTAT
\>IdiKO-R (SEQ ID NO:16)
*TTACGTTATGCTCACAACCCCGGCAAATGTCGGGGTTTT*TATGGGAATTAGCCATGGT
\>DelHindIII-F (SEQ ID NO:17)
CAGGCATGCTTGCTTGGCTGTTTT
\>DelHindIII-R (SEQ ID NO:18)
AAAACAGCCAAGCAAGCATGCCTG
\>RFP-F (SEQ ID NO:19)
GGCGGTACCTTAAGTAGGGAGGTAAATACATGGTTTCCAAGGGCGAGGAG
\>RFP-R (SEQ ID NO:20)
GGCTCTAGATTATTATTTGTACAGCTCATCCAT
\>Idi-F (SEQ ID NO:21)
GGCAAGCTTATGCAAACGGAACACGTCATT
\>Idi-SOE-R (SEQ ID NO:22)
ATGGAGCGACTCGTTAATTTTAAGCTGGGTAAATGC
\>AraC-SOE-F (SEQ ID NO:23)
ATTAACGAGTCGCTCCATCCA
\>AraC-R (SEQ ID NO:24)
GGCATCGATTTATGACAACTTGACGGCTAC
\>AC-F (SEQ ID NO:25)
GGCAAGCTTATTAACGAGTCGCTCCATCCA
\>I1I1-F (SEQ ID NO:55)
GGCGCTAGCCCAAAAAAACGGGTATGGAGAAACAGTAGAGAGTTGCGATAAAAAGCGTATGGAT
AAAAATGCTAATCTTATGGATAAAAATGCTA
\>I2I1-F (SEQ ID NO:56)
GGCGCTAGCCCAAAAAAACGGGTATGGAGAAACAGTAGAGAGTTGCGATAAAAAGCGTATGGAT
AAAAATGCTAATCTTCAGGTAGGATCCGCTATGGCA
\>I2I2-F (SEQ ID NO:57)
GGCGCTAGCCCAAAAAAACGGGTATGGAGAAACAGTAGAGAGTTGCGATAAAAAGCGTCAGGTA
GGATCCGCTAATCTTCAGGTAGGATCCGCTATGGCA
\>AraReg-R (SEQ ID NO:58)
GGCAAGCTTCATACTCCCGCCATTCAG
\>CFP-F (SEQ ID NO:59)
GGCATCGATTTAAGAAGGAGATATACATATGACTA
\>CFP-R (SEQ ID NO:60)
GGCTCCTGGACTATTATTTATACAGTTCATCCATGCC
\>CP20-F (SEQ ID NO:1)
GGCCGCTAGCCATGGGTGAGTTTATTCTTGACAGTGCGGCCGGGGGCTGATATCATAGCAGAGT
ACTATT CAATTTCACACAGGAAACAG AAGCTTGGCC

Figure 28-A

```
>CP20-R (SEQ ID NO:2)
GGCCAAGCTTCTGTTTCCTGTGTGAAATTGAATAGTACTCTGCTATGATATCAGCCCCCGGCCG
CACTGTCAAGAATAAACTCACCCATGGCTAGCGGCC
>TyrR-F (SEQ ID NO:3)
GGCAAGCTTATGCGTCTGGAAGTCTTTTGTGAA
>TyrR-R (SEQ ID NO:4)
GGCATCGATTACTCTTCGTTCTTCTTCTGACT
>AroF0-F (SEQ ID NO:5)
GGCGCTAGCCTTTTTCAAAGCATAGCGGATTGT
>AroF0-R (SEQ ID NO:6)
GGCGAATTCGATGGCGATCCTGTTTATGCTCGT
>TyrR-E274Q-F (SEQ ID NO:7)
CGGTCGAGAGTCAGCTGTTTGGTC
>TyrR-E274Q-R (SEQ ID NO:8)
GACCAAACAGCTGACTCTCGACCG
>TyrR-N316K-F (SEQ ID NO:9)
TGCGTTTCCTTAAAGATGGCACTT
>TyrR-N316K-R (SEQ ID NO:10)
AAGTGCCATCTTTAAGGAAACGCA
>Del43TyrR-F (SEQ ID NO:61)
GGCAAGCTTATGTTTGCTGAACTGGAGTTTGAGAGT
>Del93TyrR-F (SEQ ID NO:62)
GGCAAGCTTATGGTGCTCTCTGTCGATATGAAAAGC
>Del187TyrR-F (SEQ ID NO:63)
GGCAAGCTTATGCGTATGGGCCGCCAGTTGCAAAAT
>AroL0-F (SEQ ID NO:64)
GGCGCTAGCGCGGAGCTGGAGAAGTGGTGGCTG
>AroL0-R (SEQ ID NO:65)
GGCGAATTCCGTGGGTTTTCCCCAATAGGTCGC
>AroLBox1and2-F (SEQ ID NO:66)
TATTGAGATTTTCACTTTATCGAAGTGGAATTTTTTCTTT
>AroLBox1and2-R (SEQ ID NO:67)
AAAGAAAAAATTCCACTTCGATAAAGTGAAAATCTCAATA
>AroLBox3-F (SEQ ID NO:68)
TCGTGGCTAAATATAATTTATTATTTATACTTCATTCTTG
>AroLBox3-R (SEQ ID NO:69)
CAAGAATGAAGTATAAATAATAAATTATATTTAGCCACGA
>AroP0-F (SEQ ID NO:70)
GGCGCTAGCACCGATTCACTTACCAATTTTGTG
>AroP0-R (SEQ ID NO:71)
GGCGAATTCGAAACCTCGTGCGGTGGTTGTTTT
>P2UP-F (SEQ ID NO:72)
AAGTCTTTTGTTAACTTTCAAACTTCTTT
```

Figure 28-B

\>P2UP-R (SEQ ID NO:73)
AAAGAAGTTTGAAAGTTAACAAAAAGACTT
\>TEF-F (SEQ ID NO:26)
GGCGGATCCATAGCTTCAAAATGTTTCTAC
\>TEF-R (SEQ ID NO:27)
GGCCCCGGGAAACTTAGATTAGATTGCTAT
\>YEcitrine-F (SEQ ID NO:28)
GGCATCGATAACATGTCTAAAGGTGAAGAATTA
\>YEcitrine-R (SEQ ID NO:29)
GGCAGATCTTTATTTGTACAATTCATCCATACC
\>CYC1-SOE-F (SEQ ID NO:30)
GGCCTCGAGATCCGCTCTAACCGAAAAGGA
\>CYC1-SOE-R (SEQ ID NO:31)
GTAGAAACATTTTGAAGCTATCTTCGAGCGTCCCAAAACCTT
\>TEF-SOE-F (SEQ ID NO:32)
AAGGTTTTGGGACGCTCGAAGATAGCTTCAAAATGTTTCTAC
\>TEF-SOE-R (SEQ ID NO:33)
GGCAAGCTTAAACTTAGATTAGATTGCTATGCT
\>AD-F (SEQ ID NO:34)
GGCCCCGGGACCATGGCCAATTTTAATCAAAGTGGG
\>AD-SOE-R (SEQ ID NO:35)
ACCGGTTCCACCACCACTACCGCCTCCACTTCCGCCACCCTCTTTTTTTGGGTTTGGTGG
\>DBD-F (SEQ ID NO:36)
GGCAAGCTTACCATGAAGCTACTGTCTTCTATCGAA
\>DBD-SOE-R (SEQ ID NO:37)
ACCGGTTCCACCACCACTACCGCCTCCACTTCCGCCACCCGATACAGTCAACTGTCTTTG
\>GI-SOE-F (SEQ ID NO:38)
AGTGGTGGTGGAACCGGTGGAGGCAGTGGTGGAGGCCAAACGGAACACGTCATTTTATTG
\>AD-GI-R (SEQ ID NO:39)
GGCCTCGAGTTATTTAAGCTGGGTAAATGCAGA
\>DBD-GI-R (SEQ ID NO:40)
GGCGGTACCTTATTTAAGCTGGGTAAATGCAGA
\>GI1-SOE-F (SEQ ID NO:41)
AGTGGTGGTGGAACCGGTGGAGGCAGTGGTGGAGGCACTGCCGACAACAATAGTATG
\>AD-GI1-R (SEQ ID NO:42)
GGCCTCGAGTTATAGCATTCTATGAATTTGCCTG
\>DBD-GI1-R (SEQ ID NO:43)
GGCGGTACCTTATAGCATTCTATGAATTTGCCTG
\>GE20-SOE-F (SEQ ID NO:44)
AGTGGTGGTGGAACCGGTGGAGGCAGTGGTGGAGGCGCTTCAGAAAAAGAAATTAGGAGA
\>AD-GE20-R (SEQ ID NO:45)
GGCCTCGAGCTATTTGCTTCTCTTGTAAACTTT
\>DBD-GE20-R (SEQ ID NO:46)
GGCGGTACCCTATTTGCTTCTCTTGTAAACTTT

Figure 28-C

\>DelHindIII-Erg20-F (SEQ ID NO:47)
GCTATCTACAAGCTATTGAAATCT
\>DelHindIII-Erg20-R (SEQ ID NO:48)
AGATTTCAATAGCTTGTAGATAGC
\>DelKpnI-Erg20-F (SEQ ID NO:49)
ACTGCTTCGGTACTCCAGAAC
\>DelKpnI-Erg20-R (SEQ ID NO:50)
GTTCTGGAGTACCGAAGCAGT
\>IA-StrepII-F (SEQ ID NO:74)
GGCGGTACCATGGCTGAAGCGCAAAATGATC
\>IA-StrepII-R (SEQ ID NO:75)
GGCGGATCCTCACTTTTCGAACTGCGGGTGGCTCCATGACAACTTGACGGCTACATC
\>EMSA-AraReg-F (SEQ ID NO:76)
Cy5-AAGCTTCATACTCCCGCCATT
\>EMSA-AraReg-R (SEQ ID NO:77)
GAATTCCTCCTGCTAGCCCAA
\>EMSA-I1-F (SEQ ID NO:78)
Cy5-CACACTTTGCTATGCCATAGCATTTTATCCATAAGAT
\>EMSA-I1-R (SEQ ID NO:79)
ATCTTATGGATAAAAATGCTATGGCATAGCAAAGTGTG
\>EMSA-I1I2-F (SEQ ID NO:80)
Cy5-TGCTATGCCATAGCATTTTATCCATAAGATTAGCGGATCCTACCTGACGCTTTTTATCG
\>EMSA-I1I2-R (SEQ ID NO:81)
CGATAAAAAGCGTCAGGTAGGATCCGCTAATCTTATGGATAAAAATGCTATGGCATAGCA
\>I1-1F (SEQ ID NO:82)
FL-CACACTTTGCTATGCCATAGC
\>I1-2F (SEQ ID NO:83)
ATTTTTATCCATAAGAT
\>I1-3R (SEQ ID NO:84)
ATCTTATGGATAAAAATGCTA-BQ
\>I1-4R (SEQ ID NO:85)
TGGCATAGCAAAGTGTG
\>I1I2-1F (SEQ ID NO:86)
FL-TGCTATGCCATAGCATTTTATCCATAAGAT
\>I1 I2-2F (SEQ ID NO:87)
TAGCGGATCCTACCTGACGCTTTTTAT
\>I1 I2-3R (SEQ ID NO:88)
ATAAAAAGCGTCAGGTAGGATCCGCTAATCT-BQ
\>I1 I2-4R (SEQ ID NO:89)
TATGGATAAAAATGCTATGGCATAGCA
\>MutD-F (SEQ ID NO:11)
GGCGAATTCTTTAAGAAGGAGATATACATATGA
\>MutD-R (SEQ ID NO:12)
GGCGGTACCTTATGCTCGCCAGAGGCAACTTCC

Figure 28-D

SEQUENCE LISTING

<160> NUMBER OF SEQ ID NOS: 89

<210> SEQ ID NO 1
<211> LENGTH: 100
<212> TYPE: DNA
<213> ORGANISM: Escherichia coli

<400> SEQUENCE: 1
ggccgctagc catgggtgag tttattcttg acagtgcggc cgggggctga tatcatagca    60
gagtactatt caatttcaca caggaaacag aagcttggcc                         100

<210> SEQ ID NO 2
<211> LENGTH: 100
<212> TYPE: DNA
<213> ORGANISM: Escherichia coli

<400> SEQUENCE: 2
ggccaagctt ctgtttcctg tgtgaaattg aatagtactc tgctatgata tcagccccg    60 gccgcactgt caagaataaa ctcacccatg gctagcggcc                         100

<210> SEQ ID NO 3
<211> LENGTH: 33
<212> TYPE: DNA
<213> ORGANISM: Escherichia coli

<400> SEQUENCE: 3
ggcaagctta tgcgtctgga agtcttttgt gaa                                33

<210> SEQ ID NO 4
<211> LENGTH: 33
<212> TYPE: DNA
<213> ORGANISM: Escherichia coli

<400> SEQUENCE: 4
ggcatcgatt tactcttcgt tcttcttctg act                                33

<210> SEQ ID NO 5
<211> LENGTH: 33
<212> TYPE: DNA
<213> ORGANISM: Escherichia coli

<400> SEQUENCE: 5
ggcgctagcc tttttcaaag catagcggat tgt                                33

<210> SEQ ID NO 6
<211> LENGTH: 33
<212> TYPE: DNA
<213> ORGANISM: Escherichia coli

<400> SEQUENCE: 6
ggcgaattcg atggcgatcc tgtttatgct cgt                                33

<210> SEQ ID NO 7
<211> LENGTH: 24
<212> TYPE: DNA
<213> ORGANISM: Escherichia coli

<400> SEQUENCE: 7
cggtcgagag tcagctgttt ggtc                                          24

```
<210> SEQ ID NO 8
<211> LENGTH: 24
<212> TYPE: DNA
<213> ORGANISM: Escherichia coli

<400> SEQUENCE: 8
gaccaaacag ctgactctcg accg                                          24

<210> SEQ ID NO 9
<211> LENGTH: 24
<212> TYPE: DNA
<213> ORGANISM: Escherichia coli

<400> SEQUENCE: 9
tgcgtttcct taaagatggc actt                                          24

<210> SEQ ID NO 10
<211> LENGTH: 24
<212> TYPE: DNA
<213> ORGANISM: Escherichia coli

<400> SEQUENCE: 10
aagtgccatc tttaaggaaa cgca                                          24

<210> SEQ ID NO 11
<211> LENGTH: 33
<212> TYPE: DNA
<213> ORGANISM: Escherichia coli

<400> SEQUENCE: 11
ggcgaattct ttaagaagga gatatacata tga                                33

<210> SEQ ID NO 12
<211> LENGTH: 33
<212> TYPE: DNA
<213> ORGANISM: Escherichia coli

<400> SEQUENCE: 12
ggcggtacct tatgctcgcc agaggcaact tcc                                33

<210> SEQ ID NO 13
<211> LENGTH: 29
<212> TYPE: DNA
<213> ORGANISM: Escherichia coli

<400> SEQUENCE: 13
ggccccgggg tgtaggctgg agctgcttc                                     29

<210> SEQ ID NO 14
<211> LENGTH: 29
<212> TYPE: DNA
<213> ORGANISM: Escherichia coli

<400> SEQUENCE: 14
ggcgagctca tgggaattag ccatggtcc                                     29

<210> SEQ ID NO 15
<211> LENGTH: 58
<212> TYPE: DNA
<213> ORGANISM: Escherichia coli

<400> SEQUENCE: 15
atctataatg atgagtgatc agaattacat gtgagaaatt ccaggcttta cactttat    58
```

```
<210> SEQ ID NO 16
<211> LENGTH: 58
<212> TYPE: DNA
<213> ORGANISM: Escherichia coli

<400> SEQUENCE: 16
ttacgttatg ctcacaaccc cggcaaatgt cggggttttt atgggaatta gccatggt      58

<210> SEQ ID NO 17
<211> LENGTH: 24
<212> TYPE: DNA
<213> ORGANISM: Escherichia coli

<400> SEQUENCE: 17
caggcatgct tgcttggctg tttt                                            24

<210> SEQ ID NO 18
<211> LENGTH: 24
<212> TYPE: DNA
<213> ORGANISM: Escherichia coli

<400> SEQUENCE: 18
aaaacagcca agcaagcatg cctg                                            24

<210> SEQ ID NO 19
<211> LENGTH: 50
<212> TYPE: DNA
<213> ORGANISM: Escherichia coli

<400> SEQUENCE: 19
ggcggtacct taagtaggga ggtaaataca tggtttccaa gggcgaggag                50

<210> SEQ ID NO 20
<211> LENGTH: 33
<212> TYPE: DNA
<213> ORGANISM: Escherichia coli

<400> SEQUENCE: 20
ggctctagat tattatttgt acagctcatc cat                                  33

<210> SEQ ID NO 21
<211> LENGTH: 30
<212> TYPE: DNA
<213> ORGANISM: Escherichia coli

<400> SEQUENCE: 21
ggcaagctta tgcaaacgga acacgtcatt                                      30

<210> SEQ ID NO 22
<211> LENGTH: 36
<212> TYPE: DNA
<213> ORGANISM: Escherichia coli

<400> SEQUENCE: 22
atggagcgac tcgttaattt taagctgggt aaatgc                               36

<210> SEQ ID NO 23
<211> LENGTH: 21
<212> TYPE: DNA
<213> ORGANISM: Escherichia coli

<400> SEQUENCE: 23
attaacgagt cgctccatcc a                                               21
```

```
<210> SEQ ID NO 24
<211> LENGTH: 30
<212> TYPE: DNA
<213> ORGANISM: Escherichia coli

<400> SEQUENCE: 24
ggcatcgatt tatgacaact tgacggctac                                    30

<210> SEQ ID NO 25
<211> LENGTH: 30
<212> TYPE: DNA
<213> ORGANISM: Escherichia coli

<400> SEQUENCE: 25
ggcaagctta ttaacgagtc gctccatcca                                    30

<210> SEQ ID NO 26
<211> LENGTH: 30
<212> TYPE: DNA
<213> ORGANISM: Saccharomyces cerevisiae

<400> SEQUENCE: 26
ggcggatcca tagcttcaaa atgtttctac                                    30

<210> SEQ ID NO 27
<211> LENGTH: 30
<212> TYPE: DNA
<213> ORGANISM: Saccharomyces cerevisiae

<400> SEQUENCE: 27
ggccccggga aacttagatt agattgctat                                    30

<210> SEQ ID NO 28
<211> LENGTH: 33
<212> TYPE: DNA
<213> ORGANISM: Saccharomyces cerevisiae

<400> SEQUENCE: 28
ggcatcgata acatgtctaa aggtgaagaa tta                                33

<210> SEQ ID NO 29
<211> LENGTH: 33
<212> TYPE: DNA
<213> ORGANISM: Saccharomyces cerevisiae

<400> SEQUENCE: 29
ggcagatctt tatttgtaca attcatccat acc                                33

<210> SEQ ID NO 30
<211> LENGTH: 30
<212> TYPE: DNA
<213> ORGANISM: Saccharomyces cerevisiae

<400> SEQUENCE: 30
ggcctcgaga tccgctctaa ccgaaaagga                                    30

<210> SEQ ID NO 31
<211> LENGTH: 42
<212> TYPE: DNA
<213> ORGANISM: Saccharomyces cerevisiae

<400> SEQUENCE: 31
gtagaaacat tttgaagcta tcttcgagcg tcccaaaacc tt                      42
```

<210> SEQ ID NO 32
<211> LENGTH: 42
<212> TYPE: DNA
<213> ORGANISM: Saccharomyces cerevisiae

<400> SEQUENCE: 32
aaggttttgg gacgctcgaa gatagcttca aaatgtttct ac        42

<210> SEQ ID NO 33
<211> LENGTH: 33
<212> TYPE: DNA
<213> ORGANISM: Saccharomyces cerevisiae

<400> SEQUENCE: 33
ggcaagctta aacttagatt agattgctat gct        33

<210> SEQ ID NO 34
<211> LENGTH: 36
<212> TYPE: DNA
<213> ORGANISM: Saccharomyces cerevisiae

<400> SEQUENCE: 34
ggccccggga ccatggccaa ttttaatcaa agtggg        36

<210> SEQ ID NO 35
<211> LENGTH: 60
<212> TYPE: DNA
<213> ORGANISM: Saccharomyces cerevisiae

<400> SEQUENCE: 35
accggttcca ccaccactac cgcctccact tccgccaccc tcttttttg ggtttggtgg        60

<210> SEQ ID NO 36
<211> LENGTH: 36
<212> TYPE: DNA
<213> ORGANISM: Saccharomyces cerevisiae

<400> SEQUENCE: 36
ggcaagctta ccatgaagct actgtcttct atcgaa        36

<210> SEQ ID NO 37
<211> LENGTH: 60
<212> TYPE: DNA
<213> ORGANISM: Escherichia coli

<400> SEQUENCE: 37
accggttcca ccaccactac cgcctccact tccgccaccc gatacagtca actgtctttg        60

<210> SEQ ID NO 38
<211> LENGTH: 60
<212> TYPE: DNA
<213> ORGANISM: Escherichia coli

<400> SEQUENCE: 38
agtggtggtg gaaccggtgg aggcagtggt ggaggccaaa cggaacacgt cattttattg        60

<210> SEQ ID NO 39
<211> LENGTH: 33
<212> TYPE: DNA
<213> ORGANISM: Escherichia coli

<400> SEQUENCE: 39
ggcctcgagt tatttaagct gggtaaatgc aga        33

<210> SEQ ID NO 40
<211> LENGTH: 33
<212> TYPE: DNA
<213> ORGANISM: Escherichia coli

<400> SEQUENCE: 40
ggcggtacct tatttaagct gggtaaatgc aga        33

<210> SEQ ID NO 41
<211> LENGTH: 57
<212> TYPE: DNA
<213> ORGANISM: Saccharomyces cerevisiae

<400> SEQUENCE: 41
agtggtggtg aaccggtgg aggcagtggt ggaggcactg ccgacaacaa tagtatg        57

<210> SEQ ID NO 42
<211> LENGTH: 34
<212> TYPE: DNA
<213> ORGANISM: Saccharomyces cerevisiae

<400> SEQUENCE: 42
ggcctcgagt tatagcattc tatgaatttg cctg        34

<210> SEQ ID NO 43
<211> LENGTH: 34
<212> TYPE: DNA
<213> ORGANISM: Saccharomyces cerevisiae

<400> SEQUENCE: 43
ggcggtacct tatagcattc tatgaatttg cctg        34

<210> SEQ ID NO 44
<211> LENGTH: 60
<212> TYPE: DNA
<213> ORGANISM: Saccharomyces cerevisiae

<400> SEQUENCE: 44
agtggtggtg aaccggtgg aggcagtggt ggaggcgctt cagaaaaaga aattaggaga        60

<210> SEQ ID NO 45
<211> LENGTH: 33
<212> TYPE: DNA
<213> ORGANISM: Saccharomyces cerevisiae

<400> SEQUENCE: 45
ggcctcgagc tatttgcttc tcttgtaaac ttt        33

<210> SEQ ID NO 46
<211> LENGTH: 33
<212> TYPE: DNA
<213> ORGANISM: Saccharomyces cerevisiae

<400> SEQUENCE: 46
ggcggtaccc tatttgcttc tcttgtaaac ttt        33

<210> SEQ ID NO 47
<211> LENGTH: 24
<212> TYPE: DNA
<213> ORGANISM: Saccharomyces cerevisiae

<400> SEQUENCE: 47
gctatctaca agctattgaa atct        24

<210> SEQ ID NO 48
<211> LENGTH: 24
<212> TYPE: DNA
<213> ORGANISM: Saccharomyces cerevisiae

<400> SEQUENCE: 48
agatttcaat agcttgtaga tagc                                            24

<210> SEQ ID NO 49
<211> LENGTH: 21
<212> TYPE: DNA
<213> ORGANISM: Saccharomyces cerevisiae

<400> SEQUENCE: 49
actgcttcgg tactccagaa c                                               21

<210> SEQ ID NO 50
<211> LENGTH: 21
<212> TYPE: DNA
<213> ORGANISM: Saccharomyces cerevisiae

<400> SEQUENCE: 50
gttctggagt accgaagcag t                                               21

<210> SEQ ID NO 51
<211> LENGTH: 38
<212> TYPE: DNA
<213> ORGANISM: Escherichia coli

<400> SEQUENCE: 51
tagcattttt atccataaga ttagcattttt tatccata                            38

<210> SEQ ID NO 52
<211> LENGTH: 38
<212> TYPE: DNA
<213> ORGANISM: Escherichia coli

<400> SEQUENCE: 52
tagcattttt atccataaga ttagcggatc ctacctga                             38

<210> SEQ ID NO 53
<211> LENGTH: 38
<212> TYPE: DNA
<213> ORGANISM: Escherichia coli

<400> SEQUENCE: 53
tagcggatcc tacctgaaga ttagcattttt tatccata                            38

<210> SEQ ID NO 54
<211> LENGTH: 38
<212> TYPE: DNA
<213> ORGANISM: Escherichia coli

<400> SEQUENCE: 54
tagcggatcc tacctgaaga ttagcggatc ctacctga                             38

<210> SEQ ID NO 55
<211> LENGTH: 95
<212> TYPE: DNA
<213> ORGANISM: Escherichia coli

<400> SEQUENCE: 55
ggcgctagcc caaaaaaacg ggtatggaga aacagtagag agttgcgata aaaagcgtat    60
ggataaaaat gctaatctta tggataaaaa tgcta    95

<210> SEQ ID NO 56
<211> LENGTH: 100
<212> TYPE: DNA
<213> ORGANISM: Escherichia coli

<400> SEQUENCE: 56
ggcgctagcc caaaaaaacg ggtatggaga aacagtagag agttgcgata aaaagcgtat    60
ggataaaaat gctaatcttc aggtaggatc cgctatggca    100

<210> SEQ ID NO 57
<211> LENGTH: 100
<212> TYPE: DNA
<213> ORGANISM: Escherichia coli

<400> SEQUENCE: 57
ggcgctagcc caaaaaaacg ggtatggaga aacagtagag agttgcgata aaaagcgtca    60
ggtaggatcc gctaatcttc aggtaggatc cgctatggca    100

<210> SEQ ID NO 58
<211> LENGTH: 27
<212> TYPE: DNA
<213> ORGANISM: Saccharomyces cerevisiae

<400> SEQUENCE: 58
ggcaagcttc atactcccgc cattcag    27

<210> SEQ ID NO 59
<211> LENGTH: 36
<212> TYPE: DNA
<213> ORGANISM: Saccharomyces cerevisiae

<400> SEQUENCE: 59
ggcatcgatt ttaagaagga gatatacata tgacta    36

<210> SEQ ID NO 60
<211> LENGTH: 37
<212> TYPE: DNA
<213> ORGANISM: Saccharomyces cerevisiae

<400> SEQUENCE: 60
ggctcctgga ctattattta tacagttcat ccatgcc    37

<210> SEQ ID NO 61
<211> LENGTH: 36
<212> TYPE: DNA
<213> ORGANISM: Escherichia coli

<400> SEQUENCE: 61
ggcaagctta tgtttgctga actggagttt gagagt    36

<210> SEQ ID NO 62
<211> LENGTH: 36
<212> TYPE: DNA
<213> ORGANISM: Escherichia coli

<400> SEQUENCE: 62
ggcaagctta tggtgctctc tgtcgatatg aaaagc    36

```
<210> SEQ ID NO 63
<211> LENGTH: 36
<212> TYPE: DNA
<213> ORGANISM: Escherichia coli

<400> SEQUENCE: 63
ggcaagctta tgcgtatggg ccgccagttg caaaat                        36

<210> SEQ ID NO 64
<211> LENGTH: 33
<212> TYPE: DNA
<213> ORGANISM: Escherichia coli

<400> SEQUENCE: 64
ggcgctagcg cggagctgga gaagtggtgg ctg                           33

<210> SEQ ID NO 65
<211> LENGTH: 33
<212> TYPE: DNA
<213> ORGANISM: Escherichia coli

<400> SEQUENCE: 65
ggcgaattcc gtgggttttc cccaataggt cgc                           33

<210> SEQ ID NO 66
<211> LENGTH: 40
<212> TYPE: DNA
<213> ORGANISM: Escherichia coli

<400> SEQUENCE: 66
tattgagatt ttcactttat cgaagtggaa ttttttcttt                    40

<210> SEQ ID NO 67
<211> LENGTH: 40
<212> TYPE: DNA
<213> ORGANISM: Escherichia coli

<400> SEQUENCE: 67
aaagaaaaaa ttccacttcg ataaagtgaa aatctcaata                    40

<210> SEQ ID NO 68
<211> LENGTH: 40
<212> TYPE: DNA
<213> ORGANISM: Escherichia coli

<400> SEQUENCE: 68
tcgtggctaa atataattta ttatttatac ttcattcttg                    40

<210> SEQ ID NO 69
<211> LENGTH: 40
<212> TYPE: DNA
<213> ORGANISM: Escherichia coli

<400> SEQUENCE: 69
caagaatgaa gtataaataa taaattatat ttagccacga                    40

<210> SEQ ID NO 70
<211> LENGTH: 33
<212> TYPE: DNA
<213> ORGANISM: Escherichia coli

<400> SEQUENCE: 70
ggcgctagca ccgattcact taccaatttt gtg                           33
```

```
<210> SEQ ID NO 71
<211> LENGTH: 33
<212> TYPE: DNA
<213> ORGANISM: Escherichia coli

<400> SEQUENCE: 71
ggcgaattcg aaacctcgtg cggtggttgt ttt                          33

<210> SEQ ID NO 72
<211> LENGTH: 30
<212> TYPE: DNA
<213> ORGANISM: Escherichia coli

<400> SEQUENCE: 72
aagtcttttt gttaactttc aaacttcttt                              30

<210> SEQ ID NO 73
<211> LENGTH: 30
<212> TYPE: DNA
<213> ORGANISM: Escherichia coli

<400> SEQUENCE: 73
aaagaagttt gaaagttaac aaaaagactt                              30

<210> SEQ ID NO 74
<211> LENGTH: 31
<212> TYPE: DNA
<213> ORGANISM: Escherichia coli

<400> SEQUENCE: 74
ggcggtacca tggctgaagc gcaaaatgat c                            31

<210> SEQ ID NO 75
<211> LENGTH: 57
<212> TYPE: DNA
<213> ORGANISM: Escherichia coli

<400> SEQUENCE: 75
ggcggatcct cactttttcga actgcgggtg gctccatgac aacttgacgg ctacatc    57

<210> SEQ ID NO 76
<211> LENGTH: 21
<212> TYPE: DNA
<213> ORGANISM: Escherichia coli

<400> SEQUENCE: 76
aagcttcata ctcccgccat t                                       21

<210> SEQ ID NO 77
<211> LENGTH: 21
<212> TYPE: DNA
<213> ORGANISM: Escherichia coli

<400> SEQUENCE: 77
gaattcctcc tgctagccca a                                       21

<210> SEQ ID NO 78
<211> LENGTH: 38
<212> TYPE: DNA
<213> ORGANISM: Escherichia coli

<400> SEQUENCE: 78
cacactttgc tatgccatag cattttatc cataagat                      38
```

```
<210> SEQ ID NO 79
<211> LENGTH: 38
<212> TYPE: DNA
<213> ORGANISM: Escherichia coli

<400> SEQUENCE: 79
atcttatgga taaaaatgct atggcatagc aaagtgtg                            38

<210> SEQ ID NO 80
<211> LENGTH: 60
<212> TYPE: DNA
<213> ORGANISM: Escherichia coli

<400> SEQUENCE: 80
tgctatgcca tagcattttt atccataaga ttagcggatc ctacctgacg cttttttatcg   60

<210> SEQ ID NO 81
<211> LENGTH: 60
<212> TYPE: DNA
<213> ORGANISM: Escherichia coli

<400> SEQUENCE: 81
cgataaaaag cgtcaggtag gatccgctaa tcttatggat aaaaatgcta tggcatagca   60

<210> SEQ ID NO 82
<211> LENGTH: 21
<212> TYPE: DNA
<213> ORGANISM: Escherichia coli

<400> SEQUENCE: 82
cacactttgc tatgccatag c                                             21

<210> SEQ ID NO 83
<211> LENGTH: 17
<212> TYPE: DNA
<213> ORGANISM: Escherichia coli

<400> SEQUENCE: 83 attttttatcc ataagat                                                 17

<210> SEQ ID NO 84
<211> LENGTH: 21
<212> TYPE: DNA
<213> ORGANISM: Escherichia coli

<400> SEQUENCE: 84
atcttatgga taaaaatgct a                                             21

<210> SEQ ID NO 85
<211> LENGTH: 17
<212> TYPE: DNA
<213> ORGANISM: Escherichia coli

<400> SEQUENCE: 85
tggcatagca aagtgtg                                                  17

<210> SEQ ID NO 86
<211> LENGTH: 31
<212> TYPE: DNA
<213> ORGANISM: Escherichia coli

<400> SEQUENCE: 86
tgctatgcca tagcattttt atccataaga t                                  31
```

```
<210> SEQ ID NO 87
<211> LENGTH: 27
<212> TYPE: DNA
<213> ORGANISM: Escherichia coli

<400> SEQUENCE: 87
tagcggatcc tacctgacgc tttttat                                         27

<210> SEQ ID NO 88
<211> LENGTH: 31
<212> TYPE: DNA
<213> ORGANISM: Escherichia coli

<400> SEQUENCE: 88
ataaaaagcg tcaggtagga tccgctaatc t                                    31

<210> SEQ ID NO 89
<211> LENGTH: 27
<212> TYPE: DNA
<213> ORGANISM: Escherichia coli

<400> SEQUENCE: 89
tatggataaa aatgctatgg catagca                                         27
```

SYNTHETIC TRANSCRIPTION FACTOR AND USES THEREOF

CROSS-REFERENCE TO RELATED APPLICATIONS

This application claims priority as a continuation application of PCT International Patent Application No. PCT/US13/74214, filed Dec. 10, 2013, which claims priority to U.S. Provisional Patent Application Ser. No. 61/735,507, filed Dec. 10, 2012, both of which are hereby incorporated by reference in their entireties.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of gene expression.

BACKGROUND OF THE INVENTION

The complexity inherent in biological systems challenges efforts to rationally engineer novel phenotypes, especially those not amenable to high-throughput screens and selections. In nature, adaptation can rapidly evolve new traits by changing the mutation rate in a cell.

Adaptation is a behavior that allows cells to survive and thrive in constantly changing environmental conditions. This behavior is characterized by rapid genetic change creating rare beneficial mutations[1]. The appearance of microbial strains with higher than average mutation rates accompany periods of adaptation in both natural and laboratory environments[2-4]. Models and experimental data of the adaptive process indicate a variable mutation rate strategy is used to evolve traits, where increased mutation rates are only beneficial to populations with low phenotypic diversity, while populations with high degrees of diversity benefit from decreased mutation rates[5-7].

Many mutagenesis strategies to generate diversity in the laboratory exist, but most industrially-important phenotypes are not amenable to the high-throughput screens and selections required to isolate mutants exhibiting the desired traits[8,9]. Furthermore, directed evolution strategies that generate mutant libraries in vitro are limited by the transformation efficiency of the cell, and those that use mutator strains demonstrating unregulated high mutation rates to generate mutant libraries in vivo[10] suffer from the accumulation of deleterious mutations that eventually lead to cell death. Although adaptation has proven useful for evolving certain phenotypes, its application is limited to traits that are directly tied to growth[11]. Therefore, a method capable of regulating mutagenesis in vivo according to a particular phenotype, independent of whether it is linked to growth, could circumvent the constraints set by transformation inefficiencies, deleterious mutations, and assay availability.

SUMMARY OF THE INVENTION

The present invention provides for a synthetic transcription factor (TF) comprising a first peptide capable of binding a target ligand, a second peptide capable of binding a target DNA, and a peptide linker linking the first and second peptides. In some embodiments, the target DNA is an activator or repressor site of a gene of interest. Depending on the target DNA and the gene of interest, the binding of target DNA by the synthetic TF can either activate or repress transcription of the gene of interest from a target promoter.

The present invention provide for a system for modulating the mutagenesis frequency of a host cell. The host cell has a mutator rate (R) which is inversely proportional to a phenotypic trait (P). The host cell comprises a sensor module and a mutator module. The sensor module comprises a target ligand, a TF (such as a synthetic TF) that binds the target ligand, and a target promoter regulated by the TF. The mutator module comprises the target promoter operably linked to a gene that increases mutation rate (mutator or mutator gene) of the host cell. The system comprises a host cell comprising a synthetic TF, a target DNA which the binding thereof modulates the expression of the gene that increases mutation rate of the host cell.

The present invention also provides for a genetically modified host cell comprising the synthetic TF or system useful for the methods of the present invention.

BRIEF DESCRIPTION OF THE DRAWINGS

The foregoing aspects and others will be readily appreciated by the skilled artisan from the following description of illustrative embodiments when read in conjunction with the accompanying drawings.

FIG. 7. (Top) Three membership functions (L, M, and H representing low, medium, high states, respectively) for describing the inputs and output of the FREP algorithm. The inputs are phenotypic diversity related to the trait being evolved (P) and attenuation (A), and the output is the mutation rate (R). A is a constraint on the maximum value for R. (Bottom) Rule table for relating input to output. Rules are listed as "IF [P] AND [A] THEN [R]" using the input and output states as descriptors. For example, the rule at the bottom-right corner states "IF P (phenotypic diversity) is high AND A (attenuation) is high THEN R (mutation rate) is low".

FIG. 8. Implementation of FREP using a sensor and mutator module. The sensor module converts the inputs A and P into a transcriptional level, which the mutator module converts to R. A constrains the strength and dynamics of the transcriptional output. R affects P, creating a feedback loop between the two modules.

FIG. 28, A-D. Primer sequences. Sequences of primers (5' to 3') used to assemble plasmids in this study. Underlined parts indicate restriction sites unless otherwise indicated.

DETAILED DESCRIPTION OF THE INVENTION

Figure 1:
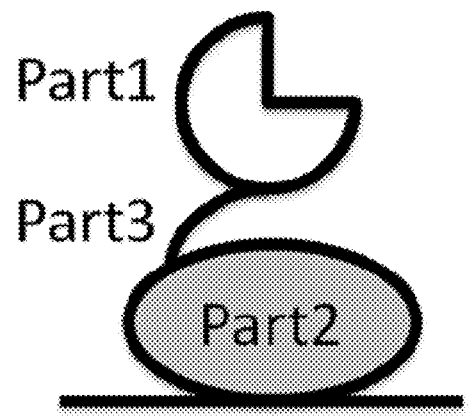
FIG. 1. Design of Synthetic Transcription Factor (TF). Part1 is a protein or protein domain (e.g., ligand-binding domain of a natural TF) that binds the target ligand, Part2 is an activation or DNA-binding domain, and Part3 is a DNA sequence fusing together Part1 and Part2.

Before the invention is described in detail, it is to be understood that, unless otherwise indicated, this invention is not limited to particular sequences, expression vectors, synthetic TF, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for peptides and proteins that is not normally found in a host microorganism. With reference to the host microorganism's genome, then, the nucleic acid sequence that codes for the peptides and proteins is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

Method for Constructing Synthetic Transcription Factors

The present invention provides for a synthetic transcription factor (TF) comprising a first peptide capable of binding a target ligand, a second peptide capable of binding a target DNA, and a peptide linker linking the first and second peptides. In some embodiments, the target DNA is an activator or repressor site of a gene of interest. Depending on the target DNA and the gene of interest, the binding of target DNA by the synthetic TF can either activate or repress transcription of the gene of interest from a target promoter.

In some embodiments, the presence of the target ligand causes the synthetic TF to not bind the target DNA, while the absence of the target ligand causes the synthetic TF to bind the target DNA.

In some embodiments, the presence of the target ligand causes the synthetic TF to bind the target DNA, while the absence of the target ligand causes the synthetic TF to not bind the target DNA.

In some embodiments, the first peptide is a ligand-binding domain of a natural TF, such as Idi. In some embodiments, the second peptide is a DNA-binding domain (DBD) of a natural protein, such as the DBD of AraC.

The present invention provides for a nucleic acid comprising a nucleotide sequence encoding the synthetic TF of the present invention. In some embodiments, a promoter capable of transcription is operably linked the nucleotide sequence encoding the synthetic TF. The present invention provides for a vector capable of stable maintenance in a host cell comprising the nucleic acid encoding the synthetic TF. In some embodiments, the vector is an expression vector. The present invention provides for a host cell comprising the vector capable of stable maintenance in a host cell comprising the nucleic acid encoding the synthetic TF.

The present invention provides for a synthetic system for modulating the expression of a gene of interest from a target promoter in response to a target ligand. The synthetic system comprises the synthetic TF of the present invention, or a nucleic acid encoding the synthetic TF, the gene of interest, optionally the target ligand, and the necessary components for transcription (and optionally translation) of the synthetic TF and/or the gene of interest. In some embodiments, the system is an in vitro or cell-free system. In some embodiments, the system is an in vivo system.

The present invention provides for a method for synthetic transcription factors (TFs), and their use and construction thereof. TFs are a class of proteins that regulate transcription of one or more gene by binding specific DNA specific sequences[1,2]. TFs have functionally and structurally distinct domains that perform various functions. Some of domains include, but are not limited to, ligand-binding domain (LBD), activation (AD), and DNA-binding domain (DBD). The LBD allows the TF to bind specific ligands, AD allows the TF to activate transcription by interacting with RNA polymerase, and DBD allows the TF to bind specific DNA sequences, which in turn effects transcription.

Although many TFs exist in nature, a TF to bind many ligands with biotech or medical application applications does not currently exist. The present invention provides for a method for assembling synthetic TFs that are not naturally occurring. This method enables the construction of biological sensors (biosensors, sensor modules) that have applications in metabolic engineering, gene therapy, drug delivery, stem cell engineering, anti-viral therapeutics, and the like[3,4]. A sensor module is defined as having a target ligand, a TF that binds the target ligand, and a promoter regulated by the TF.

The present invention provides for a synthetic TF comprising 3 parts: (1) a protein or protein domain (such as LBD from a naturally occurring TF) that binds a target ligand, (2) an AD or DBD, and (3) a DNA sequence that fuses part (1) to part (2). A schematic of the synthetic TF is provided in FIG. 1. One requirement of the design is that a conformational change results from the binding of part (1) to the target ligand such that the synthetic TF can exist in at least two different conformational states, one of which activates transcription from a promoter. This specification describes the construction of four different synthetic TFs for regulating two different promoters based on changing isoprenoid concentrations in bacteria and yeast.

The AraC protein regulates expression of arabinose utilization genes from the promoter $P_{BAD}$ by preferentially binding different DNA sequences in the presence and absence of arabinose[5]. AraC has a distinct ligand-binding domain (LBD) and DNA-binding domain (DBD), and changes its ability to activate $P_{BAD}$ depending on whether the LBD is arabinose bound. In some embodiments of the invention, synthetic TFs for isoprenoids are constructed by replacing AraC's LBD with proteins demonstrating isoprenoid binding activities, and engineered a synthetic *E. coli* TF (chimeric protein IA,) to respond to isopentenyl-diphosphate (IPP), the central intermediate for all isoprenoid biosynthesis[6], by fusing AraC's DBD with IPP isomerase enzyme (idi)[7] as the LBD. Idi was selected, because crystallographic data suggests it dimerizes upon binding IPP[8], and such LBD dimerization should create at least two different conformational states for IA, only one of which should activate transcription. Therefore, the bacterial synthetic TF IA, consisted of idi as Part (1), AraC's DBD as Part (2), and AraC's linker as Part (3).

Figure 2:
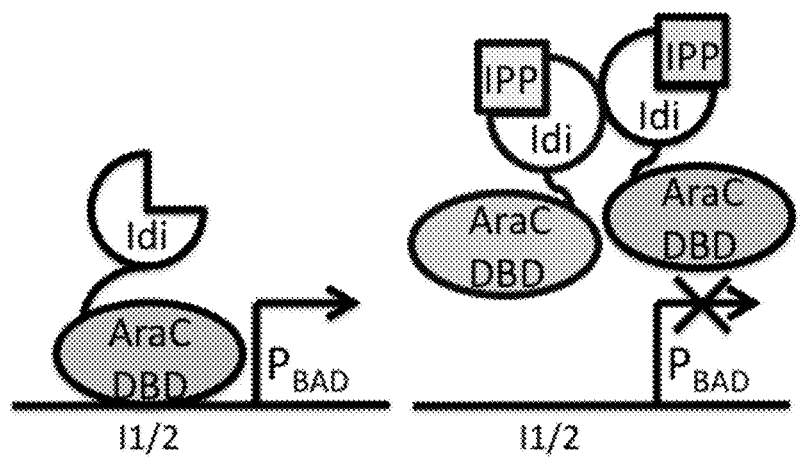
FIG. 2. Sensor module with chimeric protein IA consisting of Idi as Part1 AraC's DNA-binding domain as Part2, and AraC's linker sequence as Part3. One model for how IA regulates $P_{BAD}$ is IA binds the DNA sequence $I_1I_2$, activating transcription from $P_{BAD}$ in the absence of IPP (left), and IPP-bound IA dimerizes, preventing activation of $P_{BAD}$ (right).
Figure 3:
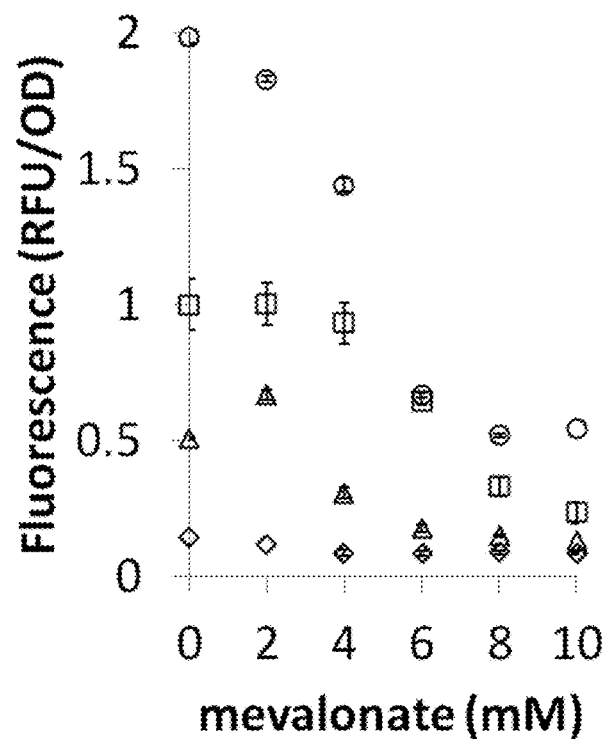
FIG. 3. Output of four sensor modules each with a different IA variant to changing IPP concentrations in E. coli HC175 monitored with mcherry. Diamonds represent AC, triangles IA32, squares IA, and circles IA44.

IA is tested as part of a sensor module that consisted of IPP, IA, and $P_{BAD}$ (FIG. 2) in *Escherichia coli* (*E. coli*) HC175, a variant of *E. coli* MG1655 capable of converting mevalonate to IPP, monitoring the output of the sensor module with the fluorescent protein Mcherry. Feeding HC175 different concentrations of mevalonate in the presence of IA changed fluorescence, but no change in fluorescence was observed in the presence of only AraC's DBD (AC) (FIG. 3). Therefore, it is concluded that IA can regulate $P_{BAD}$ according to changing IPP concentrations. Variants of IA are constructed to demonstrate how transcriptional activity could be tuned for different applications, especially medicinal ones where tight regulation is necessary. IA is modified using error-prone PCR and isolated two mutants: IA32 showed half the output level, while IA44 showed twice the output level of IA (FIG. 3).

Figure 4:
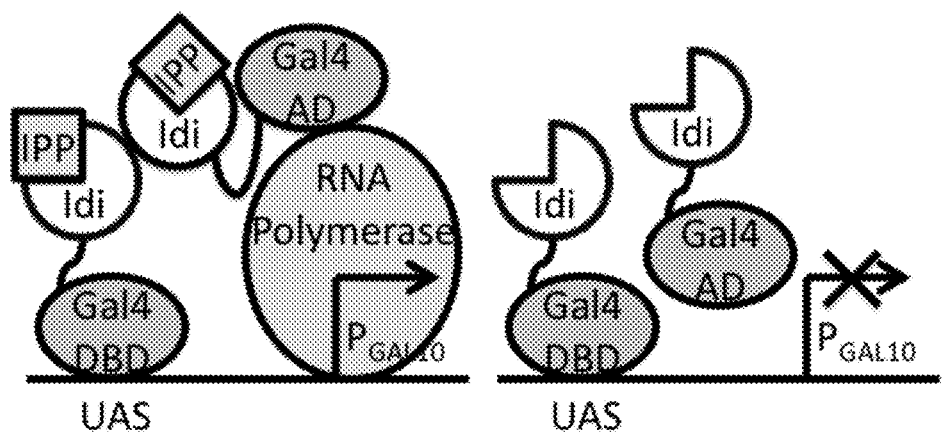
FIG. 4. Sensor module for detecting IPP in S. cerevisiae. The synthetic TF is a chimeric protein of Idi as Part1 and either Gal4's AD or DBD as Part2. Part3 is a synthetic DNA sequence we designed to fuse Part1 and Part2 together. One model for $P_{GAL10}$ regulation is Idi dimerizes when IPP bound, bringing the upstream activation sequence (UAS) bound Gal4 DBD in close enough proximity with the Gal4 AD to activate transcription (left). In the absence of dimerization at the LBD, there is no transcription from $P_{GAL10}$ (right).
Figure 5:
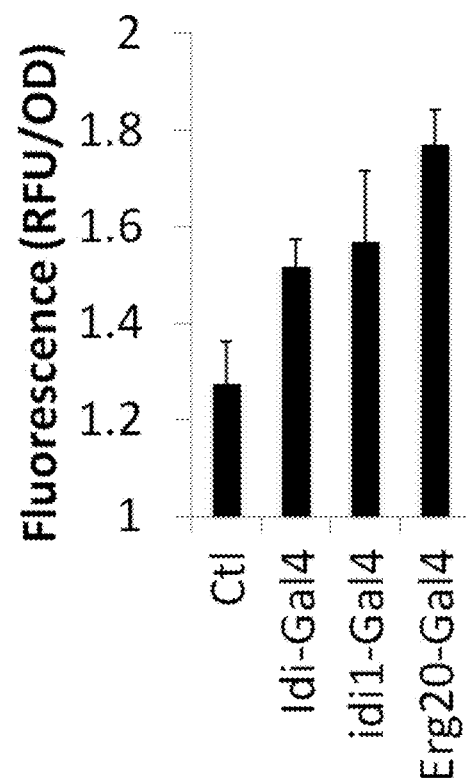
FIG. 5. Output of three sensor modules for IPP with synthetic TFs and $P_{GAL10}$ in S. cerevisiae is monitored with yEcitrine. The synthetic TFs consisted of Idi, Idi1, or Erg20 as the LBD fused to either Gal4's AD or DBD. "Ctl" is the control synthetic TFs. The sensor modules were tested in S. cerevisiae MO219.

This method for assembling synthetic TFs can be generalized to other organisms. A synthetic TF is constructed for isoprenoids in *Saccharomyces cerevisiae* (*S. cerevisiae*). The Gal4 protein regulates expression of GAL genes in response to galactose[9]. Similar to AraC, the functional domains of Gal4 are structurally distinct, consisting of an activator domain (AD) and DBD[10]. Idi is used as the LBD (Part (1)) and fused it to Gal4's AD and DBD (Part (2)s), as Idi dimerization should bring the AD and DBD in close enough proximity to activate transcription from a GAL promoter (e.g., $P_{GAL10}$). A synthetic DNA for Part (3) is designed. This synthetic TF is tested in a sensor module (FIG. 4) consisting of IPP, synthetic TF, and the promoter $P_{GAL10}$, and output from the sensor module is monitored with the fluorescent protein YEcitrine in *S. cerevisiae* MO219, a genetically modified strain that increases isoprenoid production when induced with galactose[11]. A change in fluorescence greater than baseline is observed after galactose induction (FIG. 5). Two additional yeast TFs were constructed from proteins known to bind IPP (Idi1[12] and Erg20[13]) as Part (1)s in place of Idi, and both showed even greater changes in fluorescence following induction. Combined with IA, these Gal4-based TFs highlight our design's modularity in assembling synthetic TFs.

References cited in the paragraphs above under "Method for Constructing Synthetic Transcription Factors":

[1] Price, M. N., Dehal, P. S. & Arkin, A. P., Orthologous Transcription Factors in Bacteria Have Different Functions and Regulate Different Genes, *PLoS Computation Biology* 3, 1739-1750 (2007).

[2] Farnham, P. J., Insights from genomic profiling of transcription factors, *Nature Reviews Genetics* 10, 605-616 (2009).

[3] Young, R. A., Control of the Embryonic Stem Cell State, *Cell* 144, 940-954 (2011).

[4] Rider, T. H., et al., Broad-Spectrum Antiviral Therapeutics, *PLos ONE* 6, e22572 (2011).

[5] Soisson, S. M., et al., Structural Basis for Ligand-Regulated Oligomerization of AraC, *Science* 276, 421-425 (1997).

[6] Lange, B., et al., Isoprenoid biosynthesis: The evolution of two ancient and distinct pathways across genomes, *PNAS* 97, 13172-13177 (2000).

[7] Hahn, F. M., Hurlburt, A. P. & Poulter, C. D., *Escherichia coli* Open Reading Frame 696 Is idi, a Nonessential Gene Encoding Isopentenyl Diphosphate Isomerase, *J. Bacteriology* 181, 4499-4504 (1999).

[8] De Ruyck, J., Oudjama, Y. & Wouters, J, Monoclinic form of isopentenyl diphosphate isomerase: a case of polymorphism in biomolecular crystals *Acta. Cryst* F64, 239-242 (2008).

[9] Traven, A., Jelicic, B. & Sopta, M, Yeast Gal4: a transcriptional paradigm revisited, *EMBO* 7, 496-499 (2006).

[10] Fields, S. & Song, O.-k., A novel genetic system to detect protein-protein interactions, *Nature* 340, 245-246 (1989).

[11] Ro, D.-K., et al., Production of the antimalarial drug precursor artemisinic acid in engineered yeast, *Nature* 440, 940-943 (2006).

[12] Mayer, M. P., et al., Disruption and maping of IDI, the gene for isopentenyl diphosphate isomerase in *Saccharomyces cerevisiae*, *Yeast* 8, 743-748 (1992).

[13] Fischer, M. J. C., et at, Metabolic Engineering of Monoterpene Synthesis in Yeast, *Biotechnology and Bioengineering* 108, 1883-1892 (2011).

Feedback-Regulated Evolution of Phenotype (FREP)

The present invention provide for a system for modulating the mutagenesis frequency of a host cell. The host cell has a mutator rate (R) which is inversely proportional to a phenotypic trait (P). The host cell comprises a sensor module and a mutator module. The sensor module comprises a target ligand, a TF (such as a synthetic TF) that binds the target ligand, and a target promoter regulated by the TF. The mutator module comprises the target promoter operably linked to a gene that increases mutation rate (mutator or mutator gene) of the host cell. The system comprises a host cell comprising a synthetic TF, a target DNA which the binding thereof modulates the expression of the gene that increases mutation rate of the host cell. The target promoter is heterologous to the gene that increases mutation rate.

The present invention provides for a nucleic acid encoding a target promoter operably linked to a gene that can increases mutation rate (mutator or mutator gene), such as one of the mutator genes described in Table 4, wherein the target promoter has one or more activator or repressor sites to which an activated TF (or synthetic TF) can bind, and the target promoter is heterologous to the gene that increases mutation rate.

In some embodiments, the target ligand is a desired product that the host cells produces. Such a host cell can be used to select for a mutated host cell that is increased or maximally increased or optimized for its production of the desired product.

The present invention provides for a feedback-regulated evolution of phenotype (FREP), a synthetic algorithm programming cells to increase or decrease mutagenesis depending on the level of a particular trait. One use of FREP is to evolve novel traits, which would enable engineering of behaviors at the microscopic (e.g., replication, differentiation) and macroscopic (e.g., flocking, amoeba aggregation) scales observed in nature, as well as novel behaviors (e.g., increased biomass degradation, metabolism of novel carbon sources, increased tolerance towards specific compounds, increased production of target chemicals).

Figure 6:
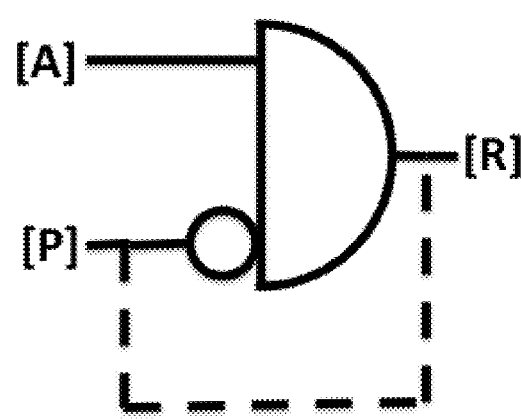
FIG. 6. Logic gate representation of synthetic algorithm illustrating P and R are inversely related, and a feedback loop (dotted line) from R to P shows R can affect P.

The algorithm accepts attenuation (A) and phenotypic diversity related to the target trait (P) as inputs, and outputs a mutation rate (R) (FIG. 6). The logic table for FREP is described in FIG. 7. Our algorithm dictates P and R be inversely related, because enhanced mutagenesis facilitates adaptation only when phenotypic diversity is low. R indirectly affects P over time as beneficial mutations appear, creating a feedback loop. A is a constraint on the maximum mutation rate and tunes P's effect on R. We implemented the novel algorithm as two modules (FIG. 8). The sensor module acts directly on the inputs and outputs a transcriptional level, which the mutator module converts into a mutation rate. The sensor module consists of three components: a ligand associated with P, a transcription factor (TF) that binds the target ligand, and a promoter regulated by the TF. Therefore, A constrains the strength and dynamics of the transcriptional output from the sensor module. The mutator module is composed of a gene that increases mutation rates (mutator).

Figure 9:
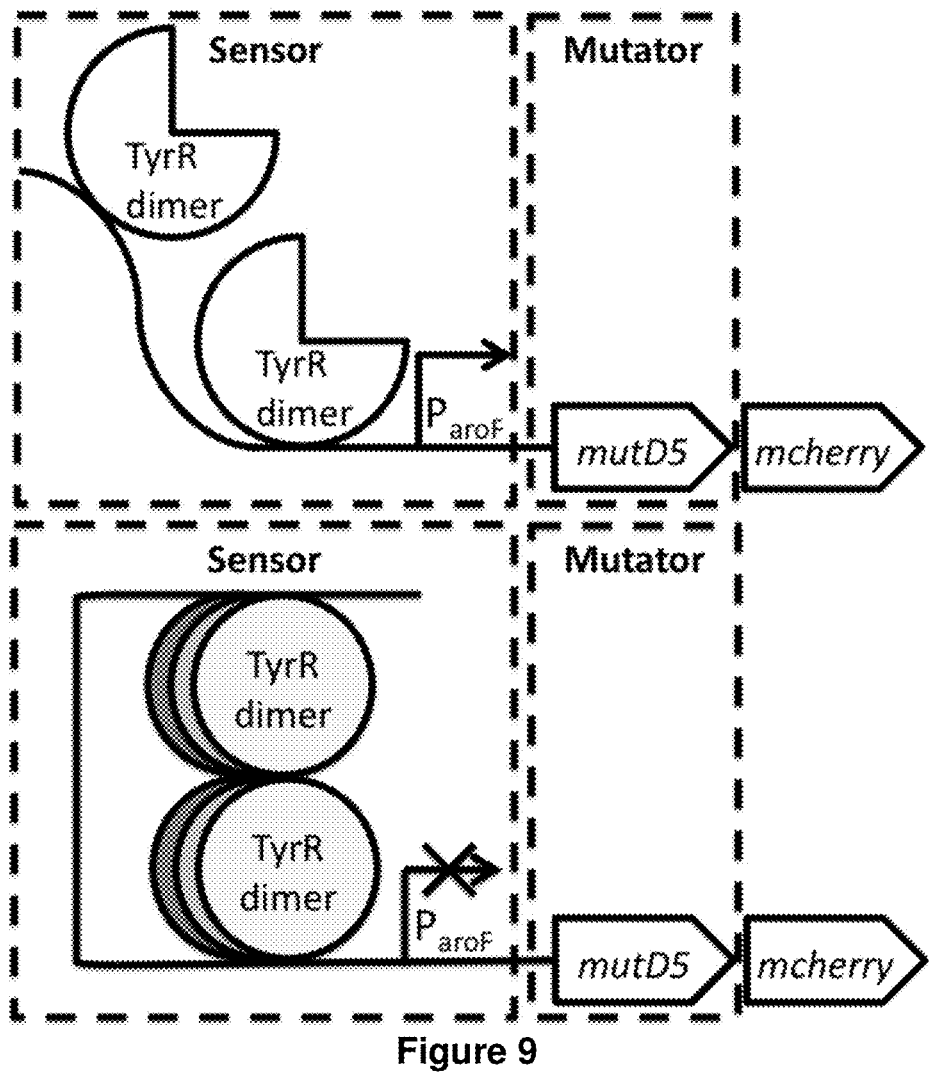
FIG. 9. FREP implemented with sensor module $P_{aroF3}$ and mutator module mutD5. $P_{aroF3}$ consists of tyrosine, modified TyrR, and modified $P_{aroF}$; the mutator module consists of mutD5. TyrR dimers activate transcription from $P_{aroF}$ in the absence of tyrosine (top), and tyrosine-bound TyrR form hexamers that dimerize to repress transcription from $P_{aroF}$ (bottom).
Figure 10:
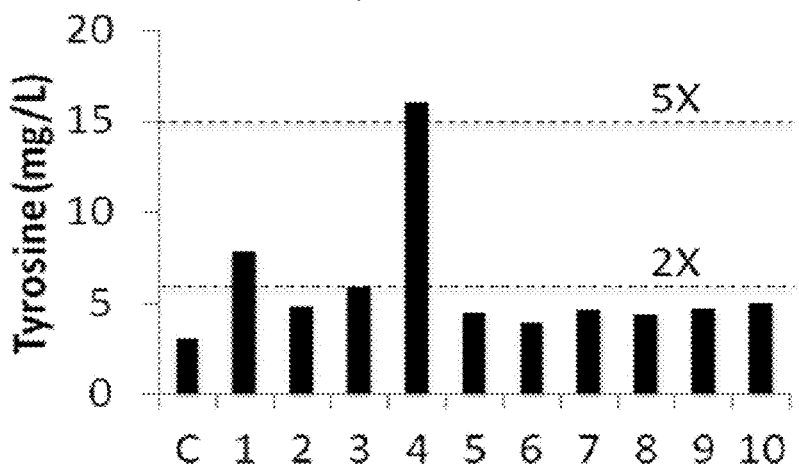
FIG. 10. Tyrosine production from ten mutants evolved with FREP showing the lowest fluorescence after 24 hours. C is the control not evolved with FREP.

As a proof-of-concept, we implemented FREP to increase production of the industrially-important amino acid tyrosine in *Escherichia coli* (*E. coli*) using the tyrosine-responsive TF TyrR[1] to regulate expression of the mutator mutD5[2]. In this implementation, FREP should raise R to increase P when tyrosine concentration is low, and slow R as beneficial mutations increasing tyrosine production appear. We tested FREP implemented with $S_{aroF3}$ for the sensor module and mutD5 for the mutator module in *E. coli* DJ238, expressing mcherry bicistronically with mutD5 to report relative mutator levels in the cell (FIG. 9), and isolated ten colonies with the lowest fluorescence after 24 hours. All ten mutants demonstrated increased tyrosine production, and one exhibited greater than five-fold increase compared to the starting strain (FIG. 10).

Figure 11:
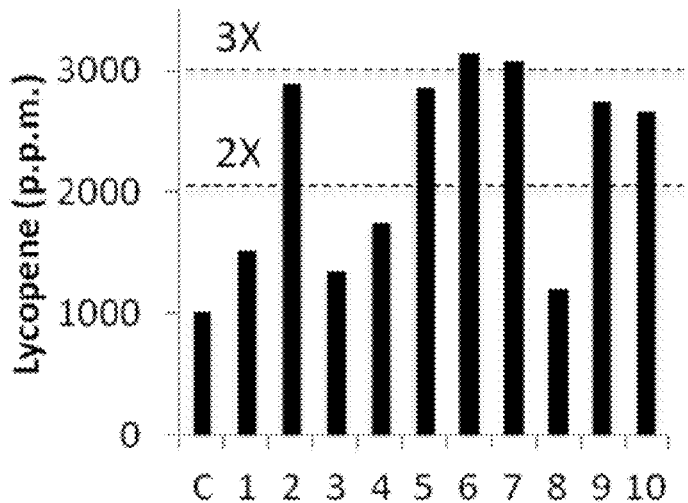
FIG. 11. Ten mutants showing the lowest fluorescence after 24 hours of FREP with mutD5 controlled by IA44 were transformed with pLyc, and lycopene production was quantified. C is the control that did not undergo FREP. Lycopene production is presented as p.p.m. (ug/g dry cell weight).

To determine whether FREP could evolve other traits, we implemented the algorithm to increase production of isoprenoids, a class of compounds with a wide range of industrial applications as drugs[3] and biofuels[4], to name a few. We constructed a sensor module with IPP, the synthetic transcription factor IA44 (Example 1), and $P_{BAD}$. We tested FREP implemented with IA44 for evolution of increased isoprenoid production in *E. coli* MG1655, and expressed mcherry bicistronically with the mutator module to monitor relative mutator levels. Ten colonies with the lowest fluorescence after 24 hours were made electrocompetent and transformed with a plasmid containing the lycopene synthase genes (pLyc). Lycopene measured from a random transformant for all ten colonies was higher than the control not modified with FREP. Six colonies had mutants producing on average 2900 μg/g dry cell weight. (p.p.m.) of lycopene, whereas the control produced only 1000 p.p.m. (FIG. 11).

Figure 12:
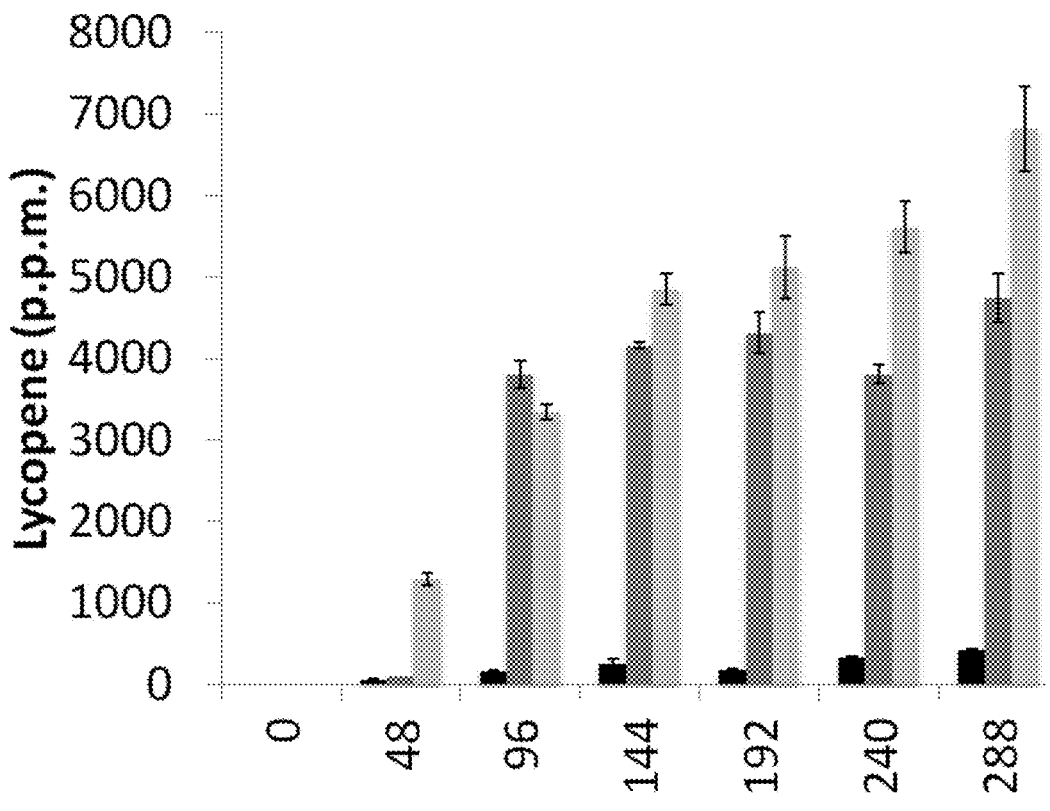
FIG. 12. Lycopene production sampled every 48 hours from E. coli MG1655 expressing pLyc, sensor module, and mutator module over 288 hours. The transcription factors used in the sensor module were AraC (black bars), IA32 (dark gray bars), or IA44 (light gray bars). Lycopene production is presented as p.p.m. (ug/g dry cell weight). Sensor modules with AraC were induced with 10 mM arabinose.
Figure 13:
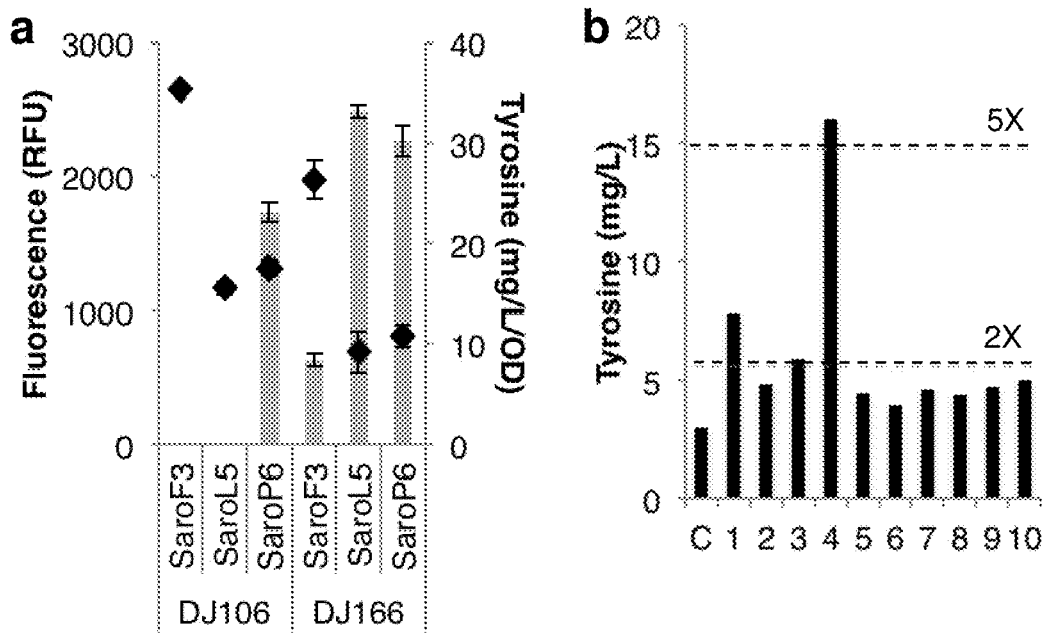
FIG. 13. FREP design. (a) FREP implementation of the variable mutation strategy using an adaptive control system. The sensor controls the change in transcriptional level (ΔT) in the system. The actuator converts the transcriptional level (T) into a mutation rate (M) that modifies the genome to produce the target phenotype gauged by L. As L increases, the sensor increases ΔT, which causes the actuator to decrease M. (b) Two different outcomes of FREP are possible depending on whether the ligand is permeable to the cell membrane. Circles represent the concentration of ligand in the cell. If the ligand is permeable to the membrane, then a few or a single, high-level producer of L could reduce M in all other cells, causing the entire population to stop evolving independent of each cell's level of L (top). If the ligand is not permeable to the membrane, then each cell in the population evolves independently of the other cells (bottom).
Figure 14:
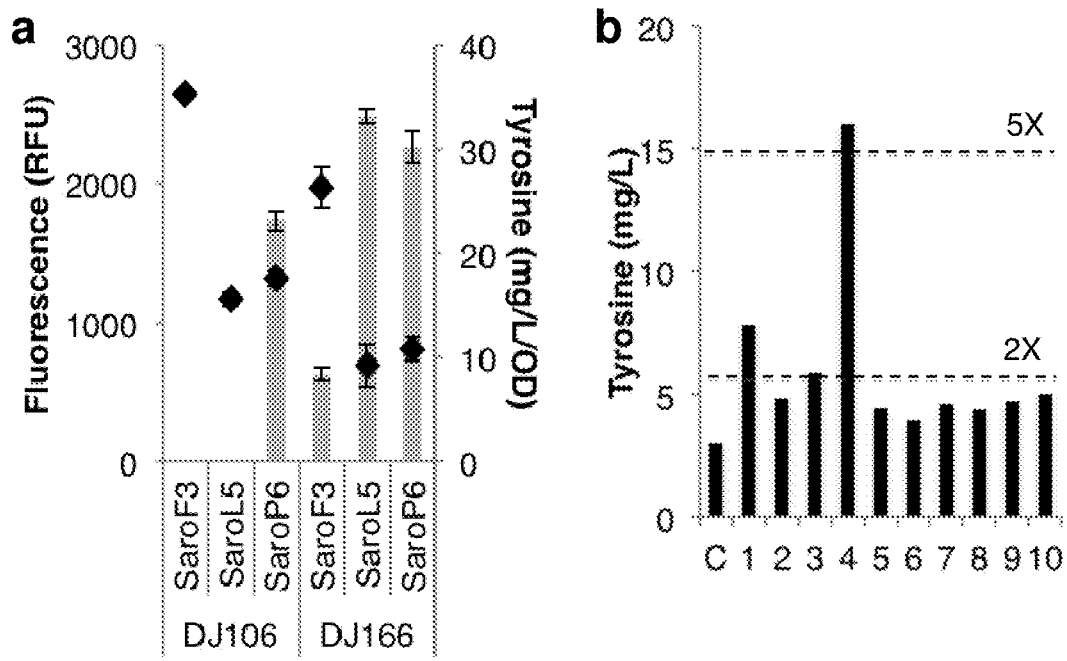
FIG. 14. FREP evolves increased tyrosine production. (a) Out of twenty sensors tested, the most sensitive sensors for each promoter ($P_{aroF}$, $P_{aroL}$, $P_{aroP}$) are compared for sensitivity to changes in tyrosine concentration in vivo. Bars represent tyrosine production and ♦ represent relative fluorescence units normalized to OD measured at 600 nm DJ106 and DJ166 are variants of E. coli BLR, and DJ166 produces more tyrosine than DJ106. (b) Tyrosine production from ten mutants evolved with FREP showing the lowest fluorescence after 24 hours. C is the control not evolved with FREP.
Figure 15:
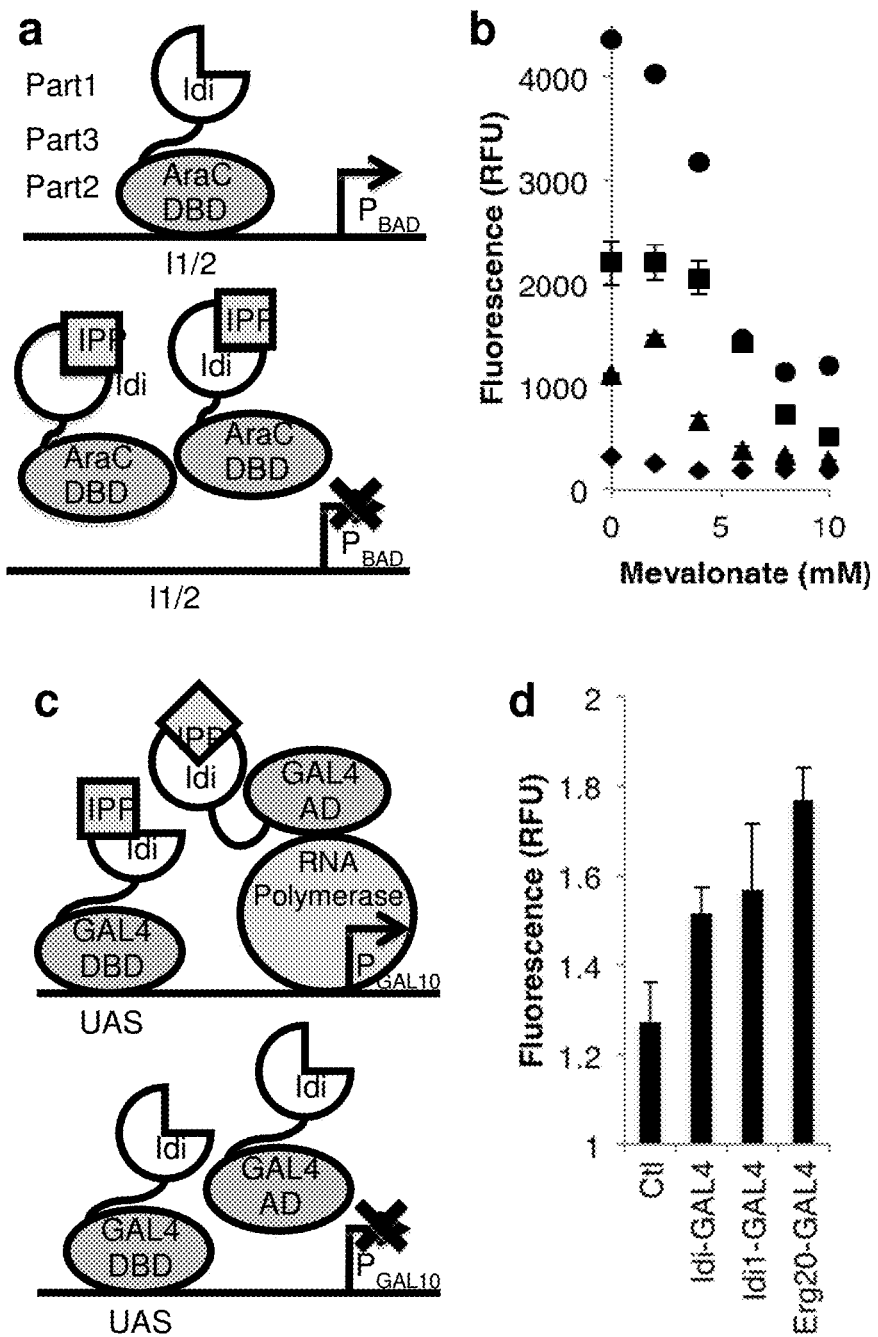
FIG. 15. Synthetic transcription factors (TFs) respond to IPP. (a) A synthetic TF consists of 3 parts: Part1 binds the target ligand, Part2 converts the binding signal into a change in RNA polymerase binding to the target promoter, and Part3 is an amino acid linker fusing Part1 and Part2 together. Here, a sensor with synthetic TF IA comprised of Idi as Part1 and AraC's DBD and linker as Part2 and Part3, respectively. One model for how IA regulates $P_{BAD}$ is IA binds the DNA sequence $I_1I_2$, activating transcription from $P_{BAD}$ in the absence of IPP (top), and IPP-bound IA dimerizes, preventing binding to $I_1I_2$ and activation of $P_{BAD}$ (bottom). (b) Output of four sensors, each with a different TF, to changing IPP concentrations in E. coli HC175 monitored with mcherry. ♦ represent AC, ▲ IA32, ■ IA, and ● IA44. (c) A sensor for detecting IPP in S. cerevisiae. The synthetic TF consists of Idi as Part1, GAL4's AD and DBD as Part2, and a 19-amino acid linker as Part3. One model for $P_{GAL10}$ regulation is that Idi dimerizes when bound to IPP, bringing the upstream activation sequence (UAS)-bound GAL4 DBD in close enough proximity with the GAL4 AD to activate transcription (top). In the absence of Part1 dimerization, there is no transcription from $P_{GAL10}$ (bottom). (d) $P_{GAL10}$ output from three sensors with synthetic TFs in S. cerevisiae MO219 induced with galactose. The synthetic TFs consist of Idi, Idi1, or Erg20 as Part1 fused to GAL4's AD and DBD. "Ctl" is the control without synthetic TFs. Output was monitored with the fluorescent protein yEcitrine and normalized to fluorescence in the absence of galactose.
Figure 16:
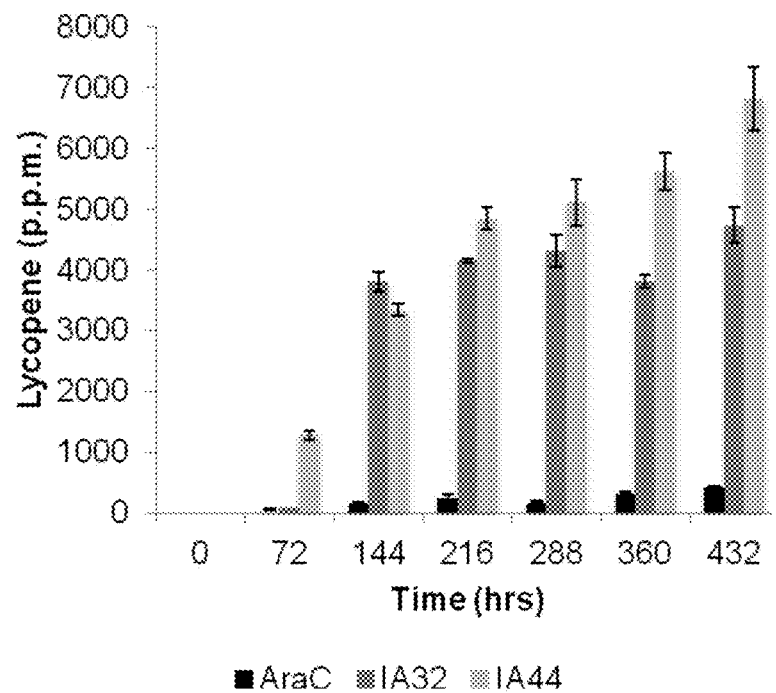
FIG. 16. FREP evolves increased IPP production. Lycopene production sampled every 72 hours over a 432-hour period from E. coli MG1655 expressing pLyc, an IPP sensor, and an actuator. The transcription factors used in the sensor were AraC (black bars), IA32 (dark gray bars), or IA44 (light gray bars). Lycopene production is presented as p.p.m. (ug/g dry cell weight). The sensor with AraC was induced with 10 mM arabinose.

Finally, we examined FREP in a long-term experiment by co-transforming pLyc with IPP sensor and mutD5 mutator modules into *E. coli* MG1655, and monitoring lycopene production over 288 hours. We quantified lycopene production every 48 hours from ten random colonies and only passaged the colony demonstrating the highest production. After 288 hours, lycopene production increased to 6800 p.p.m. using IA44, 4700 p.p.m. using IA32, and only 400 p.p.m. using AraC (FIG. 12). A control implemented with IA44 without a mutator module produced 0 p.p.m.

We successfully demonstrated the design and implementation of a synthetic algorithm programming cells to evolve new traits by deciding whether to increase or decrease mutagenesis. Unlike existing methods to engineer metabolism[5,6], FREP does not require a priori knowledge about the genetics of the trait being evolved. Distinct from directed evolution approaches requiring phenotype-specific high-throughput screens or selections to identify high-performing mutants, FREP isolated mutants producing more tyrosine and IPP by monitoring the algorithm's output with a fluorescent protein. Our work provides a foundation for assembling intelligent synthetic biological systems capable of making decisions by incorporating real-time information about itself and its environment.

References cited in the paragraphs above under "Feedback-Regulated Evolution of Phenotype (FREP)":
1. Pittard, J., Camakaris, H. & Yang, J., The TyrR regulon, *Molecular Microbiology* 55, 16-26 (2005).
2. Schaaper, R. M., Mechanisms of mutagenesis in the *Escherichia coli* mutator mutD5: Role of DNA mismatch repair, *Proc. Natl. Acad. Sci. USA* 85, 8126-8130 (1988).
3. Chang, M. C. Y. & Keasling, J. D., Production of isoprenoid pharmaceuticals by engineered microbes, *Nature Chemical Biology* 2, 674-681 (2006).
4. Keasling, J. D. & Chou, H., Metabolic engineering delivers next-generation biofuels, *Nature Biotechnology* 26, 298-299 (2008).
5. Alper, H., Miyaoku, K. & Stephanopoulos, G., Construction of lycopene-overproducing *E. coli* strains by combining systematic and combinatorial gene knockout targets, *Nature Biotechnology* 23, 612-616 (2005).
6. Wang, H. H., et al., Programming cells by multiplex genome engineering and accelerated evolution, *Nature* 460, 894-899 (2009).

Suitable mutator genes are provided herein in Table 4.

TABLE 4

| Organism | Mutator Gene | Reference |
|---|---|---|
| *Escherichia coli* | mutD5 | J.-P. Horst et al., *Escherichia coli* mutator genes, Trends in Microbiology 7: 29-36 (1999) |
| *Bacillus subtilis* | mutM | M. Sasaki et al., Genetic analysis of *Bacillus subtilis* mutator genes, J. Gen. Appl. Microbiol. 46: 183-187 (2000) |
| *Pseudomonas aeruginosa* | mutS, mutL | I. Wiegand et al., Mutator genes giving rise to decreased antibiotic susceptibility in *Pseudomonas aeruginosa*, Antimicrobial Agents and Chemotherapy 52: 3810-3813 (2008) |
| *Synechococcus* sp. | mutS | D. Emlyn-Jones et al., Nitrogen-regulated hypermutator strain of *Synechococcus* sp. for use in in vivo artificial evolution, Appl Environ Microbiol 69: 6427-6433 (2003) |
| *Saccharomyces cerevisiae* | msh2 | K. Drotschmann et al., Mutator phenotypes of yeast strains heterozygous for mutations in the MSH2 gene, PNAS 96: 2970-2975 (1999) |
| *Saccharomyces cerevisiae* | him1 | E. P. Kelberg, HIM1, a new yeast *Saccharomyces cerevisiae* gene playing a role in control of spontaneous and induced mutagenesis, Mutat. Res. 578: 64-78 (2005) |

Proteins, and Nucleic Acids Encoding Thereof

All peptides and proteins described in this specification also include homologous peptides and proteins that has a polypeptide sequence that is at least 70%, 75%, 80%, 85%, 90%, 95% or 99% identical to any one of the peptides and proteins described in this specification or in an incorporated reference. The homologous peptides and proteins retain amino acids residues that are recognized as conserved for the peptides and proteins for a biological function. The homologous peptides and proteins may have non-conserved amino acid residues replaced or found to be of a different amino acid, or amino acid(s) inserted or deleted, but which does not affect or has insignificant effect on the biological activity of the homologous peptides and proteins. Each homologous peptide or protein has a biological activity that is identical or essentially identical to the biological activity any one of the peptide or protein described in this specification or in an incorporated reference. The homologous peptides and proteins may be found in nature or be an engineered mutant thereof.

The nucleic acid constructs of the present invention comprise nucleic acid sequences encoding one or more of the subject peptides and proteins. The nucleic acid of the subject peptides and proteins are operably linked to promoters and optionally control sequences such that the subject peptides and proteins are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject peptides and proteins are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject peptides and proteins can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of aromatic amino acid ensured. When added, the intermediate is present in an excess amount in the culture medium.

Host Cells

The host cells of the present invention are genetically modified in that heterologous nucleic acid have been introduced into the host cells, and as such the genetically modified host cells do not occur in nature. The suitable host cell is one capable of expressing any nucleic acid construct encoding one or more peptides and proteins described herein.

Any prokaryotic or eukaryotic host cell may be used in the present method so long as it remains viable after being transformed with a sequence of nucleic acids. Generally, although not necessarily, the host microorganism is bacterial. Examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus* taxonomical classes. Suitable eukaryotic cells include, but are not limited to, fungal, insect or mammalian cells. Suitable fungal cells are yeast cells, such as yeast cells of the *Saccharomyces* and *Candida* genera.

REFERENCES CITED

1. Elena, S. F., Cooper, V. S. & Lenski, R. E., Punctuated Evolution Caused by Selection of Rare Beneficial Mutations, *Science* 272, 1802-1804 (1996).
2. Desai, M. M. & Fisher, D. S., The Balance Between Mutator and Nonmutators in Asexual Populations, *Genetics* 188, 997-1014 (2011).
3. Barrick, J. E., et al., Genome evolution and adaptation in a long-term experiment with *Escherichia coli, Nature* 461, 1243-1247 (2009).
4. Sniegowski, P. D., Gerrish, P. J. & Lenski, R. E., Evolution of high mutation rates in experimental populations of *E. coli, Nature* 387, 703-705 (1997).
5. Stich, M., Manrubia, S. C. & Lázaro, E., Variable Mutation Rates as an Adaptive Strategy in Replicator Populations, *PLoS ONE* 5: e11186 (2010).
6. Giruad, A., et al., Costs and Benefits of High Mutation Rates: Adaptive Evolution of Bacteria in the Mouse Gut, *Science* 291, 2606-2608 (2001).
7. Loh, E., Salk, J. J. & Loeb, L. A. Optimization of DNA polymerase mutation rates during bacterial evolution, *PNAS* 107, 1154-1159 (2010).
8. Dietrich, J. A., McKee, A. E. & Keasling, J. D., High-Throughput Metabolic Engineering: Advances in Small-Molecule Screening and Selection, *Annual Review Biochemistry* 79, 563-590 (2010).
9. Kazlauskas, R. J. & Bornscheuer, U. T., Finding better protein engineering strategies, *Nature Chemical Biology* 5, 526-529 (2009).
10. Greener, A., Callahan, M. & Jerpseth, B., An efficient random mutagenesis technique using an *E. coli* mutator strain, *Mol. Biotechnol.* 7, 188-195 (1997).
11. Portnoy, V. A., Bezdan, D. & Zengler, K., Adaptive laboratory evolution—harnessing the power of biology for metabolic engineering, *Current Opinion in Biotechnology* 22, 590-594 (2011).
12. Astrom, K. J., Adaptive Feedback Control, *Proceedings of the IEEE* 75, 185-217 (1987).
13. Juminaga, D., et al., Modular Engineering of L-Tyrosine Production in *Escherichia coli, Applied and Environmental Microbiology* 78, 89-98 (2012).
14. Pittard, J., Camakaris, H. & Yang, J., The TyrR regulon, *Molecular Microbiology* 55, 16-26 (2005).
15. Schaaper, R. M., Mechanisms of mutagenesis in the *Escherichia coli* mutator mutD5: Role of DNA mismatch repair, *Proc. Natl. Acad. Sci. USA* 85, 8126-8130 (1988).
16. Chang, M. C. Y. & Keasling, J. D., Production of isoprenoid pharmaceuticals by engineered microbes, *Nature Chemical Biology* 2, 674-681 (2006).
17. Keasling, J. D. & Chou, H., Metabolic engineering delivers next-generation biofuels, *Nature Biotechnology* 26, 298-299 (2008).
18. Soisson, S. M., et al., Structural Basis for Ligand-Regulated Oligomerization of AraC, *Science* 276, 421-425 (1997).
19. Lange, B., et al., Isoprenoid biosynthesis: The evolution of two ancient and distinct pathways across genomes, *PNAS* 97, 13172-13177 (2000).
20. Hahn, F. M., Hurlburt, A. P. & Poulter, C. D., *Escherichia coli* Open Reading Frame 696 Is idi, a Nonessential Gene Encoding Isopentenyl Diphosphate Isomerase, *J. Bacteriology* 181, 4499-4504 (1999).
21. De Ruyck, J., Oudjama, Y. & Wouters, J., Monoclinic form of isopentenyl diphosphate isomerase: a case of polymorphism in biomolecular crystals, *Acta. Cryst. F*64, 239-242 (2008).

22. Hellman, L. M. & Fried, M. G., Electrophoretic mobility shift assay (EMSA) for detecting protein-nucleic acid interactions, *Nature Protocols* 2, 1849-1861 (2007).
23. Heyduk, T. & Heyduk, E., Molecular beacons for detecting DNA binding proteins, *Nature Biotechnology* 20, 171-176 (2002).
24. Traven, A., Jelicic, B. & Sopta, M., Yeast Gal4: a transcriptional paradigm revisited, *EMBO* 7, 496-499 (2006).
25. Fields, S. & Song, O.-k., A novel genetic system to detect protein-protein interactions, *Nature* 340, 245-246 (1989).
26. Robinson, C. R. & Sauer, R. T., Optimizing the stability of single-chain proteins by linker length and composition mutagenesis, *PNAS* 95, 5929-5934 (1998).
27. Ro, D.-K., et al., Production of the antimalarial drug precursor artemisinic acid in engineered yeast, *Nature* 440, 940-943 (2006).
28. Mayer, M. P., et al., Disruption and mapping of IDI, the gene for isopentenyl diphosphate isomerase in *Saccharomyces cerevisiae*, *Yeast* 8, 743-748 (1992).
29. Fischer, M. J. C., et al., Metabolic Engineering of Monoterpene Synthesis in Yeast, *Biotechnology and Bioengineering* 108, 1883-1892 (2011).
30. Rosche, W. A. & Foster, P. L., Determining Mutation Rates in Bacterial Populations, *Methods* 20, 4-17 (2000).
31. Alper, H., Miyaoku, K. & Stephanopoulos, G., Construction of lycopene-overproducing *E. coli* strains by combining systematic and combinatorial gene knockout targets, *Nature Biotechnology* 23, 612-616 (2005).
32. Wang, H. H., et al., Programming cells by multiplex genome engineering and accelerated evolution, *Nature* 460, 894-899 (2009).
33. Young, R. A., Control of the Embryonic Stem Cell State, *Cell* 144, 940-954 (2011).
34. Rider, T. H., et al., Broad-Spectrum Antiviral Therapeutics, *PLos ONE* 6, e22572 (2011).

Figure 29:
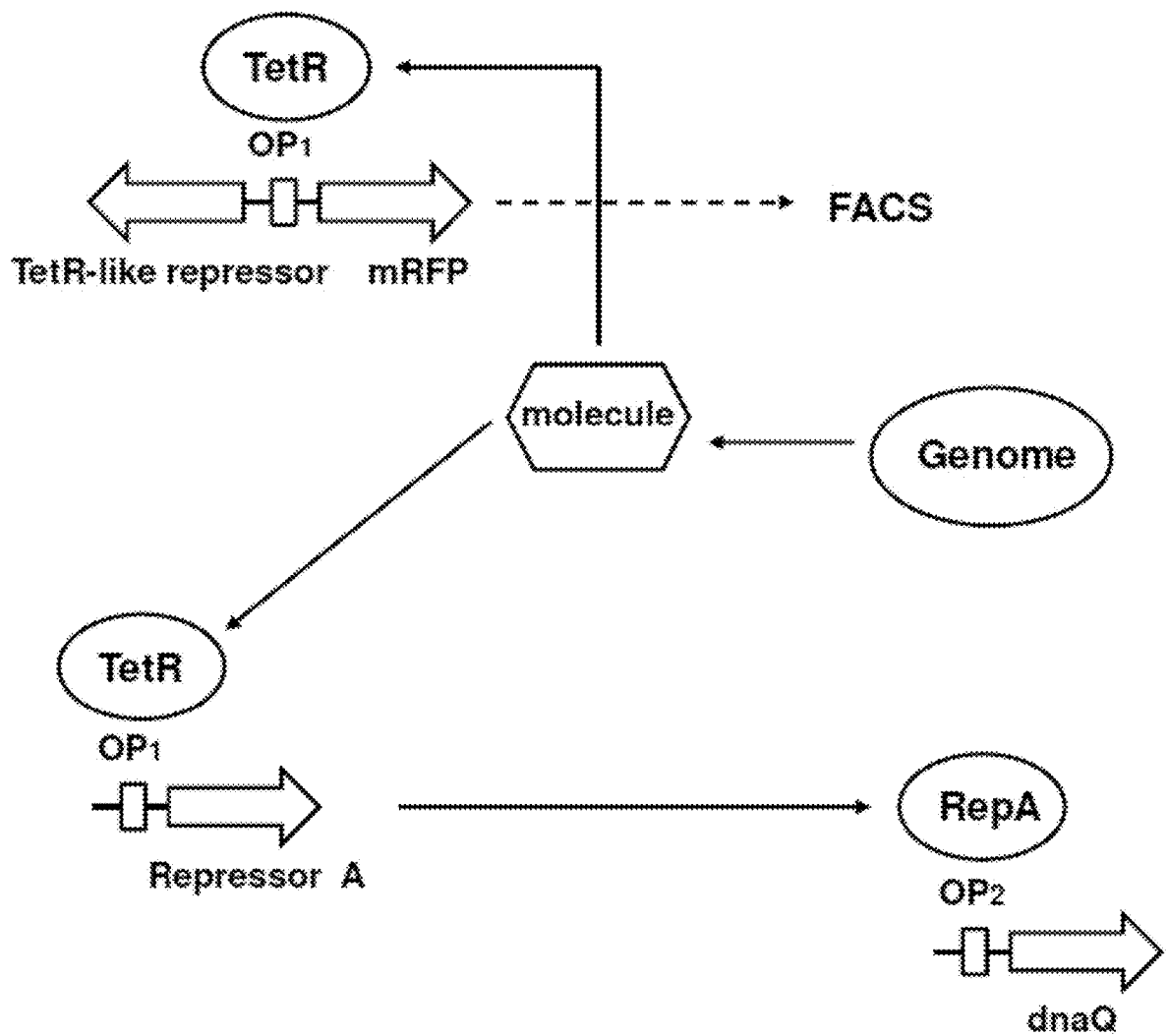
FIG. 29. A particular embodiment of the feedback-regulated forced evolution (FRFE).
Figure 30:
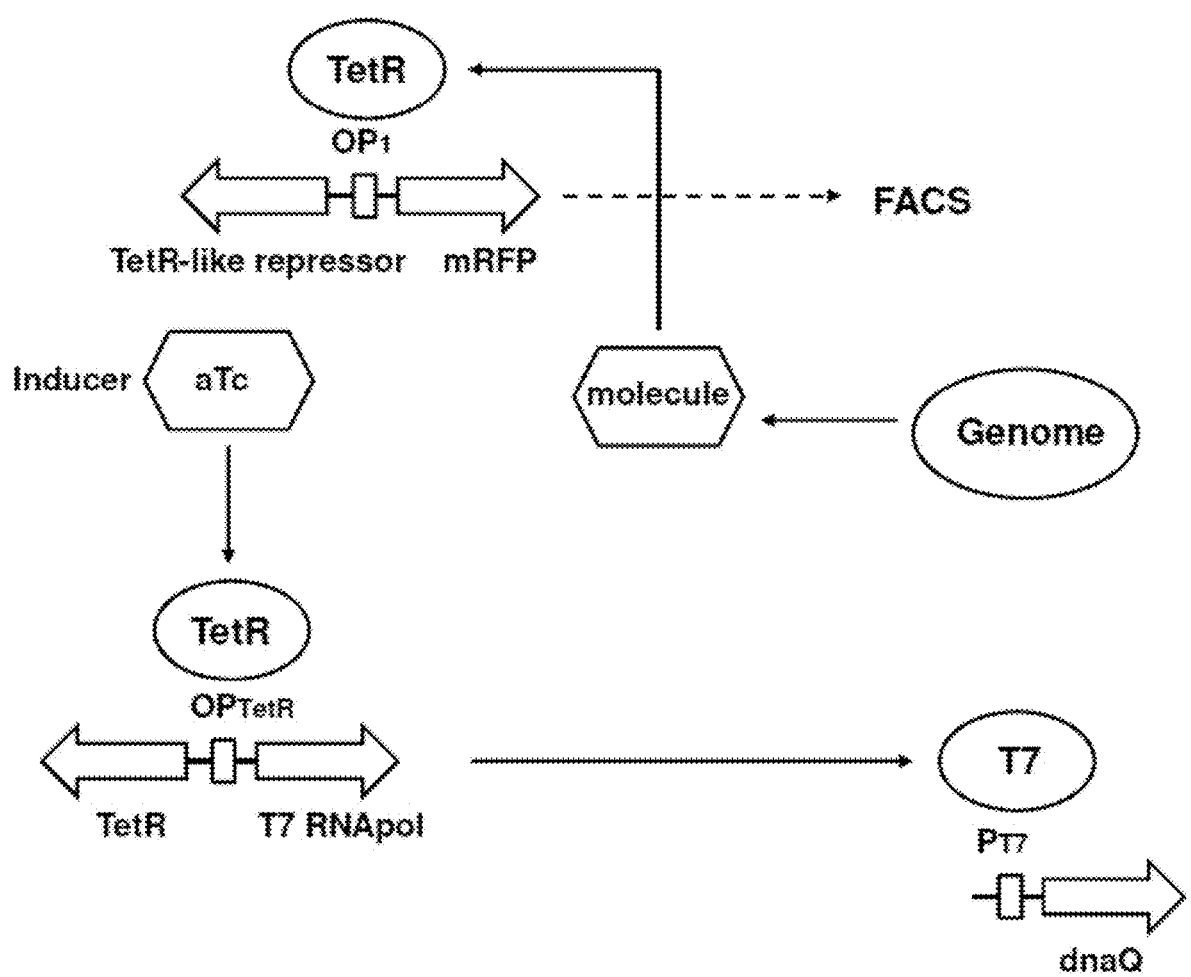
FIG. 30. A particular embodiment of the inducible forced evolution (IFE).

The present invention also provides for a system for triggering/increasing the expression of silent secondary metabolite biosynthesis gene clusters through the introduction of spontaneous genome mutations, which can lead to the production of target molecules. The system comprises one or more of the following components: an Actuator for generating mutations, a Controller for controlling the rate of mutation, and a Biosensor for detecting the synthesized target molecule. In some embodiments, the system is capable of feedback-regulated forced evolution (FRFE) or inducible forced evolution (IFE). Particular embodiments of each are shown in FIGS. 29 and 30. In some embodiments, the biosensor comprises a repressor, such as a $Tet^R$ repressor, which is commonly encoded by secondary metabolite gene clusters. The repressor binds the final products of the clusters-encoded biosynthetic machineries or their precursors, and typically de-represses expression of the genes for export of these compounds. The present invention also provides for a kit comprising the various components comprising standard parts for construction of the system (which can be codon-tuned) where task-specific parts can be easily modified by splicing the desired parts.

FIG. 29 shows a particular embodiment of the feedback-regulated forced evolution (FRFE). The Actuator is mutator gene dnaQ which is cloned under the control of a constitutive strong promoter with an upstream operator specific for Repressor A, such as LacI. The Controller is a Repressor A-coding gene that is under the control of another constitutive strong promoter that is controlled by an operator specific for a repressor, such as a $Tet^R$-like repressor, which is responsive for a cognate secondary metabolite (cluster-specific). The Controller-Sensor is a cluster-specific $Tet^R$-like repressor (from the target molecule gene cluster) and a reporter gene, such as monomeric red fluorescence protein (mRFP) genes, are under the control of constitutive promoters, but the reporter expression is controlled via a $Tet^R$-like repressor-responsive operator. As shown in the specific example of FIG. 29, DnaQ is constitutively expressed, causing an about 1000-fold increase in spontaneous genome mutations. Some mutations lead to increased production of the target molecule, which then binds to the cognate $Tet^R$-like repressor. The latter dissociates from the OP1 operators controlling expression of both mRFP and Repressor A. Consequently, the mRFP is expressed, allowing sorting of the cells and selection of overproducers of target molecules. At the same time, the expression of DnaQ is down-regulated due to the expression of Repressor A, this lowering the mutation rate. Cells expressing mRFP are sorted using any suitable means, such as Fluorescence-Assisted Cell sorting (FACS).

FIG. 30 shows a particular embodiment of the inducible forced evolution (IFE). The Actuator is mutator gene dnaQ which is cloned under the control of a promoter, such as a T7 promoter. with an upstream operator specific for Repressor A, such as LacI. The Controller is a T7 RNA polymerase-coding gene that is under the control of a constitutive promoter that is controlled by an operator specific for a repressor, such as a $Tet^R$-like repressor which is responsive to anhydrotetracycline (aTc). The Sensor is a cluster-specific $Tet^R$-like repressor (from the target molecule gene cluster) and a reporter gene, such as monomeric red fluorescence protein (mRFP) genes, are under the control of constitutive promoters, but the reporter expression is controlled via a $Tet^R$-like repressor-responsive operator. As shown in the specific example of FIG. 30, the addition of aTc induces expression of T7 RNA polymerase which in turn leads to expression of DnaQ. The latter causes an about 1000-fold increase in spontaneous genome mutations. Some mutations lead to increased production of a target molecule, which in turn binds to the cognate $Tet^R$-like repressor. The latter dissociates from the OP1 operator controlling expression of mRFP. Consequently, the mRFP is expressed, which allows for sorting of the cells and selection of overproducers of the target molecule. Cells expressing mRFP are sorted using any suitable means, such as Fluorescence-Assisted Cell sorting (FACS).

In both the FRFE and IFE systems, the mRFP gene can be replaced with an antibiotic resistance gene to allow for direct selection of cells where expression of the antibiotic resistance gene is increased. However this would also depend on the phenotype of the strain in question. For example, many streptomycetyes are resistance to multiple antibiotics, and it may be difficult to select such strains with an appropriate marker.

The present invention can be used to activate expression of silent gene clusters containing certain types of regulators, thereby triggering/increasing production of potentially novel secondary metabolites. The latter may be useful in drug discovery, and parts of activated biosynthetic pathways may be utilized for biological production of both new and known chemicals that are currently produced from fossil fuel, such as petroleum.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Method for Constructing Synthetic Transcription Factors

Materials and Methods
Oligonucleotides and DNA Sequencing.

All oligonucleotides were obtained from Integrated DNA Technologies with standard purification. Restriction sites are underlined and start codons are in italics in the primer sequences unless otherwise indicated. DNA sequencing to confirm cloning products were performed by Quintara Biosciences.

Strains.

EcDJ106 (BLR *E. coli* ΔtyrR), EcDJ166 (BLR *E. coli* ΔtyrR ΔpheA/L aroF[P124L] tyrA[M53I; A354V]), and EcDJ238 (MG1655 *E. coli* ΔtyrR) were gifts from Dr. Darmawi Juminaga. All genes and promoter sequences amplified from the *E. coli* chromosome were from the strain MG1655.

Construction of pLyc.

crtE, crtI, and crtB were cloned from pT-LYCm4 (gift from Dr. Adrienne McKee) into pBAD18-Cm using SpeI and HindIII, and following standard restriction digest and ligation cloning protocol.

Construction of IPP Sensor Modules.

See Materials and Methods for Example 4.

Construction of tyrR Sensor Module.

$P_C$ was replaced with CP20 (Jensen, P. D. & Hammer, K., The Sequence of Spacers between the Consensus Sequences Modulates the Strength of Prokaryotic Promoters. *Applied and Environmental Microbiology* 64, 82-87 (1998)) in pCtl-RFP-AraC with the primers 5'-ggccgctagc catgggtgagtttat-tcttgacagtgcggccgg gggctgatatcatagcagagtactatt caattt-cacacaggaaacag aagcttggcc-3' (SEQ ID NO:1) and 5'-ggcc-aagcttctgtttcctgtgtgaaattgaatagtactctgctatgatatcagcccccggcc-gcactgtcaagaataaactcacccatggcta gcggcc-3' (SEQ ID NO:2) to make pCtl-RFP-AraC-$P_{CP20}$. tyrR was amplified from *E. coli* using the following primers: tyrR-F, 5'-ggc aagcttATGCGTCTGGAAGTCTTTTGTGAA-3' (SEQ ID NO:3); tyrR-R, 5'-ggcatcgatTTACTCTTCGTTCTTCTT-CTGACT-3' (SEQ ID NO:4). The PCR product was cloned into pCtl-RFP-AraC-$P_{CP20}$ to make pCtl-RFP-TyrR.

The sensor module $S_{aroF3}$ was constructed by replacing $P_{BAD}$ with the promoter region of aroF from *E. coli* using the following primers: 5'-GGCGCTAGCCTTTTTCAAA GCATAGCGGATTGT-3' (SEQ ID NO:5) and 5'-GGC GAATTCGATGGCGATCCTGTTT ATGCTCGT-3' (SEQ ID NO:6), and E274Q and N316K were made to tyrR using SOEing PCR with the following primers: tyrR-E274Q-F, 5'-CGGTCGAGAGTCAGCTGTTTGGTC-3' (SEQ ID NO:7); tyrR-E274Q-R, 5'-GACCAAACAGCTGACTC TCGACCG-3' (SEQ ID NO:8); tyrR-N316K-F, 5'-TGCGTTTCCTTAAAGATGGCACTT-3' (SEQ ID NO:9); tyrR-N316K-R, 5'-AAGTGCCATCTTTAAG GAAACGCA-3' (SEQ ID NO:10).

Characterization of tyrR Sensor Module.

$S_{aroF3}$ was transformed into EcDJ106 and EcDJ166, and plated on LB agar with ampicillin. Clones were grown overnight in LB media with ampicillin, inoculated into fresh media the next day, and tyrosine production was quantified after 20 hours. RFP fluorescence was measured using a Spectramax M2 (Molecular Devices) exciting at 495 nm and measuring emission at 520 nm $Abs_{600}$ was also measured using a Spectramax M2.

Construction of FREP Vectors.

mutD was amplified from the MG1655 *E. coli* chromosome and cloned into pCtl-S or pCtl-RFP-S(S designates the sensor module) using the primers 5'-GGC GAATTCTTTAAGAAGGAGATATACATATGA-'3 (SEQ ID NO:11) and 5'-GGCGGTACCTTATGCTC GCCAGAGGCAACTTCC-3' (SEQ ID NO:12) to make pNeg-X or pNeg-RFP-X, respectively. mutD5 was a gift from Dr. Adrienne McKee and cloned into pCtl-X or pCtl-RFP-X using the same pair of primers to make pMut-X or pMut-RFP-X, respectively.

Assessing Phenotypic Diversity after a Single Round of FREP.

MG1655 *E. coli* were transformed with pMut-RFP-$S_{IA44}$. Cells were plated on a LB agar plate with ampicillin, and grown for 1 day at 37° C. Ten mutants with the lowest RFP expression by visual inspection were picked from the plate, inoculated into LB media with ampicillin, and grown overnight at 37° C. Overnight cultures of each mutant were inoculated into fresh LB media the next day to an $Abs_{600}$ of 0.05, grown to an $Abs_{600}$ of 0.4 at 37° C., and made electrocompetent. Each mutant was transformed with pLyc, plated on a LB agar plate with chloramphenicol, and grown for 1 day at 37° C. A colony was picked from each plate, inoculated into LB media with chloramphenicol, and assayed for lycopene production. The same experiment was repeated with pMut-RFP-AraC, except the transformants were plated on LB agar plate with ampicillin and 10 mM arabinose.

For tyrosine production, EcDJ238 were transformed with pMut-RFP-$S_{aroF3}$. Cells were plated on a LB agar plate with ampicillin, and grown for 1 day at 37° C. Ten mutants with the lowest RFP expression by visual inspection were picked from the plate, inoculated into LB media with ampicillin and grown for 24 h at 37° C. Each culture was assayed for tyrosine production. The experiment was repeated using MOPS minimal media with 0.5% glucose.

Long-Term Experiment for Increased Lycopene Production Using FREP.

MG1655 *E. coli* were transformed with pMut-$S_{IA44}$ and pLyc. Cells were plated on a LB agar plate with ampicillin and chloramphenicol, and grown for 2 days at 37° C. Ten colonies were picked and assayed for lycopene production. The colony that produced the most lycopene was passaged to evolve further, and the average of the three highest production levels is reported. The same experiment was repeated with pMut-IA32 and pMut-AraC. For pMut-AraC, 10 mM arabinose was added to the LB agar plates with antibiotics.

Assay for Lycopene Production.

Cells were grown in LB media with chloramphenicol for 20 hours at 37° C. 1 ml of culture was centrifuged at 13,000 g for 1 min, the supernatant was removed, and the pellet was washed with 1 ml of water. 1 mL of acetone was added to the washed pellet, and the sample was vortexed and incubated at 55° C. for 15 min. The sample was centrifuged at 13,000 g for 1 min, and the supernatant was transferred to a cuvette and measured with a spectrophotometer at $Abs_{470}$.

The $Abs_{470}$ data was calibrated to a lycopene standard purchased from Sigma-Aldrich. The amount of lycopene extracted from a culture was normalized to the dry cell weight (dcw) calculated from its $Abs_{600}$ (0.41 g dcw/$Abs_{600}$ (Kim, S. W., Keasling, J. D. Metabolic Engineering of the Nonmevalonate Isopentenyl Diphosphate Synthesis Pathway in *Escherichia coli* Enhances Lycopene Production. *Biotechnology & Bioengineering* 72, 408-415 (2001)).

Assay for L-Tyrosine Production.

Cells were grown in either LB or MOPS minimal media (0.5% glucose) with ampicillin for 20 hours at 37° C. 500 μL of culture was centrifuged at 13,000 g for 1 min, the supernatant was filtered through a 0.452 μm centrifugal filter (VWR) and used for HPLC analysis. L-tyrosine was measured using an Agilent 1200 Series HPLC system with a photodiode array detector set at wavelengths 210, 254, and 280 nm. The samples were separated using a reverse phase $C_{18}$ column (Inertsil 2.1×250 mm, 3.5 μm from GL Sciences, Inc.). The following linear gradient of water (solvent A) and methanol (solvent B) was used with a flow rate of 0.15 ml/min: 5% B from 0-8 min, 5-40% B from 8-13 min, hold at 40% B from 13-16 min, 40-5% B from 16-21 min, and equilibrate at 5% B for 10 min L-tyrosine concentrations were calibrated to an L-tyrosine standard purchased from Sigma-Aldrich.

Example 2

Feedback-Regulated Evolution of Phenotype (FREP)

Materials and Methods
Oligonucleotides and DNA Sequencing

All oligonucleotides were obtained from Integrated DNA Technologies with standard purification. Restriction sites are underlined and start codons are in italics in the primer sequences unless otherwise indicated. DNA sequencing to confirm cloning products were performed by Quintara Biosciences.

Strains.

The kanamycin cassette was cloned from pKD4 into pMevB to make pMevB-Kan using the following primers: 5'-GGCCCCGGGGTGTAGGCTGGAGCTGCTTC-3' (SEQ ID NO:13) and 5'-GGCGAGCTCATGGGAATTAGCCATGGTCC-3' (SEQ ID NO:14). EcHC175 was generated by amplifying mk, pmk, and pmd of the mevalonate operon with the kanamycin cassette from pMevB-Kan with the following primers: 5'-ATCTATAATGATGAGTGATCAGAATTACATGT-GAGAAATTCCAGGCTTTACACTTTAT-3' (SEQ ID NO:15) and 5'-TTACGTTATGCT-CACAACCCCGGCAAATGTCGGGGTTTTTATGG-GAATTAGCCATGGT-3' (SEQ ID NO:16), and knocking out idi in MG1655 *E. coli* with the PCR product according to Datsenko & Wanner (Datsenko, K. A. & Wanner, B. L., One-step inactivation of chromosomal genes in *Escherichia coli* K-12 using PCR products. *PNAS* 97, 6640-6645 (2000)) (homology regions in italics). ScMO219 (*S. cerevisiae* EPY219 (Ro, D.-K., et. al., Production of the antimalarial drug precursor artemisinic acid in engineered yeast. *Nature* 440, 940-943 (2006)) without pADS) was provided by Dr. Mario Ouellet. All genes and promoter sequences amplified from the *E. coli* chromosome were from the strain MG1655. All genes amplified from the *S. cerevisiae* chromosome were from the strain BY4742.

Construction of Sensor Modules Containing IA.

pBAD24M1 was constructed by removing HindIII from pBAD24 using QuickChange PCR with the following primers: 5'-CAGGCATGCTTGCTTGGCTGTTTT-3' (SEQ ID NO:17) and 5'-AAAACAGCCAAGCAAGCATGCCTG-3' (SEQ ID NO:18) (where HindIII was removed is underlined). pCtl-$S_{AraC}$ was constructed by cutting the araC regulon from pBAD24M-gfp (Lee, S. K., et al., Directed Evolution of AraC for Improved Compatibility of Arabinose- and Lactose-Inducible Promoters. *Applied and Environmental Microbiology* 73, 5711-5715 (2007)) using ClaI and EcoRI, and cloning it into pBAD24M1. pCtl-RFP-$S_{AraC}$ was constructed by cloning mcherry into pCtl-$S_{AraC}$ behind $P_{BAD}$ using the following primers: RFP-F, 5'-GGC GGTACCTTAAGTAGGGAGGTAAATACATGGTTTCC AAGGGCGAGGAG-3' (SEQ ID NO:19); RFP-R, 5'-GGC TCTAGATTATTATTTGTACAGCTCATCCAT-3' (SEQ ID NO:20).

IA was constructed by fusing idi to the C-terminus of araC using SOEing PCR. idi was amplified from *E. coli* using the following primers: idi-F, 5'-GGC AAGCTTATGCAAACGGAACACGTCATT-3' (SEQ ID NO:21); idi-SOE-R, 5'-ATGGAGCGACTCGTTAATTT-TAAGCTGGGTAAATGC-3' (SEQ ID NO:22). The C-terminus of araC was amplified from pBAD24 using the following primers: araC-SOE-F, 5'-AT-TAACGAGTCGCTCCATCCA-3' (SEQ ID NO:23); araC-R, 5'-GGCATCGATTTATGACAACTTGACGGCTAC-3' (SEQ ID NO:24). Those PCR products were templates for SOEing PCR using idi-F and araC-R to amplify the fusion construct. IA was cloned into pCtl-$S_{AraC}$, replacing AraC to make pCtl-$S_{IA}$, and pCtl-RFP-$S_{AraC}$ to make pCtl-RFP-$S_{IA}$. Mutants of IA were generated using the GeneMorph II Random Mutagenesis Kit (Agilent Technologies) according to the manufacturer's instructions. IA mutants were cloned into pCtl-RFP using idi-F and araC-R, transformed into EcHC1, and screened for changes in RFP expression in the presence (10 mM) and absence (0 mM) of mevalonate relative to IA. RFP was measured using a Spectramax M2 (Molecular Devices) exciting at 587 nm and measuring emission at 610 nm Two mutants of interest were isolated: IA32 and IA44. pCtl-$S_{Ac}$ and pCtl-RFP-$S_{AC}$ were constructed by amplifying the C-terminal domain of AraC with the primers: 5'-GGC AAGCTTATTAACGAGTCGCTCCATCCA-3' (SEQ ID NO:25) and araC-R, and cloning into pCtl-$S_{AraC}$ and pCtl-RFP-$S_{AraC}$, respectively.

Characterization of IA Sensor Modules.

Expression of RFP from $P_{BAD}$ controlled by one of the transcription factors (AraC, AC, IA, IA32, and IA44) were determined by transforming pCtl-RFP-S(S is the sensor module with one of the transcription factors) into EcHC175 and plating on LB agar plates with ampicillin and kanamycin. Three clones were picked from each plate and grown overnight in LB media with antibiotic. Each overnight culture was inoculated into EZ Rich Defined Media (Teknova) with antibiotic to an $Abs_{600}$ of 0.05, grown for 3 hours at 37° C., induced with IPTG (0.1 mM) and mevalonate (0-10 mM) (or 0-10 mM arabinose for AraC), and grown for an additional 17 hours at 37° C. RFP fluorescence was measured using a Spectramax M2 (Molecular Devices) exciting at 495 nm and measuring emission at 520 nm $Abs_{600}$ was also measured using a Spectramax M2.

Construction of Yeast Synthetic Transcription Factors.

The TEF promoter was amplified and cloned into pESC-Ura to make pESC-$P_{TEF}$ using the primers 5'-GGC GGATCCATAGCTTCAAAATGTTTCTAC-3' (SEQ ID NO:26) and 5'-GGCCCCGGGAAACTTAGATTAGATTGCTAT-3' (SEQ ID NO:27). yEcitrine was amplified and cloned into pESC-P$_{TEF}$ behind P$_{gal10}$ to make pESC-YFP-P$_{TEF}$ using the primers 5'-GGC ATCGATAACATGTCTAAAGGTGAAGAATTA-3' (SEQ ID NO:28) and 5'-GGC AGATCTTTATTTGTACAATTCATCCATACC-3' (SEQ ID NO:29). The cyc1 terminator and TEF promoter were fused using SOEing PCR with the following primers: 5'-GGC CTCGAGATCCGCTCTAACCGAAAAGGA-3' (SEQ ID NO:30), 5'-GTAGAAACATTTTGAAGC-TATCTTCGAGCGTCCCAAAACCTT-3' (SEQ ID NO:31), 5'-AAGGTTTTGGGACGCTCGAAGATAGCTT-CAAAATGTTTCTAC-3' (SEQ ID NO:32), and 5'-GGC AAGCTTAAACTTAGATTAGATTGCTATGCT-3' (SEQ ID NO:33) to make P$_{TEF2}$.

idi was fused to the activator and DNA binding domain of gal4, respectively, using SOEing PCR with idi being 3' of the gal4 domains. The activator domain of gal4 was amplified from S. cerevisiae using the following primers: yAD-F, 5'-GGC CCCGGGACCATGGCCAATTTTAATCAAAGTGGG-3' (SEQ ID NO:34); yAD-R, 5'-ACCGGTTCCACCACCAC-TACCGCCTCCACTTCCGC-CACCCTCTTTTTTTGGGTTTGGT GG-3' (SEQ ID NO:35). The DNA binding domain of gal4 was amplified from S. cerevisiae using the following primers: yDBD-F, 5'-GGC AAGCTTACCATGAAGCTACTGTCTTCTATCGAA-3' (SEQ ID NO:36); yDBD-R, 5'-ACCGGTTCCACCAC-CACTACCGCCTCCACTTCCGCCACCCGATACAGT-CAACTGTCT TTG-3' (SEQ ID NO:37). idi was amplified from E. coli using the following primers: yGI-SOE-F, 5'-AGTGGTGGTGGAACCGGTGGAGGCAGTGGTG-GAGGCCAAACGGAACACGTCATTTT ATTG-3' (SEQ ID NO:38); yAD-GI-R, 5'-GGC CTCGAGTTATTTAAGCTGGGTAAATGCAGA-3' (SEQ ID NO:39); yDBD-GI-R, 5'-GGC GGTACCTTATTTAAGCTGGGTAAATGCAGA-3' (SEQ ID NO:40). The PCR product of yAD-F and yAD-R was fused to the product of yGI-SOE-F and yAD-GI-R to make yAD-GI. The PCR product of yDBD-F and yDBD-R was fused to the product of yGI-SOE-F and yDBD-GI-R to make yDBD-GI. yAD-GI, P$_{TEF2}$, and yDBD-GI were cloned into pESC-YFP-P$_{TEF}$ behind P$_{TEF}$ to make pESC-YFP-S$_{Idi-Gal4}$.

idi1 was fused to the activator and DNA binding domain of gal4, respectively, using SOEing PCR with idi1 being 3' of the gal4 domains. Idi1 was amplified from S. cerevisiae using the following primers: yGI1-SOE-F, 5'-AGTGGTGGTGGAACCGGTGGAGGCAGTGGTG-GAGGCACTGCCGACAACAATAGTAT G-3' (SEQ ID NO:41); yAD-GI1-R, 5'-GGC CTCGAGTTATAGCATTCTATGAATTTGCCTG-3' (SEQ ID NO:42); yDBD-GI1-R, 5'-GGC GGTACCTTATAGCATTCTATGAATTTGCCTG-3' (SEQ ID NO:43). The PCR product of yAD-F and yAD-R was fused to the product of yGI1-SOE-F and yAD-GI1-R to make yAD-GI1. The PCR product of yDBD-F and yDBD-R was fused to the product of yGI1-SOE-F and yDBD-GI1-R to make yDBD-GI1. yAD-GI1, P$_{TEF2}$, and yDBD-GI1 were cloned into pESC-YFP-P$_{TEF}$ behind P$_{TEF}$ to make pESC-YFP-S$_{Idi1-Gal4}$.

erg20 was fused to the activator and DNA binding domain of gal4, respectively, using SOEing PCR with erg20 being 3' of the gal4 domains. erg20 was amplified from S. cerevisiae using the following primers: yGE20-SOE-F, 5'-AGTGGTGGTGGAACCGGTGGAGGCAGTGGTG-GAGGCGCTTCAGAAAAAGAAATTAG GAGA-3' (SEQ ID NO:44); yAD-GE20-R, 5'-GGC CTCGAGCTATTTGCTTCTCTTGTAAACTTT-3' (SEQ ID NO:45); yDBD-GE20-R, 5'-GGC GGTACCCTATTTGCTTCTCTTGTAAACTTT-3' (SEQ ID NO:46). HindIII and KpnI were removed from erg20 using the following primers: 5'-GCTATCTAC AAGCTATTGAAATCT-3' (SEQ ID NO:47), 5'-AGATTT-CAATAGCTTGTAGATAGC-3' (SEQ ID NO:48), 5'-ACTGCTTCGGTACTCCAGAAC-3' (SEQ ID NO:49), and 5'-GTTCTGGAGTACCGAAGCAGT-3' (SEQ ID NO:50) (where HindIII and KpnI were removed are underlined). The PCR product of yAD-F and yAD-R was fused to the product of yGE20-SOE-F and yAD-GE20-R to make yAD-GE20. The PCR product of yDBD-F and yDBD-R was fused to the product of yGE20-SOE-F and yDBD-GE20-R to make yDBD-GE20. yAD-GE20, P$_{TEF2}$, and yDBD-GE20 were cloned into pESC-YFP-P$_{TEF}$ behind P$_{TEF}$ to make pESC-YFP-S$_{Erg20-Gal4}$.

Characterization of Yeast Synthetic Transcription Factors.

pESC-YFP-P$_{TEF}$, pESC-YFP-P$_{TEF2}$-S$_{Idi-Gal4}$, pESC-YFP-S$_{Idi1-Gal4}$, and pESC-YFP-S$_{Erg20-Gal4}$ were transformed into ScMO219, and plated on SD agar-Ura plates. Plates were grown at 30° C. for 2-3 days. Three clones from each plate were grown overnight in SD media-Ura, inoculated into fresh media the following day, and grown for 3 days at 30° C. YFP fluorescence was measured using a Spectramax M2 (Molecular Devices) exciting at 516 nm and measuring emission at 529 nm Abs$_{600}$ was also measured using a Spectramax M2.

Example 3

Programming Adaptive Control to Evolve New Phenotypes

Based on theoretical and experimental data, we constructed an adaptive control process mimicking adaptation by programming cells to change their mutation rate based on a particular phenotype. This system is called feedback-regulated evolution of phenotype (FREP), and is implemented with a sensor to gauge the target phenotype and an actuator to alter the mutation rate. To evolve certain novel traits without any known natural sensors, we developed a framework to assemble synthetic transcription factors and used it to construct four different sensors that recognize isopentenyl diphosphate in bacteria and yeast. We verified FREP by evolving increased tyrosine and isoprenoid production. Taken together, our work demonstrates how complex behaviors could be rationally engineered using control-based systems.

A method capable of regulating mutagenesis in vivo according to a particular phenotype, independent of whether it is linked to growth, could circumvent the constraints set by transformation inefficiencies, deleterious mutations, and assay availability. We created such a method by implementing the variable mutation rate strategy to evolve new traits using an adaptive control system[12] we call feedback-regulated evolution of phenotype (FREP). FREP consists of two modules that control the mutation rate of the genome (M) based on the concentration of a ligand (L) associated with the target phenotype being evolved. The actuator module translates a transcriptional signal (T) into M, and the sensor module modifies T by converting L into a change in transcriptional signal (ΔT). M affects L over time as beneficial mutations for the target phenotype are generated in the genome, creating a feedback loop that causes M to decrease as L increases. The sensor is assembled from two components: a transcription factor (TF) that binds the target ligand and a promoter regulated by the TF. Depending on the target ligand, FREP could evolve a phenotype at either the population or single-cell level. If the ligand is diffusible across the cell membrane and the rate of diffusion $>>\delta L/\delta t$, then the effect of FREP is averaged across the entire population. However, if the ligand is not diffusible across the cell membrane or its diffusion across the membrane is $<<\delta L/\delta t$ then FREP acts on each individual cell separately. Here we demonstrate the application of FREP to each ligand type.

We performed FREP to increase production of the industrially-important amino acid tyrosine[13] in *Escherichia coli* using the tyrosine-responsive TF TyrR[14] to regulate expression of the mutator mutD5[15]. In this implementation, M should be high initially because tyrosine concentration (L) is low, and M is reduced as beneficial mutations that increase tyrosine production appear. We modified TyrR and three TyrR-regulated promoters ($P_{aroF}$, $P_{aroL}$, $P_{aroP}$) to construct twenty different sensors, and screened their response to tyrosine in *E. coli* DJ106 and DJ166, two derivatives of BLR that produce different amounts of tyrosine. We monitored each sensor's output with the fluorescent protein mcherry. Sensor $S_{aroF3}$ was the most sensitive to changes in tyrosine concentration, showing a 25% decrease in fluorescence from the lower to higher producing strain and a dynamic range of 0.44 RFU/mM/OD.

We tested FREP implemented with $S_{aroF3}$ for the sensor and mutD5 for the actuator in *E. coli* DJ238, expressing mcherry bicistronically with mutD5 to monitor T and the relative mutator levels in the cell. We reasoned that mcherry levels could decrease in response to either increased tyrosine production or mutations disrupting the sensor. We isolated ten colonies with the lowest fluorescence after 24 hours and quantified tyrosine production to distinguish between the two scenarios. All ten mutants demonstrated increased tyrosine production, and one exhibited greater than five-fold increase compared to the starting strain. Our observations indicate that raising M when L is low increased tyrosine production, and increased L led to increased ΔT, consistent with our design.

To determine whether FREP could evolve other traits, we implemented an adaptive control system to increase production of isoprenoids, a class of compounds with a wide range of industrial applications, such as drugs[16] and biofuels[17]. Natural TFs for these compounds have not been discovered yet, so we developed a framework to rationally assemble synthetic TFs that could be used to regulate evolution towards high isoprenoid-producing strains. Our strategy was to construct synthetic TFs reminiscent of natural TFs by taking advantage of their structural and functional modularity. The framework assembles a synthetic TFs from three parts: Part1 binds the target ligand, Part2 converts the binding signal into AT by regulating RNA polymerase binding to the target promoter, and Part3 joins Part1 and Part2 together.

For example, AraC regulates expression of arabinose utilization genes from the promoter $P_{BAD}$ by preferentially binding different DNA sequences in the presence and absence of arabinose[18]. AraC has a distinct N-terminal ligand-binding domain (LBD) and C-terminal DNA-binding domain (DBD), and changes its ability to activate or repress $P_{BAD}$ depending on whether the LBD has bound arabinose. We reasoned it should be possible to construct synthetic TFs for isoprenoids by replacing AraC's LBD with proteins that bind isoprenoids, and engineered a synthetic *E. coli* TF (chimeric protein IA) to respond to isopentenyl diphosphate (IPP), the central intermediate for all isoprenoid biosynthesis[19], by fusing the AraC DBD (Part2) and linker (Part3) with IPP isomerase (idi[20]) (Part1). We chose Idi, because crystallographic data indicated that it dimerizes upon binding IPP[21], suggesting that dimerization of Part1 should create at least two different conformational states for IA, only one of which should activate transcription.

A sensor consisting of IA and $P_{BAD}$ was tested by monitoring its output with mcherry in a modified strain of *E. coli* MG1655 able to convert mevalonate to IPP (HC175). Titrating mevalonate from 0-10 mM changed fluorescence by over three fold. There was no change in fluorescence when only the AraC DBD and linker (AC) regulated $P_{BAD}$. We also evaluated expression from the divergent promoter ($P_C$) with cfp. Combined with the $P_{BAD}$ data, IA appears to regulate $P_{BAD}$ and $P_C$ nearly as tightly as AraC. Unlike AraC, IA represses $P_{BAD}$ in the presence of ligand. Furthermore, both half-sites $I_1$ and $I_2$ upstream of $P_{BAD}$ are necessary but interchangeable for IA regulation. These observations indicate IA can regulate T from $P_{BAD}$ based on L (IPP concentration) with a dynamic range of 210 RFU/mM/OD, assuming all of the mevalonate was converted to IPP.

We purified IA to confirm it binds the $I_1$ and $I_2$ half-sites adjacent $P_{BAD}$ in vitro. Gel electrophoresis mobility shift assay (EMSA)[22] experiments showed two bands when $I_1$ and $I_1I_2$ were substrates, and three bands when the substrate was the DNA sequence from $P_C$ to $P_{BAD}$. The additional band supports the observation that IA regulates both $P_{BAD}$ and $P_C$, which have distinct binding sequences. The shifted DNA bands were less intense when IPP was added, indicating that IA's affinity for the binding sequences decreases in the presence of IPP. We confirmed that IPP modulates IA DNA binding using fluorescence resonance energy transfer (FRET), by splitting $I_1$ and $I_1I_2$ into two DNA fragments each constituting half of the original sequence and tagged with either a fluorophore or quencher[23]. Only the presence of IA and both half-sequences induced a change in fluorescence. Adding IPP decreased the change in fluorescence across all concentrations of IA tested. Thus, both in vivo and in vitro data are consistent with IA regulation of transcription from $P_{BAD}$ according to changing IPP concentrations.

To demonstrate that our framework for assembling synthetic TFs could be generalized to other organisms, we constructed a synthetic TF for isoprenoids in *Saccharomyces cerevisiae* using the GAL4 protein, which regulates expression of GAL genes in response to galactose[24]. Similar to AraC, the functional domains of GAL4 are structurally distinct, consisting of an activator domain (AD) and DBD[25]. We reused Idi as Part1 and fused it to the GAL4 AD and DBD (Part2), reasoning that Idi dimerization should bring the AD and DBD in close enough proximity to activate transcription from a GAL promoter (e.g., $P_{GAL10}$). Part3 was a 19 amino acid sequence demonstrating relatively high stability[26]. This sensor was tested by monitoring its output with the fluorescent protein yEcitrine in *S. cerevisiae* MO219, a genetically modified strain that increases isoprenoid production when induced with galactose[27]. We observed a change in fluorescence greater than baseline after galactose induction. Two additional yeast TFs were constructed from yeast proteins known to bind IPP (Idi1[28] and Erg20[29]) as Part1 in place of Idi, and both showed even greater changes in fluorescence following induction. Induction led to an almost two-fold increase in sensor output in response to increased isoprenoid levels using the synthetic TF constructed with Erg20. Combined with IA, these GAL4-based TFs highlight our design's modularity in assembling synthetic TFs for constructing sensors, alleviating the need to rely on pre-existing biological components.

Next, we modified the *E. coli* IPP sensor to tune its dynamic range and maximum transcriptional level ($T_{max}$), generating variants by modifying IA using error-prone PCR. IA32 (L39M, S127C) showed half the $T_{max}$ of IA and a dynamic range of 145 RFU/mM/OD, while IA44 (R267H) showed twice the $T_{max}$ of IA and a dynamic range of 350 RFU/mM/OD. We implemented FREP using a sensor with one of three synthetic TFs (AC, IA32, or IA44) and the mutD5 actuator, and examined these constructs in *E. coli* MG1655 using Luria-Delbruck fluctuation analysis[30]. Thirty colonies for each implementation were tested for rifampicin resistance, an orthogonal phenotype that could be quantified quickly. In general, we observed more rifampicin-resistant mutants with higher mutator expression, and a strong correlation between relative mutator expression and mutation rate (r=0.97). For example, IA32 and IA44 exhibited a four-fold difference in $T_{max}$ and a 2.4-fold difference in M. A negative control consisting of a sensor with IA44 and no actuator generated no rifampicin-resistant mutants. These results show that increasing ΔT decreases M, consistent with our design, and suggest that dynamically controlling mutator expression changes mutation rates.

We performed FREP with IA44 for evolution to increase isoprenoid production in *E. coli* MG1655, and expressed mcherry bicistronically with the actuator to monitor relative mutation rates. Ten colonies with the lowest fluorescence after 24 hours were made electrocompetent and transformed with a plasmid containing the lycopene synthase genes (pLyc). Lycopene measured from a random transformant for all ten colonies was higher than the control not modified with FREP. Six colonies had mutants producing on average 2900 rig lycopene/g dry cell weight. (p.p.m.), a nearly three-fold increase compared to the control that did not undergo FREP, which produced only 1000 p.p.m. Repeating the experiment with a sensor employing AraC as a negative control (AraC does not respond to IPP) generated no mutants producing more lycopene than the initial strain, illustrating the importance of the feedback loop between M and L to couple the mutation rate to the phenotype being evolved.

Finally, we examined the ability of FREP to generate novel phenotypes in the context of a long-term experiment. We co-transformed pLyc with an IPP sensor and mutD5 actuator into *E. coli* MG1655, and monitored the evolution of IPP production using lycopene over 432 hours. We quantified lycopene production every 72 hours from ten random colonies and only passaged the isolate demonstrating the highest production levels. After 432 hours, lycopene production increased to 6800 p.p.m. using IA44, 4700 p.p.m. using IA32, and only 400 p.p.m. using AraC. A negative FREP control implemented with IA44 without an actuator produced 0 p.p.m. For the strains evolved using FREP implemented with IA44 and an actuator, we purified pLyc from each time point. Transforming those plasmids into *E. coli* MG1655 did not lead to more lycopene production compared to the original plasmid. This observation indicates that mutations generated by FREP that increase isoprenoid production reside on the chromosome and are specific to increasing IPP production. Overall, our data indicate a higher mutation rate increased the target phenotype more, beneficial mutations generated were specific to the target trait independent of the screen, and dynamically controlling the mutation rate evolved the target trait faster.

We successfully designed and implemented an adaptive control process programming cells to evolve new phenotypes by deciding whether to increase or decrease mutagenesis. Unlike existing methods to engineer metabolism[31-32], FREP has the advantage of not requiring a priori knowledge about the genes, RNA, proteins, and their interactions that govern the trait being evolved. This approach is distinct from other directed evolution approaches requiring phenotype-specific high-throughput screens or selections to identify high-performing mutants. We demonstrated the application of FREP by evolving engineered *E. coli* with increased tyrosine and IPP production levels, and isolating the evolved strains by monitoring process output with a fluorescent protein. Notably, we also presented a framework to rationally construct synthetic TFs that enable the development of orthogonal sensors less likely to interact with existing cellular networks without being limited to the molecular recognition properties and control functions of naturally-occurring TFs. More broadly, this approach to sensor engineering may have applications in anti-viral therapeutics, gene therapy, and stem cell reprogramming, where tight regulation of complicated spatio-temporal intracellular interactions are necessary[33,34]. Above all, our work provides a foundation for assembling intelligent synthetic biological systems capable of autonomously making decisions by incorporating real-time intra- and extracellular information.

Example 4

Programming Adaptive Control to Evolve New Phenotypes

The complexity inherent in biological systems challenges efforts to rationally engineer novel phenotypes, especially those not amenable to high-throughput screens and selections. In nature, adaptation can rapidly evolve new traits by changing the mutation rate in a cell. Based on theory and experimental data, we constructed an adaptive control process that programs cells to change their mutation rate based on a particular desired phenotype. This system is called feedback-regulated evolution of phenotype (FREP), and is implemented with a sensor to gauge the target phenotype and an actuator to alter the mutation rate. To evolve certain novel traits that have no known natural sensors, we developed a framework to assemble synthetic transcription factors using metabolic enzymes and constructed four different sensors that recognize isopentenyl diphosphate in bacteria and yeast. We verified FREP by evolving increased tyrosine and isoprenoid production. Taken together, our work demonstrates how complex behaviors could be rationally engineered using control-based systems.

Adaptation is a behavior that allows cells to survive and thrive in constantly changing environmental conditions and is characterized by rapid genetic change creating rare beneficial mutations[1]. The appearance of microbial strains with accelerated mutation rates accompany periods of adaptation in both natural and laboratory environments[2,3], such as in the emergence of bacterial antibiotic resistance[4]. Models and experimental data of the adaptive process indicate a "variable mutation rate" strategy is used to evolve traits, where increased mutation rates are only beneficial to populations with low phenotypic diversity, while populations with high degrees of diversity benefit from decreased mutation rates[5,6].

Many mutagenesis strategies to generate diversity in the laboratory exist, but most industrially important phenotypes are not amenable to the high-throughput screens and selections required to isolate mutants exhibiting the desired traits. Furthermore, directed evolution strategies that generate mutant libraries in vitro are limited by the ligation efficiency[8], and those that use mutator strains with unregulated, high mutation rates to generate mutant libraries in vivo[9] suffer from the accumulation of deleterious mutations that eventually lead to cell death. Although adaptation has proven useful for evolving certain phenotypes, its application has been limited to traits that are directly tied to growth[10]. Therefore, a method capable of regulating mutagenesis in vivo according to a particular phenotype, independent of whether it is linked to growth, could circumvent the constraints set by ligation inefficiencies, deleterious mutations, and assay availability.

We created such a method by implementing the "variable mutation rate" strategy to evolve new traits using an adaptive control system we call feedback-regulated evolution of phenotype (FREP) (FIG. 1a). FREP is in theory analogous to the two-module genetic circuit developed by Liu et al[11] that dynamically controls cell motility according to cell density. Similarly, FREP consists of two modules that control the mutation rate of the genome (M) based on the concentration of a ligand (L) associated with the target phenotype being evolved. The actuator module converts a transcriptional signal (T) into M, and the sensor module modifies T by converting L into a change in transcriptional signal ($\Delta T$). M affects L over time as beneficial mutations for the target phenotype are generated in the genome, creating a feedback loop that causes M to decrease as L increases. The sensor is assembled from two components: a transcription factor (TF) that binds the target ligand and a promoter regulated by the TF. Depending on the target ligand, FREP could evolve a phenotype at either the population or single-cell level (FIG. 1b). If the ligand is diffusible across the cell membrane and the rate of diffusion >>dL/dt, then the effect of FREP is averaged across the entire population. However, if the ligand is not diffusible across the cell membrane or its diffusion across the membrane is <<dL/dt, then FREP acts on each individual cell separately. Here we demonstrate the application of FREP to each ligand type.

Figure 17:
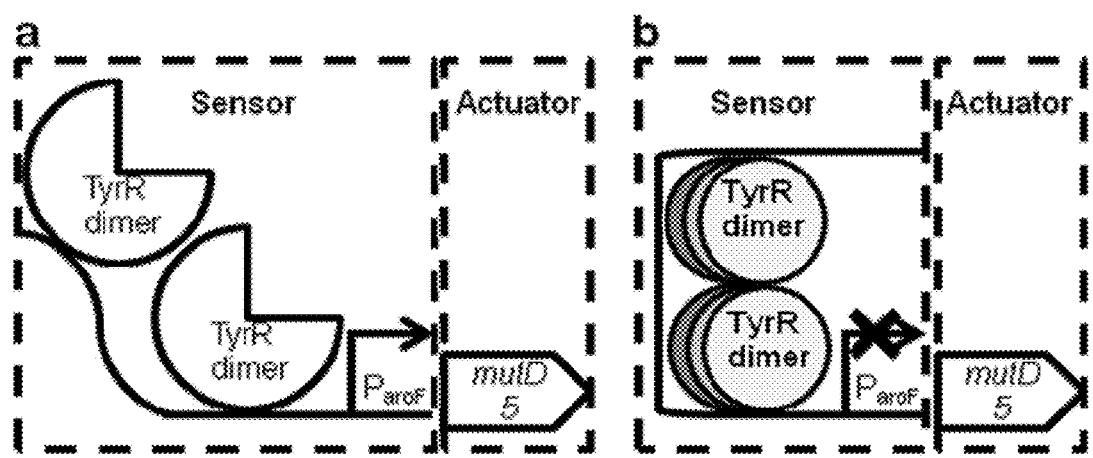
FIG. 17. FREP design to increase tyrosine production. (a) In one design, the sensor consists of TyrR and $P_{aroF}$, and the actuator consists of mutD5. TyrR dimers activate transcription from $P_{aroF}$ in the absence of tyrosine. (b) Tyrosine-bound TyrR form hexamers that dimerize to repress transcription from $P_{aroF}$.
Figure 18:
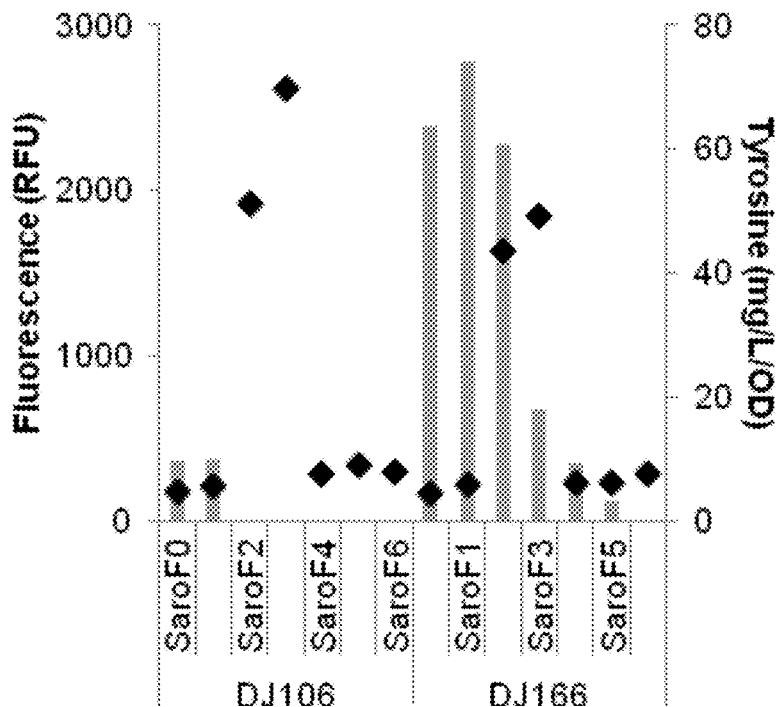
FIG. 18. Fluorescent output from tyrosine sensors using $P_{aroF}$. E. coli DJ106 and DJ166 with one of seven sensors consisting of the promoter $P_{aroF}$ and a variant of TyrR were assessed for their fluorescence output (♦) based on the amount of tyrosine produced (bars). The table lists each sensor with its constituent variant of TyrR and $P_{aroF}$.
Figure 19:
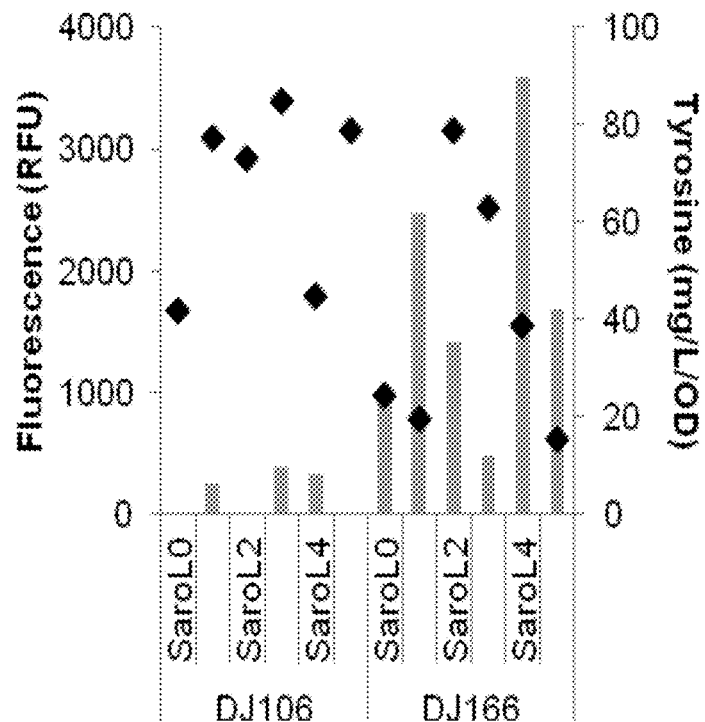
FIG. 19. Fluorescent output from tyrosine sensor using $P_{aroL}$. E. coli DJ106 and DJ166 with one of six sensors consisting of a variant of the promoter $P_{aroL}$ and a variant of TyrR were assessed for their fluorescence output (♦) based on the amount of tyrosine produced (bars). The table lists each sensor with its constituent variant of TyrR and $P_{aroL}$.
Figure 20:
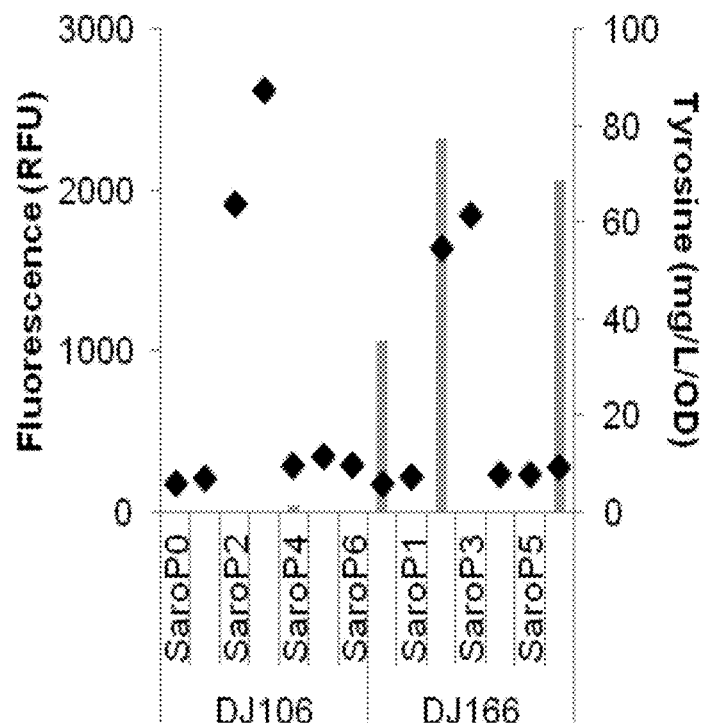
FIG. 20. Fluorescent output from tyrosine sensors using $P_{aroP}$. E. coli DJ106 and DJ166 with one of seven sensors consisting of a variant of the promoter $P_{aroP}$ and a variant of TyrR were assessed for their fluorescence output (♦) based on the amount of tyrosine produced (bars). The table lists each sensor with its constituent variant of TyrR and $P_{aroP}$.

We performed FREP to increase production of the industrially important amino acid tyrosine[12] in *Escherichia coli* using the tyrosine-responsive TF TyrR[13] to regulate expression of the mutator mutD5[14] (FIG. 17). In this implementation, M should be high initially because the tyrosine concentration (L) is low, and M is reduced as beneficial mutations that increase tyrosine production appear. We modified TyrR and three TyrR-regulated promoters ($P_{aroF}$, $P_{aroL}$, $P_{aroP}$) to construct twenty different sensors, and screened their response to tyrosine in *E. coli* DJ106 and DJ166, two derivatives of BLR that produce different amounts of tyrosine. We monitored each sensor's output with the fluorescent protein mcherry (FIGS. 18-20). Sensor $S_{aroF3}$ was the most sensitive to changes in tyrosine concentration, showing a 25% decrease in fluorescence from the lower to higher producing strain and a dynamic range of 0.44 RFU/mM/OD (FIG. 2a).

We tested FREP implemented with $S_{aroF3}$ for the sensor and mutD5 for the actuator in *E. coli* DJ238, expressing mcherry bicistronically with mutD5 to monitor T and the relative mutator levels in the cell. We reasoned that mcherry levels could decrease in response to either increased tyrosine production or mutations disrupting the sensor or mcherry expression. We isolated ten colonies with the lowest fluorescence after 24 hours and quantified tyrosine production to distinguish between the different scenarios. All ten mutants demonstrated increased tyrosine production, and one exhibited greater than five-fold increase compared to the starting strain (FIG. 2b). Our observations indicate that raising M when L (tyrosine) is low increased tyrosine production, and the higher L increased $\Delta T$, consistent with our design.

To determine if FREP could evolve other traits, we implemented an adaptive control system to increase production of isoprenoids, a class of compounds with a wide range of industrial applications, such as pharmaceuticals[15] and biofuels[16]. Natural TFs for these compounds have not been discovered yet, so we developed a framework to rationally assemble synthetic TFs that could be used to regulate evolution towards high isoprenoid-producing strains. Our strategy was to construct synthetic TFs reminiscent of natural TFs by taking advantage of their structural and functional modularity. The framework assembles a synthetic TFs from three parts: Part1 is a metabolic enzyme that binds the target ligand, Part2 converts the binding signal into $\Delta T$ by regulating RNA polymerase binding to the target promoter, and Part3 joins Part1 and Part2 together.

For example, AraC regulates expression of arabinose utilization genes from the arabinose-inducible araBAD promoter ($P_{BAD}$) by preferentially binding different DNA sequences in the presence and absence of arabinose[17]. AraC has a distinct N-terminal, ligand-binding domain (LBD) and C-terminal, DNA-binding domain (DBD), and changes its ability to activate or repress $P_{BAD}$ depending on whether the LBD has bound arabinose. We reasoned that it should be possible to construct synthetic TFs for isoprenoids by replacing AraC's LBD with metabolic enzymes that naturally bind isoprenoids. We engineered a synthetic *E. coli* TF (chimeric protein IA, FIG. 3a) to respond to isopentenyl diphosphate (IPP), the central intermediate for all isoprenoid biosynthesis[18], by fusing the AraC DBD (Part2) and linker (Part3) with IPP isomerase (idi[19]) (Part1). We chose Idi, because crystallographic data indicated that it dimerizes upon binding IPP[20], suggesting that dimerization of Part1 should create at least two, different conformational states for IA, only one of which should activate transcription.

A sensor consisting of IA and $P_{BAD}$ was tested by monitoring its output with mcherry in a modified strain of *E. coli* MG1655 able to convert mevalonate to IPP (HC175). Titrating mevalonate from 0-10 mM changed fluorescence by over three fold (FIG. 3b). There was no change in fluorescence when a synthetic TF consisting of only the AraC DBD and linker (AC) regulated $P_{BAD}$. We also evaluated expression from the divergent araC promoter ($P_C$) with cfp (Table 1). Combined with the $P_{BAD}$ data, IA appears to regulate $P_{BAD}$ and $P_C$ nearly as tightly as AraC. Unlike AraC, IA represses $P_{BAD}$ in the presence of ligand. Furthermore, both half-sites $I_1$ and $I_2$ upstream of $P_{BAD}$ are necessary but interchangeable for IA regulation (Table 2). These observations indicate IA can regulate T from $P_{BAD}$ based on L (IPP concentration) with a dynamic range of 210 RFU/mM/OD, assuming all of the mevalonate was converted to IPP.

TABLE 1

Fluorescence output from $P_{BAD}$ and $P_C$. The promoters $P_{BAD}$ and $P_C$ were regulated by one of three TFs: AC, AraC, or IA. $P_{BAD}$ was monitored using RFP and $P_C$ with CFP. Fluorescence output was normalized to the output from the promoters regulated by IA in the absence of mevalonate (0 mM). Experiments were performed in HC175 induced with 0.1 mM IPTG. 10 mM arabinose was added in the case of "+ Inducer" for AraC, and 10 mM mevalonate was added in the cases of "+ Inducer" for AC and IA.

|  | CFP | | RFP | |
|---|---|---|---|---|
|  | −Inducer | +Inducer | −Inducer | +Inducer |
| AC | 2.8 ± 0.02 | 1.4 ± 0.2 | 0.19 ± 0.03 | 0.11 ± 0.02 |
| AraC | 1.5 ± 0.05 | 0.80 ± 0.03 | 0.22 ± 0.01 | 1.5 ± 0.002 |
| IA | 1.0 ± 0.06 | 0.64 ± 0.1 | 1.0 ± 0.07 | 0.28 ± 0.1 |

TABLE 2

Fluorescence output from $P_{BAD}$ with different regulatory sequences. One of four combinations of the half-sites $I_1$ and $I_2$ (shown in bold) was used to regulate expression from $P_{BAD}$. Fluorescence values were normalized to the output using the wild-type $I_1I_2$ sequence in the absence of inducer (0 mM mevalonate). Experiments were performed in HC175 induced with 0.1 mM IPTG, and 10 mM mevalonate was added in the case of "+ Inducer". The sequences are SEQ ID NOs: 51-54, respectively.

| Sequence | -Inducer | +Inducer |
|---|---|---|
| $I_1I_1$tagcattttatccataagattagcattttatccata | 0.10 ± 0.00 | 0.13 ± 0.01 |
| $I_1I_2$tagcattttatccataagattagcggatcctacctga | 1.00 ± 0.02 | 0.36 ± 0.01 |
| $I_2I_1$tagcggatcctacctgaagattagcattttatccata | 1.12 ± 0.06 | 0.56 ± 0.01 |
| $I_2I_2$tagcggatcctacctgaagattagcggatcctacctga | 0.14 ± 0.01 | 0.11 ± 0.00 |

TABLE 3

Strains and plasmids in this study.

| Name | Archive # | Description |
|---|---|---|
| HC175 | JBEI-4442 | E. coli MG1655 Δidi::($P_{lac}$ mk pmk pmd kan) |
| DJ106 | JBEI-4443 | E. coli BLR ΔtyrR |
| DJ166 | JBEI-4444 | E. coli BLR ΔtyrR ΔpheA/L aroF[P124L] tyrA[M53I; A354V] |
| DJ238 | JBEI-4445 | E. coli MG1655 ΔtyrR |
| MO219 | JBEI-4446 | EPY219 without pADS |
| pLyc | JBEI-4447 | Lycopene expression plasmid |
| pCtl-RFP-$S_{AraC}$ | JBEI-4448 | AraC sensor with RFP and mutD |
| pCtl-RFP-$S_{IA}$ | JBEI-4449 | IA sensor with RFP and mutD |
| pCtl-RFP-$S_{AC}$ | JBEI-4450 | AC sensor with RFP and mutD |
| pCtl-RFP-$S_{IA32}$ | JBEI-4451 | IA32 sensor with RFP and mutD |
| pCtl-$S_{IA44}$ | JBEI-4452 | IA44 sensor with mutD |
| pCtl-RFP-$S_{IA44}$ | JBEI-4453 | IA44 sensor with RFP and mutD |
| pCtl-RFP-$S_{IA}$-I1I1 | JBEI-4454 | IA sensor with RFP, $I_1I_1$, and mutD |
| pCtl-RFP-$S_{IA}$-I2I1 | JBEI-4455 | IA sensor with RFP, $I_2I_1$, and mutD |
| pCtl-RFP-$S_{IA}$-I2I2 | JBEI-4456 | IA sensor with RFP, $I_2I_2$, and mutD |
| pCtl-CFP-RFP-$S_{AC}$ | JBEI-4457 | AC sensor with RFP, CFP, and mutD |
| pCtl-CFP-RFP-$S_{AraC}$ | JBEI-4458 | AraC sensor with RFP, CFP, and mutD |
| pCtl-CFP-RFP-$S_{IA}$ | JBEI-4459 | IA sensor with RFP, CFP, and mutD |
| pCtl-RFP-$S_{aroF0}$ | JBEI-4460 | aroF0 sensor with RFP |
| pCtl-RFP-$S_{aroF1}$ | JBEI-4461 | aroF1 sensor with RFP |
| pCtl-RFP-$S_{aroF2}$ | JBEI-4462 | aroF2 sensor with RFP |
| pCtl-RFP-$S_{aroF3}$ | JBEI-4463 | aroF3 sensor with RFP |
| pCtl-RFP-$S_{aroF4}$ | JBEI-4464 | aroF4 sensor with RFP |
| pCtl-RFP-$S_{aroF5}$ | JBEI-4465 | aroF5 sensor with RFP |
| pCtl-RFP-$S_{aroF6}$ | JBEI-4466 | aroF6 sensor with RFP |
| pCtl-RFP-$S_{aroL0}$ | JBEI-4467 | aroL0 sensor with RFP |
| pCtl-RFP-$S_{aroL1}$ | JBEI-4468 | aroL1 sensor with RFP |
| pCtl-RFP-$S_{aroL2}$ | JBEI-4469 | aroL2 sensor with RFP |
| pCtl-RFP-$S_{aroL3}$ | JBEI-4470 | aroL3 sensor with RFP |
| pCtl-RFP-$S_{aroL4}$ | JBEI-4471 | aroL4 sensor with RFP |
| pCtl-RFP-$S_{aroL5}$ | JBEI-4472 | aroL5 sensor with RFP |
| pCtl-RFP-$S_{aroP0}$ | JBEI-4473 | aroP0 sensor with RFP |
| pCtl-RFP-$S_{aroP1}$ | JBEI-4474 | aroP1 sensor with RFP |
| pCtl-RFP-$S_{aroP2}$ | JBEI-4475 | aroP2 sensor with RFP |
| pCtl-RFP-$S_{aroP3}$ | JBEI-4476 | aroP3 sensor with RFP |
| pCtl-RFP-$S_{aroP4}$ | JBEI-4477 | aroP4 sensor with RFP |
| pCtl-RFP-$S_{aroP5}$ | JBEI-4478 | aroP5 sensor with RFP |
| pCtl-RFP-$S_{aroP6}$ | JBEI-4479 | aroP6 sensor with RFP |
| pESC-YFP-$P_{TEF}$ | JBEI-4480 | Yeast expression plasmid without any sensors |
| pESC-YFP-$S_{Idi-GAL4}$ | JBEI-4481 | Idi-GAL4 sensor with YFP |
| pESC-YFP-$S_{Idi1-GAL4}$ | JBEI-4482 | Idi1-GAL4 sensor with YFP |
| pESC-YFP-$S_{Erg20-GAL4}$ | JBEI-4483 | Erg20-GAL4 sensor with YFP |
| pPro29b-IA | JBEI-4484 | IA tagged with Strep-tag II |
| pMut-$S_{AC}$ | JBEI-4485 | AC sensor with mutD5 |
| pMut-$S_{IA44}$ | JBEI-4486 | IA44 sensor with mutD5 |
| pMut-$S_{IA32}$ | JBEI-4487 | IA32 sensor with mutD5 |
| pMut-$S_{AraC}$ | JBEI-4488 | AraC sensor with mutD5 |
| pMut-RFP-$S_{IA44}$ | JBEI-4489 | IA44 sensor with mutD5 and RFP |
| pMut-RFP-$S_{AraC}$ | JBEI-4490 | AraC sensor with mutD5 and RFP |
| pMut-RFP-$S_{aroF3}$ | JBEI-4491 | aroF3 sensor with mutD5 and RFP |
| HC229 | JBEI-4492 | E. coli undergoing FREP using IA44 with pLyc after 72 hrs |
| HC230 | JBEI-4493 | E. coli undergoing FREP using IA44 with pLyc after 144 hrs |
| HC231 | JBEI-4494 | E. coli undergoing FREP using IA44 with pLyc after 216 hrs |
| HC232 | JBEI-4495 | E. coli undergoing FREP using IA44 with pLyc after 288 hrs |
| HC233 | JBEI-4496 | E. coli undergoing FREP using IA44 with pLyc after 360 hrs |
| HC234 | JBEI-4497 | E. coli undergoing FREP using IA44 with pLyc after 432 hrs |

Figure 21:
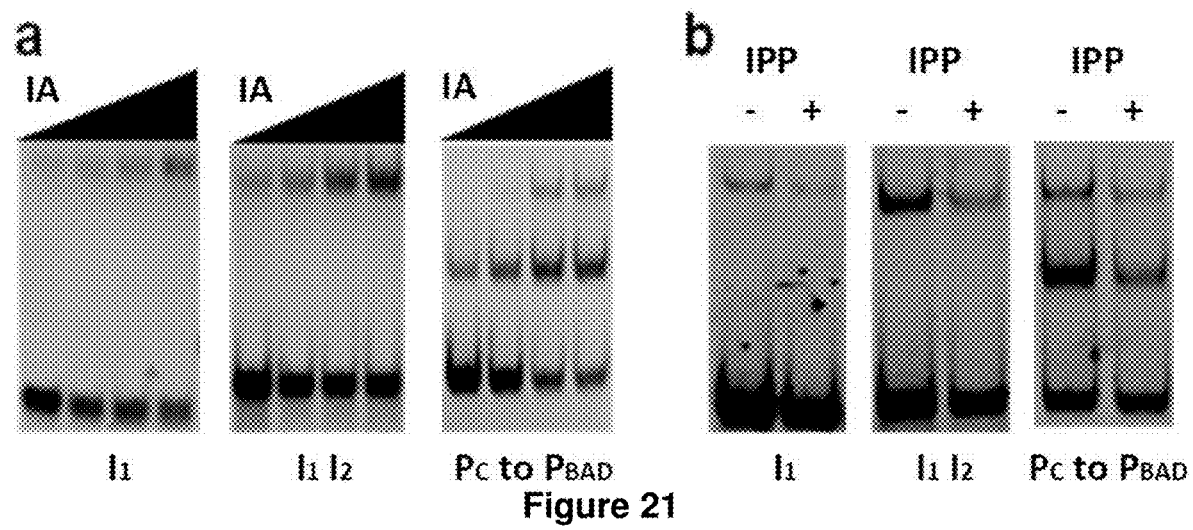
FIG. 21. EMSA experiments show IA binds DNA. We tested whether IA bound to the DNA duplexes of $I_1$, $I_1I_2$, or the sequence from $P_C$ to $P_{BAD}$ (20 nM) in vitro. (a) Increasing IA concentrations (0, 2.5, 5, 10 nM) led to increased intensity in shifted bands. (b) IA binding in the presence (+, 10 μM) and absence (–, 0 μM) of IPP with 10 nM of IA.
Figure 22:
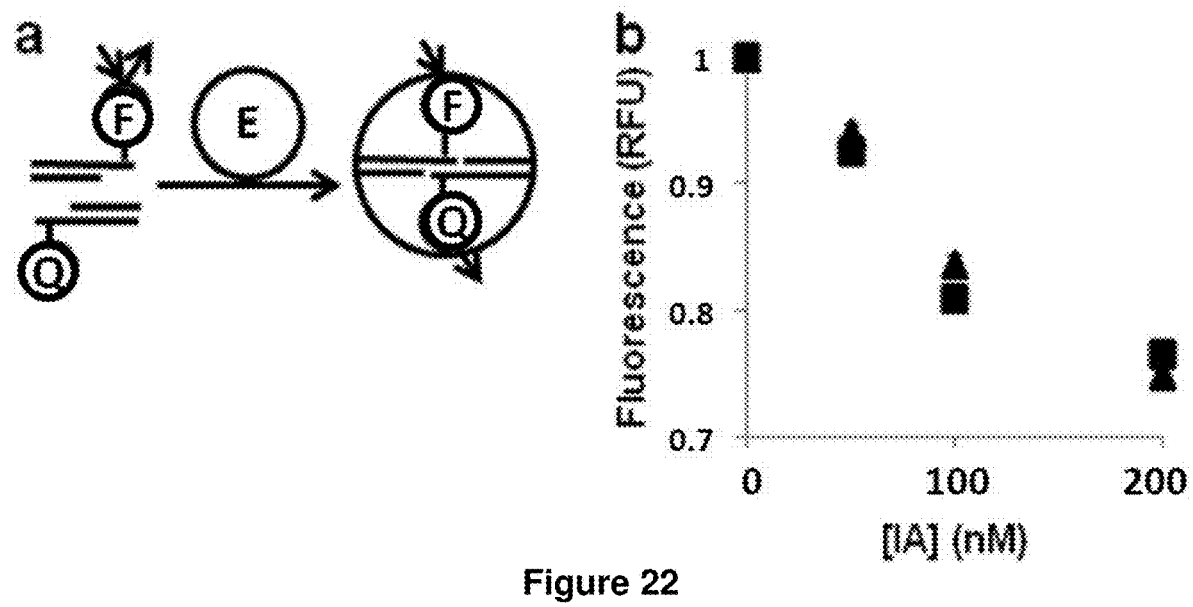
FIG. 22. In vitro FRET DNA-binding assay shows IA interacting with DNA. (a) Schema illustrating FRET DNA-binding assay. A DNA duplex is split into two half-duplexes, and each half is tagged with either a fluorophore (F) or quencher (Q). Fluorescence is detected in the absence of a protein to bring the two half duplexes together. However, the energy is transferred from F to Q when the protein binds both half sequences and brings F in close enough proximity with Q, leading to a decrease in fluorescence. (b) Decreases in fluorescence were observed when the $I_1$ half-duplex (■, 100 nM; ▲, 200 nM) were incubated with different concentrations of IA (0, 5, 10, and 20 nM). Relative fluorescence values were calculated by subtracting the fluorescence value of the negative control without the F label and dividing by the fluorescence value from 0 nM IA.
Figure 23:
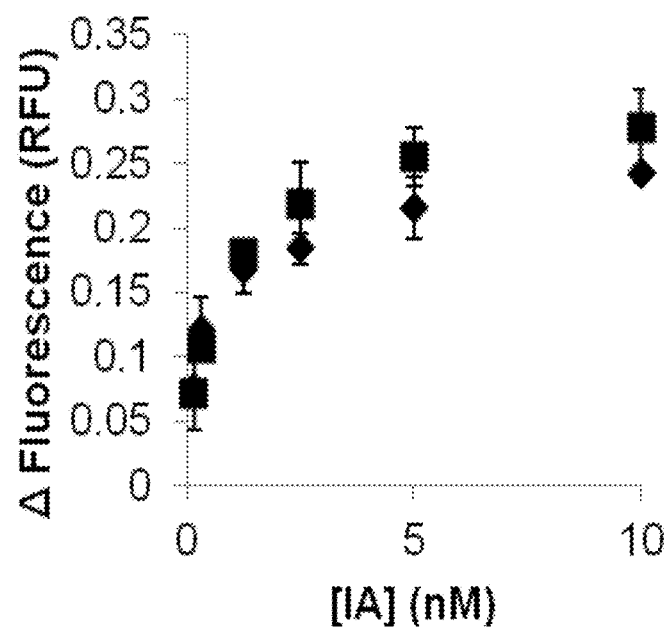
FIG. 23. In vitro FRET DNA-binding assay shows that IPP affects IA binding to DNA. We incubated different concentrations of IA with 100 nM of each $I_1I_2$ labeled DNA half-duplex in vitro. A greater change in fluorescence was observed with increasing concentrations of IA, consistent with the binding experiment with $I_1$ half-duplexes as substrate. The change in fluorescence decreased in the presence of IPP (♦, 500 nM) compared to when no IPP was added (■, 0 nM).

We purified IA to confirm it binds the $I_1$ and $I_2$ half-sites adjacent to $P_{BAD}$ in vitro. Gel electrophoresis mobility shift assay (EMSA[21]) experiments showed two bands when $I_1$ and $I_1I_2$ were substrates, and three bands when the substrate was the DNA sequence from $P_C$ to $P_{BAD}$ (FIG. 21). The additional band supports the observation that IA regulates both $P_{BAD}$ and $P_C$, which have distinct binding sequences. The shifted DNA bands were less intense when IPP was added, indicating that IA's affinity for the binding sequences decreases in the presence of IPP. We confirmed that IPP modulates IA DNA binding using fluorescence resonance energy transfer (FRET) by splitting $I_1$ and $I_1I_2$ into two DNA fragments each constituting half of the original sequence and tagged with either a fluorophore or quencher[22]. Only the presence of IA and both half-sequences induced a change in fluorescence (FIG. 22). Adding IPP decreased the change in fluorescence across all concentrations of IA tested (FIG. 23). Thus, both in vivo and in vitro data are consistent with IA regulation of transcription from $P_{BAD}$ according to changing IPP concentrations, and both $I_1$ and $I_2$ half-sites are necessary for this regulation.

To further evaluate our framework for assembling synthetic TFs, we constructed a synthetic TF for isoprenoids in Saccharomyces cerevisiae using the GAL4 protein, which regulates expression of GAL genes in response to galactose[23]. Similar to AraC, the functional domains of GAL4 are structurally distinct, consisting of an activator domain (AD) and DBD[24]. We reused Idi as Part1 and fused it to the GAL4

AD and DBD (Part2), reasoning that Idi dimerization should bring the AD and DBD in close enough proximity to activate transcription from a GAL promoter (e.g., $P_{GAL10}$). Part3 was a 19-amino acid sequence having relatively high stability[25]. This sensor (FIG. 3c) was tested by monitoring its output with the fluorescent protein yEcitrine in *S. cerevisiae* MO219, a genetically modified strain that increases isoprenoid production when induced with galactose[26]. We observed a change in fluorescence greater than baseline after galactose induction (FIG. 3d). Two additional yeast TFs were constructed from yeast enzymes known to catalyze reactions with IPP as a substrate (Idi1[27] and Erg20[28]) as Part1 in place of Idi, and both showed even greater changes in fluorescence following induction. Induction led to an almost two-fold increase in sensor output in response to increased isoprenoid levels using the synthetic TF constructed with Erg20. Combined with IA, these GAL4-based TFs highlight the modularity of our framework in assembling synthetic TFs for constructing sensors, alleviating the need to rely on pre-existing biological components.

Figure 24:
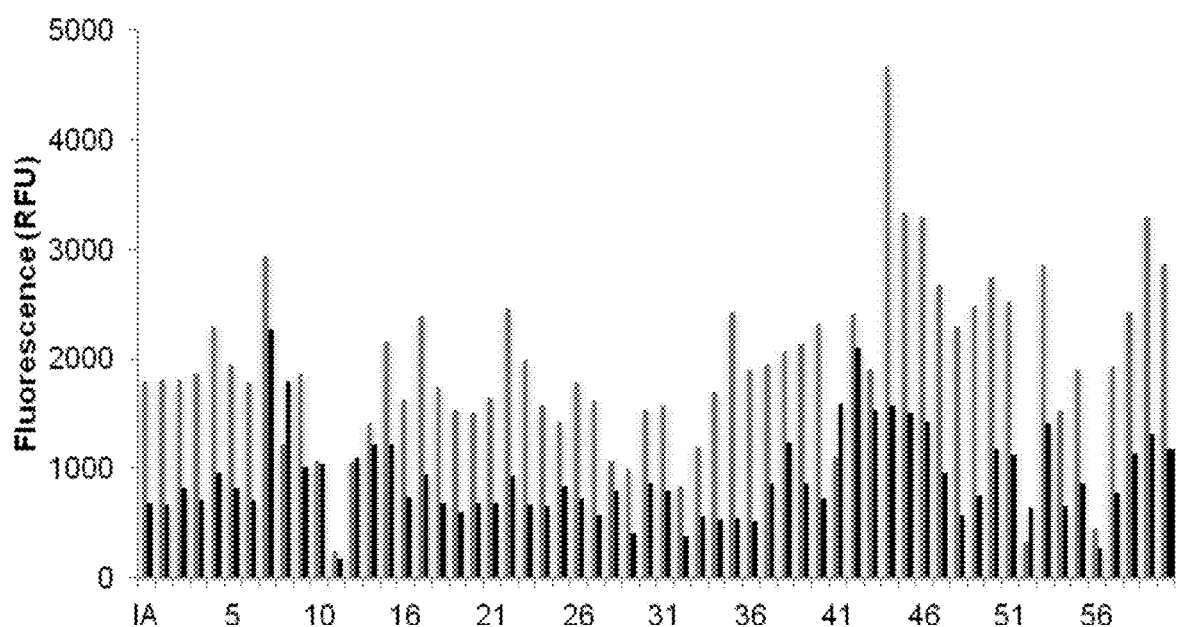
FIG. 24. Modified IPP sensors exhibit different dynamics 60 different sensors for IPP were generated by mutating IA using error-prone PCR and monitoring sensor output from $P_{BAD}$ with mcherry. Output is presented in relative fluorescence units normalized to OD measured at 600 nm Gray bars indicate output in the absence of mevalonate (0 mM), and black bars indicate output in the presence of mevalonate (10 mM). A control sensor with IA is included on the left.
Figure 25:
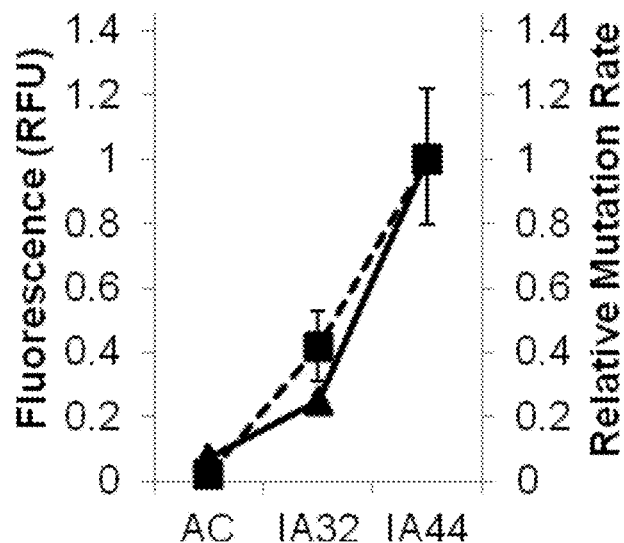
FIG. 25. Fluorescence output and mutation rate correlate. FREP was implemented with the mutD5 mutator and an IPP sensor with one of the following TFs: AC, IA32, or IA44. Fluorescence (▲) represents the maximum fluorescence measured from HC175 in the absence of mevalonate for each sensor normalized to that with IA44 (FIG. 3B). The mutation rate (■) was calculated with Luria-Delbruck analysis using rifampicin resistance as the phenotype, analyzed using FALCOR, and the mutation rate for each TF determined by FALCOR was normalized to that determined for IA44. The correlation coefficient between measured fluorescence and mutation rate is r=0.97.

Next, we modified the *E. coli* IPP TF IA using error-prone PCR to create IPP sensors with different dynamic ranges and maximum transcription levels ($T_{max}$). Out of the 60 variants screened (FIG. 24), IA32 (L39M, S127C) showed half the $T_{max}$ of IA and a dynamic range of 145 RFU/mM/OD, while IA44 (R267H) showed twice the $T_{max}$ of IA and a dynamic range of 350 RFU/mM/OD (FIG. 3C). We implemented FREP using one of three synthetic TFs (AC, IA32, or IA44) as part of the sensor and the mutD5 actuator, and examined these constructs in *E. coli* MG1655 using Luria-Delbruck fluctuation analysis[29]. Thirty colonies for each implementation were tested for rifampicin resistance, an orthogonal phenotype that could be quantified quickly. In general, we observed more rifampicin-resistant mutants with higher mutator expression, and a strong correlation between relative mutator expression and mutation rate (r=0.97) (FIG. 25). For example, IA32 and IA44 exhibited a four-fold difference in T. and a 2.4-fold difference in M. A negative control consisting of a sensor with IA44 and no actuator generated no rifampicin-resistant mutants. These results show that increasing AT decreases M, consistent with our design, and suggest that dynamically controlling mutator expression changes mutation rates. Furthermore, the ability to adjust the dynamic range of the TF allows the target production level evolved using FREP to be controlled.

Figure 26:
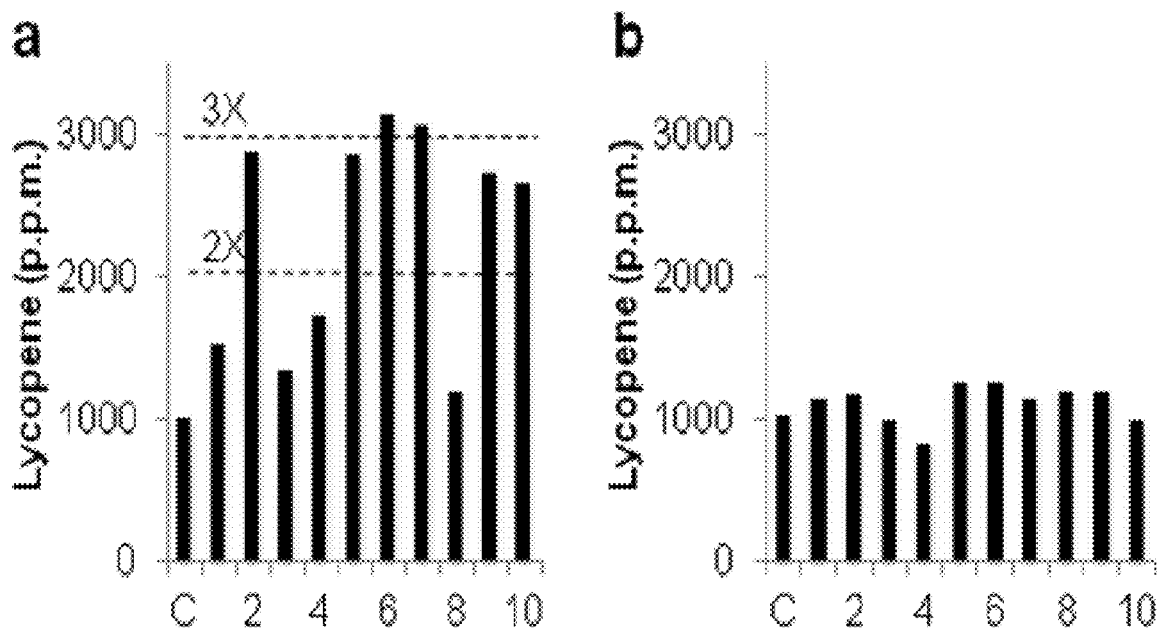
FIG. 26. FREP evolved increased IPP in 24 hours. C is the negative control that did not undergo FREP. (a) The effects of dynamic control of mutation rate was determined by comparing lycopene production from C to 10 colonies of *E. coli* MG1655 after undergoing FREP with IA44 for 24 hours. (b) The effects of static control of mutation rate was determined by comparing lycopene production from C to 10 colonies of *E. coli* MG1655 after undergoing FREP with AraC induced with 10 mM arabinose for 24 hours.

We performed FREP with IA44 to increase isoprenoid production in *E. coli* MG1655, and expressed mcherry bicistronically with the actuator to monitor relative mutation rates. Ten colonies with the lowest fluorescence after 24 hours were made electrocompetent and transformed with a plasmid containing the lycopene synthase genes (pLyc). Lycopene measured from a random transformant for all ten colonies was higher than the control not modified with FREP. Six colonies had mutants producing on average 2900 rig lycopene/g dry cell weight (p.p.m.), a nearly three-fold increase compared to the control that did not undergo FREP, which produced only 1000 p.p.m. (FIG. 26). Repeating the experiment with a sensor employing AraC as a negative control (AraC does not respond to IPP) generated no mutants producing more lycopene than the initial strain, illustrating the importance of the feedback loop between M and L to couple the mutation rate to the phenotype being evolved.

Figure 27:
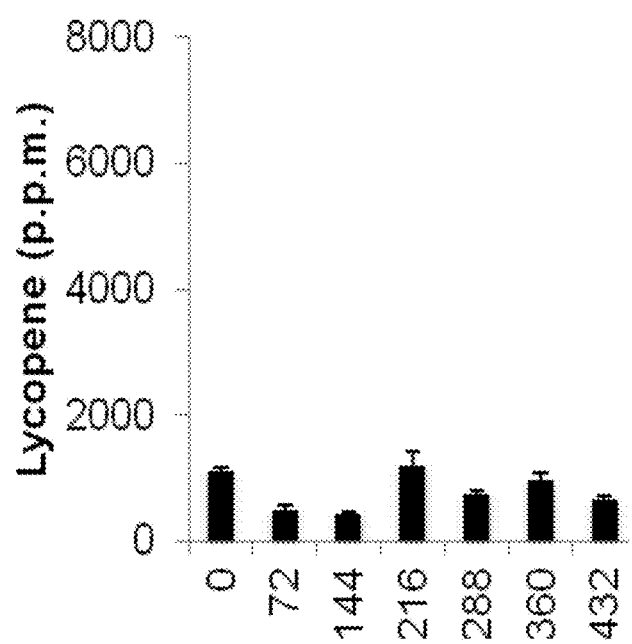
FIG. 27. pLyc from mutants do not lead to increased lycopene production. pLyc was isolated from *E. coli* MG1655 after undergoing FREP for 0, 72, 144, 216, 288, 360, and 432 hours. The plasmids were transformed into *E. coli* MG1655 and lycopene production was quantified.

Finally, we examined the ability of FREP to generate novel phenotypes in the context of a long-term experiment. We co-transformed pLyc with an IPP sensor and mutD5 actuator into *E. coli* MG1655, and monitored the evolution of IPP production using lycopene as a reporter over 432 hours. We quantified lycopene production every 72 hours from ten random colonies and only passaged the isolate demonstrating the highest production levels. After 432 hours, lycopene production increased to 6800 p.p.m. using IA44, 4700 p.p.m. using IA32, and only 400 p.p.m. using AraC (FIG. 4). A negative FREP control implemented with IA44 without an actuator produced 0 p.p.m. For the strains evolved using FREP implemented with IA44 and an actuator, we purified pLyc from each time point. Transforming those plasmids into *E. coli* MG1655 did not lead to more lycopene production compared to the original plasmid (FIG. 27). This observation indicates that mutations generated by FREP that increase isoprenoid production reside on the chromosome and are specific to increasing IPP production. Overall, our data demonstrate that dynamical control of the mutation rate evolved a particular phenotype faster than either the absence of or static control of the mutation rate, and the beneficial mutations generated by the dynamic control process are specific to the desired phenotype.

We successfully designed and implemented an adaptive control process capable of regulating the mutation rate by gauging the degree to which a strain exhibits a desired phenotype. Although the current implementation of FREP appears slower than certain alternative strategies for engineering metabolism[30,31], FREP is unique because it has the advantage of evolving a trait without a priori knowledge about the genes, RNA, proteins, and their interactions that govern the trait being engineered. We demonstrated the application of FREP by evolving *E. coli* to increase tyrosine and IPP production, and isolating the evolved strains by monitoring the actuator level with a fluorescent protein. We confirmed that FREP was able to evolve phenotypes for target ligands that are permeable (tyrosine) and for those that are impermeable (IPP) to the cell membrane. Once the level of a target trait saturates using a particular TF, its dynamic range could be altered to enable further increases in the level of the trait using FREP. Additionally, we presented a framework to rationally construct synthetic TFs using metabolic enzymes that enable the development of orthogonal sensors less likely to interact with existing cellular networks without being limited to the molecular recognition properties and control functions of naturally occurring TFs. Above all, our work provides a foundation for assembling intelligent, synthetic biological systems capable of autonomously making decisions by incorporating real-time, intra- and extracellular information.

Methods

Oligonucleotides and DNA Sequencing

All oligonucleotides were obtained from Integrated DNA Technologies and are presented in FIG. 28. DNA sequencing was performed by Quintara Biosciences.

Strains and Plasmids Availability

Strains, plasmids, and plasmid sequences (in Genbank format) are deposited in the private instance of the JBEI registry and will be moved to the public instance (webpage at:public-registry.jbei.org) after publication. Strains and plasmids are available from Addgene (webpage at:addgene-.org), and listed in Table 3.

Strains

We cloned the kanamycin cassette from pKD4 into pMevB[32] to construct pMevB-Kan using the primers Kan-F and Kan-R. We engineered EcHC175 by amplifying mk, pmk, and pmd of the mevalonate operon with the kanamycine cassette from pMevB-Kan with the primers IdiKO-F and IdiKO-R, and knocking out idi in *E. coli* MG1655 with the PCR product according to Datsenko & Wanner[33]. *E. coli*

DJ106, DJ166, and DJ238 were gifts from Dr. Darmawi Juminaga. *S. cerevisiae* MO219 was a gift from Dr. Mario Ouellet. Genes and promoter sequences amplified from the *E. coli* chromosome were from MG1655. Genes amplified from the *S. cerevisiae* chromosome were from BY4742.

Construction of pLyc

We cloned crtE, crtI, and crtB from pT-LYCm4 (gift from Dr. Adrienne McKee) into pBAD18-Cm using the restriction enzymes SpeI and HindIII following standard restriction digest and ligation cloning protocols.

Construction of Plasmids Containing *E. coli* IPP Sensor Modules pCtl-RFP-$S_{AraC}$ ($S_{AraC}$: sensor containing AraC) was constructed by removing HindIII from pBAD24 using Quick-Change PCR with the primers DelHindIII-F and DelHindIII-R, cloning in the DNA sequence from araC to $P_{BAD}$ from pBAD24M-gfp[34] using ClaI and EcoRI, cloning in mutD amplified from *E. coli* using the primers MutD-F and MutD-R, and cloning in mcherry using the primers RFP-F and RFP-R 3' of the araBAD promoter, $P_{BAD}$.

The chimeric protein IA was constructed by fusing idi to the C-terminus of araC using SOEing PCR. idi was amplified from *E. coli* using the primers Idi-F and Idi-SOE-R, and the linker and C-terminus of araC were amplified from pBAD24 using the primers AraC-SOE-F and AraC-R. These two PCR products were templates for SOEing PCR using Idi-F and AraC-R to amplify the chimeric protein. We cloned IA into pCtl-RFP-$S_{AraC}$ by replacing AraC to make pCtl-RFP-$S_{IA}$.

Mutants of IA were generated using the GeneMorph II Random Mutagenesis Kit (Agilent Technologies) according to the manufacturer's instructions. We cloned the IA mutants into pCtl-RFP-$S_{IA}$ using Idi-F and AraC-R, transformed the constructs into EcHC175, and screened for changes in RFP expression relative to IA in the presence (10 mM) and absence (0 mM) of mevalonate with 0.1 mM isopropyl β-D-1-thiogalactopyranoside (IPTG) (Sigma-Aldrich). RFP was measured using a Spectramax M2 (Molecular Devices) exciting at 587 nm and measuring emission at 610 nm We isolated two mutants: IA32 and IA44. pCtl-RFP-$S_{Ac}$ was constructed by amplifying the C-terminal domain of AraC with the primers AC-F and AraC-R, and cloning into pCtl-RFP-$S_{AraC}$. pCtl-RFP-$S_{IA44}$ was digested with ClaI and KpnI, and the fragment containing IA44 to mutD was cloned into pBAD24 to construct pCtl-$S_{IA44}$.

Construction of Plasmids Containing mutD5 Mutator Module

The mutator mutD5 was a gift from Dr. Adrienne McKee and cloned into pCtl-$S_{IA44}$, pCtl-RFP-$S_{AraC}$, pCtl-RFP-$S_{IA44}$, and pCtl-RFP-$S_{aroF3}$ using the primers MutD-F and MutD-R to make pMut-$S_{IA44}$, pMut-RFP-$S_{AraC}$, pMut-RFP-$S_{IA44}$, and pMut-RFP-$S_{aroF3}$. pMut-$S_{AC}$, pMut-$S_{AraC}$, pMut-$S_{IA32}$ were constructed by cutting the transcription factor (TF) from pCtl-RFP-$S_{Ac}$, pCtl-RFP-$S_{AraC}$, pCtl-RFP-$S_{IA32}$ using ClaI and HindIII, and cloning the fragments into pMut-$S_{IA44}$.

Characterization of *E. coli* IPP Sensor Modules

We measured expression of RFP from $P_{BAD}$ controlled by one of the TFs (AraC, AC, IA, IA32, or IA44) by transforming pCtl-RFP-S(S designates a sensor with one of the TFs) into EcHC175 and plating on LB agar plates with ampicillin and kanamycin. We picked three clones from each plate, grew each clone in LB medium with antibiotics overnight, and inoculated each culture into fresh EZ Rich Defined Medium (Teknova) with antibiotics to an initial $Abs_{600}$ of 0.05 the following day. Each fresh culture was grown for 3 hours at 37° C., induced with IPTG (0.1 mM) and mevalonate (0-10 mM) (or 0-10 mM arabinose for AraC), and grown for an additional 17 hours at 37° C. We measured RFP fluorescence exciting at 495 nm and measuring emission at 520 nm, and $Abs_{600}$ using a Spectramax M2.

To determine IA's binding sequence upstream of $P_{BAD}$, we amplified $I_LI_I$ using the primer I1I1-F, $I_2I_1$ using the primer I2I1-F, or $I_2I_2$ using the primer I2I2-F, all paired with AraReg-R and using pCtl-RFP-$S_{IA}$ as template. The PCR products were cloned into pCtl-RFP-$S_{IA}$ to replace the $I_1I_2$ sequence to make pCtl-RFP-$S_{IA}$-$I_1I_1$, pCtl-RFP-$S_{IA}$-$I_2I_1$, and pCtl-RFP-$S_{IA}$-$I_2I_1$. RFP expression from the modified binding sequences was determined as described above.

We amplified CFP using the primers CFP-F and CFP-R, and inserted it 3' of the TF expressed 3' of $P_C$ into pCtl-RFP-$S_{AC}$, pCtl-RFP-$S_{AraC}$, and pCtl-RFP-$S_{IA}$ to make pCtl-CFP-RFP-$S_{Ac}$, pCtl-CFP-RFP-$S_{AraC}$, and pCtl-CFP-RFP-$S_{IA}$. RFP and CFP expression from these constructs were determined as indicated above, and CFP fluorescence was measured using a Spectramax M2 exciting at 433 nm and measuring emission at 475 nm Construction of Plasmids Containing Tyrosine Sensor Modules We replaced $P_C$ with CP20[35] in pCtl-RFP-$S_{AraC}$ using the primers CP20-F and CP20-R, and cloned in tyrR amplified from *E. coli* using the primers TyrR-F and TyrR-R to construct pCtl-RFP-TyrR.

pCtl-RFP-$S_{aroF0}$ was constructed by amplifying the promoter region of aroF from *E. coli* using the primers AroF0-F and AroF0-R, and cloning the PCR product into pCtl-RFP-TyrR to replace $P_{BAD}$. pCtl-RFP-$S_{aroF1}$ was constructed by mutating TyrR with the primers TyrR-E274Q-F and TyrR-E274Q-R to make TyrR E274Q[36], and cloning the PCR product into pCtl-RFP-$S_{aroF0}$. pCtl-RFP-$S_{aroF2}$ was constructed by mutating TyrR with the primers TyrR-N316K-F and TyrR-N316K-R to make TyrR N316K[37], and cloning the PCR product into pCtl-RFP-$S_{aroF0}$. pCtl-RFP-$S_{aroF3}$ was constructed by mutating TyrR E274Q with the primers TyrR-N316K-F and TyrR-N316K-R, and cloning the PCR product into pCtl-RFP-$S_{aroF0}$. The N-terminus of TyrR was also truncated to different lengths to generate TyrR Δ43, TyrR Δ93, and TyrR Δ187[38]. pCtl-RFP-$S_{aroF4}$ was constructed by amplifying TyrR with the primers Del43TyrR-F and TyrR-R, and cloning the PCR product into pCtl-RFP-$S_{aroF0}$. pCtl-RFP-$S_{aroF5}$ was constructed by amplifying TyrR with the primers Del93TyrR-F and TyrR-R, and cloning the PCR product into pCtl-RFP-$S_{aroF0}$. pCtl-RFP-$S_{aroF6}$ was constructed by amplifying TyrR with the primers Del187TyrR-F and TyrR-R, and cloning the PCR product into pCtl-RFP-$S_{aroF0}$.

pCtl-RFP-$S_{aroL0}$ was constructed by replacing $P_{BAD}$ with the promoter region of aroL from *E. coli* using the primers AroL0-F and AroL0-R, and cloning the PCR product into pCtl-RFP-TyrR. TyrR from pCtl-RFP-$S_{aroF1}$, pCtl-RFP-$S_{aroF2}$, and pCtl-RFP-$S_{aroF3}$ were amplified using the primers TyrR-F and TyrR-R and cloned into pCtl-RFP-$S_{aroL0}$ to construct pCtl-RFP-$S_{aroL1}$, pCtl-RFP-$S_{aroL2}$, and pCtl-RFP-$S_{aroL3}$, respectively. The TyrR boxes 1, 2, 3 of the promoter $P_{araL}$ were also modified to tune TyrR regulation of the promoter[39]. pCtl-RFP-$S_{aroL4}$ was constructed by modifying the sequences of box 1 and 2 of $P_{aroL}$ in pCtl-RFP-$S_{aroL0}$ with the primers AroLBox1 and 2-F and AroLBox1 and 2-R. pCtl-RFP-$S_{aroL5}$ was constructed by modifying the box 3 sequence of $P_{aroL}$ in pCtl-RFP-$S_{aroL0}$ with the primers AroL-Box3-F and AroLBox3-R.

pCtl-RFP-$S_{aroP0}$ was constructed by replacing $P_{BAD}$ with the promoter region of aroP from *E. coli* using the primers AroP0-F and AroP0-R, and cloning the PCR product into pCtl-RFP-TyrR. TyrR from pCtl-RFP-$S_{aroF1}$, pCtl-RFP-$S_{aroF2}$, and pCtl-RFP-$S_{aroF3}$ were amplified using the primers TyrR-F and TyrR-R and cloned into pCtl-RFP-$S_{aroP0}$ to construct pCtl-RFP-$S_{aroP1}$, pCtl-RFP-$S_{aroP2}$, and pCtl-RFP-$S_{aroP3}$, respectively. pCtl-RFP-$S_{aroP4}$ was constructed by modifying the $P_2$ sequence of $P_{aroP}$ to make $P_{2up}^{40}$ in pCtl-RFP-$S_{aroP0}$ with the primers P2UP-F and P2UP-R. pCtl-RFP-$S_{aroP5}$ and pCtl-RFP-$S_{aroP6}$ were constructed by amplifying TyrRΔ43 and TyrRΔ93 from pCtl-RFP-$S_{aroF4}$ and pCtl-RFP-$S_{aroF5}$, respectively, using the primers Del43TyrR-F or Del93TyrR-F paired with TyrR-R, and cloning the PCR products into pCtl-RFP-$S_{aroP4}$.

Characterization of Tyrosine Sensor Modules

Plasmids containing each of the twenty tyrosine sensors described above were transformed into *E. coli* DJ106 and DJ166, and plated on LB agar with ampicillin. Clones were grown overnight in LB medium with ampicillin, inoculated into EZ Rich Defined Medium the next day to an initial $Abs_{600}$ of 0.05, and tyrosine production was quantified after 20 hours. RFP fluorescence and $Abs_{600}$ were measured as described earlier. The experiment was repeated in triplicate for $S_{aroF3}$, $S_{aroL5}$, and $S_{aroP6}$.

Construction of Yeast Synthetic Transcription Factors and IPP Sensor Modules

The TEF promoter was amplified and cloned into pESC-Ura to make pESC-$P_{TEF}$ using the primers TEF-F and TEF-R. yEcitrine was amplified and cloned into pESC-$P_{TEF}$ behind $P_{gal10}$ to make pESC-YFP-$P_{TEF}$ using the primers YEcitrine-F and YEcitrine-R. The cyc1 terminator and TEF promoter were fused using SOEing PCR with the primers CYC1-SOE-F, CYC1-SOE-R, TEF-SOE-F, and TEF-SOE-R to make the PCR product $P_{TEF2}$.

idi was fused to the activator and DNA-binding domains of gal4, respectively, using SOEing PCR with idi being 3' of the gal4 domains. The activator domain of gal4 was amplified from *S. cerevisiae* using the primers AD-F and AD-SOE-R. The DNA binding domain of gal4 was amplified using the following primers: DBD-F and DBD-SOE-R. The AD-SOE-R and DBD-SOE-R primers included the linker sequence joining the domains to idi. idi was amplified from *E. coli* using the primers GI-SOE-F with AD-GI-R or GI-SOE-F with DBD-GI-R. The PCR product of AD-F and AD-SOE-R was fused to the product of GI-SOE-F and AD-GI-R to make AD-GI. The PCR product of DBD-F and DBD-SOE-R was fused to the product of GI-SOE-F and DBD-GI-R to make DBD-GI. AD-GI, $P_{TEF2}$, and DBD-GI were cloned into pESC-YFP-$P_{TEF}$ behind $P_{TEF}$ to make pESC-YFP-$S_{Idi\text{-}GAL4}$.

idi1 was fused to the activator and DNA binding domains of gal4, respectively, using SOEing PCR with idi1 being 3' of the gal4 domains. Idi1 was amplified from *S. cerevisiae* using the primers GI1-SOE-F and AD-GI1-R or GI1-SOE-F and DBD-GI1-R. The PCR product of AD-F and AD-SOE-R was fused to the product of GI1-SOE-F and AD-GI1-R to make AD-GI1. The PCR product of DBD-F and DBD-SOE-R was fused to the product of GI1-SOE-F and DBD-GI1-R to make DBD-GI1. AD-GI1, $P_{TEF2}$, and DBD-GI1 were cloned into pESC-YFP-$P_{TEF}$ behind $P_{TEF}$ to make pESC-YFP-$S_{Idi1\text{-}GAL4}$.

erg20 was fused to the activator and DNA binding domains of gal4, respectively, using SOEing PCR with erg20 being 3' of the gal4 domains. erg20 was amplified from *S. cerevisiae* using the primers GE20-SOE-F with AD-GE20-R or GE20-SOE-F with DBD-GE20-R. HindIII and KpnI were removed from erg20 using the primers DelHindIII-Erg20-F, DelHindIII-Erg20-R, DelKpnI-Erg20-F, and DelKpnI-Erg20-R (where HindIII and KpnI were removed are underlined). The PCR product of AD-F and AD-SOE-R was fused to the product of GE20-SOE-F and AD-GE20-R to make AD-GE20. The PCR product of DBD-F and DBD-SOE-R was fused to the product of GE20-SOE-F and DBD-GE20-R to make DBD-GE20. AD-GE20, $P_{TEF2}$, and DBD-GE20 were cloned into pESC-YFP-$P_{TEF}$ 3' of $P_{TEF}$ to make pESC-YFP-$S_{Erg20\text{-}GAL4}$.

Characterization of Yeast IPP Sensor Modules pESC-YFP-$P_{TEF}$, pESC-YFP-$S_{Idi\text{-}GAL4}$, pESC-YFP-$S_{Idi1\text{-}GAL4}$, and pESC-YFP-$S_{Erg20\text{-}GAL4}$ were transformed into ScMO219 using electroporation, plated on Synthetic Defined (SD) agar without uracil and with 2% glucose, and grown at 30° C. for 3 days. SD medium was composed of 1×CSM without the appropriate amino acids (Sunrise Science Products) and 1× Difco Yeast Nitrogen Base without amino acids (BD), prepared according to the manufacturers' instructions. Three clones from each plate were grown overnight in SD medium without uracil and with 2% glucose, inoculated into fresh medium without uracil and with 1.8% galactose and 0.2% glucose the following day to an initial $Abs_{600}$ of 0.05, and grown for 3 days at 30° C. YFP fluorescence was measured using a Spectramax M2 (Molecular Devices) exciting at 516 nm and measuring emission at 529 nm, and normalized to OD measured at 600 nm Protein Purification of IA We amplified IA tagged with Strep-tag II on the C-terminus using the primers IA-StrepII-F and IA-StrepII-R, and cloned the PCR product into pPro29b[41] after the promoter $P_{prpB}$ to make pPro29b-IA. BLR(DE3) *E. coli* was transformed with pPro29b-IA, and an overnight culture was inoculated into a liter of LB medium with ampicillin to an initial $Abs_{600}$ of 0.05. We grew the culture at 37° C. until the $Abs_{600}$ reached 0.6, induced it with 20 mM propionate, and grew it overnight at 20° C. The cells were pelleted, resuspended in binding buffer (20 mM sodium phosphate, 280 nM NaCl, 6 mM potassium chloride, pH 7.4), sonicated, and centrifuged. The tagged protein was purified from the supernatant with a gravity flow column using StrepTactin Sepharose High Performance (GE Healthcare) following the manufacturer's instructions. Protein concentration was determined using the Pierce BCA Protein Assay Kit (Thermo Scientific).

Gel Electrophoresis Mobility Shift Assay (EMSA)

The region from the promoters $P_C$ to $P_{BAD}$ was amplified from pCtl-RFP-$S_{AraC}$ using the primers EMSA-AraReg-F and EMSA-AraReg-R. $I_1$ of the region between $P_C$ and $P_{BAD}$ was synthesized using the primers EMSA-I1-F and EMSA-I1-R. $I_1I_2$ of the region between $P_C$ and $P_{BAD}$ was synthesized using the primers EMSA-I1I2-F and EMSA-I1I2-R. Cy5 indicates that the primer was labeled with the Cy5 fluorophore (FIG. 28). DNA duplexes were synthesized from the primers by mixing the pairs of oligonucleotides at 10 μM concentration in Phusion HF PCR buffer (New England BioLabs), heating for 1 min at 95° C., and cooling to 25° C. over 1 hour. We incubated purified IA (0-10 nM) with Cy5 labeled DNA duplexes (20 nM) in binding buffer (10 mM Tris-HCl, 1 mM EDTA, 100 mM KCl, 1 mM dithioerythritol, 5% glycerol, pH 7.4) at room temperature (20° C.±2° C.) for 20 min. 10 μM IPP was added to test its effect on IA binding to DNA. Samples were prepared and run on a 6% DNA retardation gel (Invitrogen) according to the manufacturer's instructions. Gels were viewed using MultiImage III (Alpha Innotech) equipped with a Cy5 filter.

FRET DNA Binding Assay $I_1$ of the region between the promoters $P_C$ and $P_{BAD}$ was synthesized using the primers: I1-1F, I1-2F, I1-3R, and I1-4R. FL indicates that the primer was labeled with 6-FAM fluorescein fluorophore, and BQ indicates that the primer was labeled with Black Hole Quencher 1. Two pairs of duplexes were synthesized from the primers: $I_1$-FL from pairing $I_1$-1F and $I_1$-4R, and $I_1$-BQ from pairing $I_1$-2F and I1-3R. We synthesized DNA duplexes from the primers by mixing each pair of oligonucleotides at 10 μM concentration in Phusion HF PCR buffer, heating for 1 min at 95° C., and cooling to 25° C. over 1 hour. A negative control duplex $I_1$-NC was synthesized using unlabeled $I_1$-3R.

IA's ability to bind $I_1$ was determined by incubating purified IA (0-20 nM) with $I_1$-FL (100 nM) and $I_1$-BQ (125 nM) in binding buffer (10 mM Tris-HCl, pH 7.4, 1 mM EDTA, 100 mM KCl, 1 mM dithioerythritol, 5% glycerol) at room temperature (20° C.±2° C.) for 15 min Fluorescence measurements were made with a Spectramax M2 (Molecular Devices) exciting at 495 nm and measuring emission at 520 nm. The experiment was performed in triplicate.

We synthesized $I_1I_2$ DNA duplexes using the primers I1I2-1F, I1I2-2F, I1I2-3R, and I1I2-4R. An unlabeled I1I2-3R primer was used to synthesize a negative control duplex. IA's ability to bind $I_1I_2$ was determined as described above. IPP (500 nM) was added to test its effect on IA binding to $I_1I_2$. The experiment was performed in triplicate.

Luria-Delbruck Fluctuation Analysis

We transformed E. coli MG1655 with pMut-$S_{IA44}$, and grew different dilutions of the transformation on LB agar plates with ampicillin for 1 day at 37° C. Thirty colonies were picked and resuspended in 100 μl of water. 50 μl of each sample was plated on a LB agar plate with 100 μg/ml rifampicin, and 50 μl for six colonies was serially diluted and plated on LB agar plates. The plates were incubated overnight at 37° C. Colonies on each plate were counted using an automated colony counting software provided with the Biospectrum Multispectral Imaging System (Ultra-Violet Products Ltd.). Mutation rates were calculated using FALCOR[42] with the "MSS Maximum Likelihood Estimator" setting. The experiment was repeated with pMut-$S_{AC}$, pMut-$S_{IA32}$, pNeg-$S_{IA44}$.

Assessing Phenotypic Distribution after 24 Hours of FREP

For evolving increased IPP production, we transformed E. coli MG1655 with pMut-RFP-$S_{IA44}$, and grew different dilutions of the transformation on a LB agar plate with ampicillin for 1 day at 37° C. Ten mutants with the lowest RFP expression by visual inspection were picked, inoculated into LB medium with ampicillin, and grown overnight at 37° C. Overnight cultures of each mutant were inoculated into fresh LB medium the next day to an $Abs_{600}$ of 0.05, grown to an $Abs_{600}$ of 0.4 at 37° C., made electrocompetent, transformed with pLyc, plated on a LB agar plate with chloramphenicol, and grown for 1 day at 37° C. We picked a colony from each plate, inoculated it into LB medium with chloramphenicol, and assayed it for lycopene production. The same experiment was repeated with pMut-RFP-$S_{AraC}$, except 10 mM arabinose was added to the LB agar plates and medium.

For evolution of increased tyrosine production, we transformed DJ238 with pMut-RFP-$S_{aroF3}$, plated on a LB agar plate with ampicillin, and grew the transformants for 1 day at 37° C. Ten mutants with the lowest RFP expression by visual inspection were picked from the plate, inoculated into MOPS minimal medium with 0.5% glucose and ampicillin, and grown for 24 h at 37° C. Each culture was assayed for tyrosine production.

Long-Term Experiment for Increased Lycopene Production Using FREP

E. coli MG1655 were transformed with pMut-$S_{IA44}$ and pLyc. Cells were plated on a LB agar plate with ampicillin and chloramphenicol, and grown for 2 days at 37° C. We picked ten colonies and assayed each for lycopene production. The colony that produced the most lycopene was passaged to evolve further, and the average of the three highest production levels is reported. A total of 6 passages was performed to evolve over 432 hours. The same experiment was repeated with pMut-$S_{IA32}$ and pMut-$S_{AraC}$. 10 mM arabinose was added to the LB agar plates with antibiotics for pMut-$S_{AraC}$.

Assay for Lycopene Production

Cells were grown in LB medium with antibiotics for 20 hours at 37° C. We centrifuged 1 ml of culture at 13,000×g for 1 min, removed the supernatant, and washed the pellet with 1 ml of water. 1 mL of acetone was added to the washed pellet, and the sample was vortexed and incubated at 55° C. for 15 min. We centrifuged the sample at 13,000×g for 1 min, transferred the supernatant to a cuvette, and measured the absorbance at 470 nm with a spectrophotometer. The $Abs_{470}$ data was calibrated to a lycopene standard purchased from Sigma-Aldrich. The amount of lycopene extracted from a culture was normalized to the dry cell weight (dcw) calculated from the $Abs_{600}$ (0.41 g dcw/$Abs_{600}$[43]).

Assay for L-Tyrosine Production

Cells were grown in either LB or MOPS minimal medium with 0.5% glucose and antibiotics for 20 hours at 37° C. 500 μL of culture was centrifuged at 13,000×g for 1 min, the supernatant was filtered through a 0.452 μm centrifugal filter (VWR) and used for HPLC analysis. L-tyrosine data were quantified using HPLC and verified using LC-MS as described elsewhere[13]. L-tyrosine concentrations were calibrated to standards purchased from Sigma-Aldrich.

CITED REFERENCES

1. Elena, S. F., Cooper, V. S. & Lenski, R. E. Punctuated evolution caused by selection of rare beneficial mutations. *Science* 272, 1802-1804 (1996).
2. Desai, M. M & Fisher, D. S. The balance between mutator and nonmutators in asexual populations. *Genetics* 188, 997-1014 (2011).
3. Sniegowski, P. D., Gerrish, P. J. & Lenski, R. E. Evolution of high mutation rates in experimental populations of *E. coli*. *Nature* 387, 703-705 (1997).
4. Zhang, Q. et al. Acceleration of Emergence of Bacterial Antibiotic Resistance in Connected Microenvironments. *Science* 333, 1764-1767 (2011).
5. Stich, M., Manrubia, S. C. & Lázaro, E. Variable Mutation Rates as an Adaptive Strategy in Replicator Populations. *PLoS ONE* 5: e11186 (2010).
6. Giruad, A. et al. Costs and benefits of high mutation rates: adaptive evolution of bacteria in the mouse gut. *Science* 291, 2606-2608 (2001).
7. Dietrich, J. A., McKee, A. E. & Keasling, J. D. High-throughput metabolic engineering: advances in small-molecule screening and selection. *Annual Review Biochemistry* 79, 563-590 (2010).
8. Hibbert, E. G. et al. Directed evolution of biocatalytic processes. *Biomol. Eng.* 22, 11-19 (2005).
9. Greener, A., Callahan, M. & Jerpseth, B. An efficient random mutagenesis technique using an *E. coli* mutator strain. *Molecular Biotechnology* 7, 188-195 (1997).
10. Portnoy, V. A., Bezdan, D. & Zengler, K. Adaptive laboratory evolution—harnessing the power of biology for metabolic engineering. *Current Opinion in Biotechnology* 22, 590-594 (2011).

11. Liu, C. et al. Sequential establishment of stripe patterns in an expanding cell population. *Science* 334, 238-241 (2011).
12. Juminaga, D. et al. Modular engineering of L-tyrosine production in *Escherichia coli*. *Applied and Environmental Microbiology* 78, 89-98 (2012).
13. Pittard, J., Camakaris, H., & Yang, J. The TyrR regulon. *Molecular Microbiology* 55, 16-26 (2005).
14. Schaaper, R. M. Mechanisms of mutagenesis in the *Escherichia coli* mutator mutD5: role of DNA mismatch repair. *Proc. Natl. Acad. Sci. USA* 85, 8126-8130 (1988).
15. Chang, M. C. Y. & Keasling, J. D. Production of isoprenoid pharmaceuticals by engineered microbes. *Nature Chemical Biology* 2, 674-681 (2006).
16. Keasling, J. D. & Chou, H. Metabolic engineering delivers next-generation biofuels. *Nature Biotechnology* 26, 298-299 (2008).
17. Soisson, S. M., MacDougall-Shackleton, B., Schleif, R. & Wolberger, C. Structural basis for ligand-regulated oligomerization of AraC. *Science* 276, 421-425 (1997).
18. Lange, B. M., Rujan, T., Martin, W. & Croteau, R. Isoprenoid biosynthesis: the evolution of two ancient and distinct pathways across genomes. *Proc. Natl. Acad. Sci. USA* 97, 13172-13177 (2000).
19. Hahn, F. M., Hurlburt, A. P. & Poulter, C. D. *Escherichia coli* open reading frame 696 is idi, a nonessential gene encoding isopentenyl diphosphate isomerase. *Journal of Bacteriology* 181, 4499-4504 (1999).
20. De Ruyck, J., Oudjama, Y. & Wouters, J. Monoclinic form of isopentenyl diphosphate isomerase: a case of polymorphism in biomolecular crystals. *Acta. Cryst. F*64, 239-242 (2008).
21. Hellman, L. M. & Fried, M. G. Electrophoretic mobility shift assay (EMSA) for detecting protein-nucleic acid interactions. *Nature Protocols* 2, 1849-1861 (2007).
22. Heyduk, T. & Heyduk, E. Molecular beacons for detecting DNA binding proteins. *Nature Biotechnology* 20, 171-176 (2002).
23. Traven, A., Jelicic, B. & Sopta, M. Yeast Gal4: a transcriptional paradigm revisited. *EMBO* 7, 496-499 (2006).
24. Fields, S. & Song, O.-k. A novel genetic system to detect protein-protein interactions. *Nature* 340, 245-246 (1989).
25. Robinson, C. R. & Sauer, R. T. Optimizing the stability of single-chain proteins by linker length and composition mutagenesis. *Proc. Natl. Acad. Sci. USA* 95, 5929-5934 (1998).
26. D.-K. Ro et al. Production of the antimalarial drug precursor artemisinic acid in engineered yeast. *Nature* 440, 940-943 (2006).
27. Mayer, M. P., Hahn, F. M., Stillman, D. J. & Poulter, C. D. Disruption and mapping of IDI, the gene for isopentenyl diphosphate isomerase in *Saccharomyces cerevisiae*. *Yeast* 8, 743-748 (1992).
28. Fischer, M. J., Meyer, S., Claudel, P., Bergdoll, M. & Karst, F. Metabolic engineering of monoterpene synthesis in yeast. *Biotechnology and Bioengineering* 108, 1883-1892 (2011).
29. Rosche, W. A. & Foster, P. L. Determining Mutation Rates in Bacterial Populations. *Methods* 20, 4-17 (2000).
30. Alper, H., Miyaoku, K., Stephanopoulos, G. Construction of lycopene-overproducing *E. coli* strains by combining systematic and combinatorial gene knockout targets. *Nature Biotechnology* 23, 612-616 (2005).
31. Wang, H. H. et al. Programming cells by multiplex genome engineering and accelerated evolution. *Nature* 460, 894-899 (2009).
32. Martin, V. J. et al. Engineering a mevalonate pathway in *Escherichia coli* for production of terpenoids. *Nature Biotechnology* 7, 796-802 (2003).
33. Datsenko, K. A. & Wanner, B. L. One-step inactivation of chromosomal genes in *Escherichia coli* K-12 using PCR products. *Proc. Natl. Acad. Sci. USA* 97, 6640-6645 (2000).
34. Lee, S. K. et al. Directed evolution of AraC for improved compatibility of arabinose- and lactose-inducible promoters. *Applied and Environmental Microbiology* 73, 5711-5715 (2007).
35. Jensen, P. D. & Hammer, K. The sequence of spacers between the consensus sequences modulates the strength of prokaryotic promoters. *Applied and Environmental Microbiology* 64, 82-87 (1998).
36. Kwok, T., Yang, J., Pittard, A. J., Wilson, T. J. & Davidson, B. E. Analysis of an *Escherichia coli* mutant TyrR protein with impaired capacity for tyrosine mediated repression, but still able to activate at sigma 70 promoters. *Molecular Microbiology* 17, 471-481 (1995).
37. Koyanagi, T., Katayama, T., Suzuki, H. & Kumagai, H. Altered oligomerization properties of N316 mutants of *Escherichia coli* TyrR. *Journal of Bacteriology* 190, 8238-8243 (2008).
38. Cui, J. & Somerville, R. L. Mutational uncoupling of the transcriptional activation function of the TyrR protein of *Escherichia coli* K-12 from the repression function. *Journal of Bacteriology* 175, 303-306 (1993).
39. Lawley, B. & Pittard, A. J. Regulation of aroL expression by TyrR protein and Trp repressor in *Escherichia coli* K-12. *Journal of Bacteriology* 176, 6921-6930 (1994).
40. Yang, J., Wang, P. & Pittard, A. J. Mechanism of repression of the aroP P2 promoter by the TyrR protein of *Escherichia coli*. *Journal of Bacteriology* 181, 6411-6418 (1999).
41. Lee, S. K. & Keasling, J. D. Heterologous protein production in *Escherichia coli* using the propionate-inducible pPro system by conventional and auto-induction methods. *Protein Expression and Purification* 61, 197-203 (2008).
42. Hall, B. M., Ma, C. X., Liang, P. & Singh, K. K. Fluctuation AnaLysis CalculatOR: a web tool for the determination of mutation rate using Luria-Delbrück fluctuation analysis. *Bioinformatics* 25, 1564-1565 (2009).
43. Kim, S. W. & Keasling, J. D. Metabolic engineering of the nonmevalonate isopentenyl diphosphate synthesis pathway in *Escherichia coli* enhances lycopene production. *Biotechnology & Bioengineering* 72, 408-415 (2001).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A system for modulating mutagenesis frequency of a host cell, comprising a host cell comprising: (a) a synthetic transcription factor (TF) comprising a first peptide capable of binding a target ligand, a second peptide capable of binding a target DNA, and a peptide linker linking the first and second peptides, wherein the first peptide and the second peptide are from different proteins, and (b) a mutator module comprising a target promoter operably linked to a gene that is capable of increasing a mutation rate of the host cell; wherein the host cell has a mutator rate (R) which is inversely proportional to a phenotypic trait (P); wherein the first peptide is a ligand-binding domain of Idi, Idi1 or Erg20, and P is isoprenoid or lycopene production, and (i) the second peptide is a DNA-binding domain (DBD) of AraC and the target promoter is an araBAD promoter and the host cell is a prokaryotic cell, or (ii) the second peptide is a DNA-binding domain (DBD) of Gal4 and the target promoter is a GAL promoter and the host cell is a yeast cell.

2. The system of claim 1 wherein the host cell comprises a nucleic acid comprising a nucleotide sequence encoding the synthetic TF.

3. The system of claim 2 wherein the host cell comprises a vector capable of stable maintenance of the nucleic acid.

4. The system of claim 3 wherein the vector is an expression vector.

5. The system of claim 1, wherein (i) when the host cell is a prokaryotic cell the gene that is capable of increasing a mutation rate of the host cell is *Escherichia coli* mutD5, *Bacillus subtilis* mutM, *Pseudomona aeruginosa* mutS, *Pseudomonas aeruginosa* mutL, or *Synechococcus* sp. mutS, and (ii) when the host cell is a yeast cell the gene that is capable of increasing a mutation rate of the host cell is *Saccharomyces cerevisiae* msh2, or *Saccharomyces cerevisiae* him1.

6. The system of claim 1, wherein the first peptide is a ligand-binding domain of Idi and the second peptide is a DNA-binding domain (DBD) of AraC and the target promoter is the araBAD promoter or the second peptide is a DNA-binding domain (DBD) of Gal4 and the target promoter is a GAL promoter.

7. The system of claim 6, wherein the GAL promoter is $P_{GAL10}$.

8. The system of claim 1, wherein the first peptide is a ligand-binding domain of Idi, Idi1 or Erg20, and the second peptide is a DNA-binding domain (DBD) of Gal4 and the target promoter is a GAL promoter.

9. The system of claim 8, wherein the GAL promoter is $P_{GAL10}$.

10. The system of claim 1, wherein the host cell is a prokaryotic cell which is a species of *Escherichia, Enterobacter, Azotobacter, Erwinia, Bacillus, Pseudomonas, Klebsiella, Proteus, Salmonella, Serratia, Shigella, Rhizobia, Vitreoscilla,* or *Paracoccus*.

11. The system of claim 10, wherein the prokaryotic cell is a species of *Escherichia*.

12. The system of claim 11, wherein the prokaryotic cell is *Escherichia coli*.

13. The system of claim 1, wherein the host cell is a yeast cell which is a species of *Saccharomyces* or Candida.

14. The system of claim 13, wherein the yeast cell is a species of *Saccharomyces*.

15. The system of claim 14, wherein the yeast cell is *Saccharomyces cerevisiae*.

* * * * *